(12) United States Patent
Zebala et al.

(10) Patent No.: US 10,660,909 B2
(45) Date of Patent: May 26, 2020

(54) METHOD FOR TREATING CANCER USING CHEMOKINE ANTAGONISTS

(71) Applicant: Syntrix Biosystems Inc., Auburn, WA (US)

(72) Inventors: John A. Zebala, Issaquah, WA (US); Dean Y. Maeda, Seattle, WA (US); Aaron D. Schuler, Auburn, WA (US)

(73) Assignee: Syntrix Biosystems Inc., Auburn, WA (US)

(*) Notice: Subject to any disclaimer, the term of this patent is extended or adjusted under 35 U.S.C. 154(b) by 0 days.

(21) Appl. No.: 15/903,503

(22) Filed: Feb. 23, 2018

(65) Prior Publication Data

US 2018/0177808 A1 Jun. 28, 2018

Related U.S. Application Data

(63) Continuation-in-part of application No. 15/354,838, filed on Nov. 17, 2016, now abandoned.

(51) Int. Cl.

| A61K 31/69 | (2006.01) |
| --- | --- |
| A61K 33/24 | (2019.01) |
| A61P 35/00 | (2006.01) |
| A61K 39/395 | (2006.01) |
| A61K 39/00 | (2006.01) |
| C07K 16/28 | (2006.01) |
| A61K 45/06 | (2006.01) |

(52) U.S. Cl.
CPC .............. *A61K 31/69* (2013.01); *A61K 33/24* (2013.01); *A61K 39/0011* (2013.01); *A61K 39/3955* (2013.01); *A61K 39/39558* (2013.01); *A61P 35/00* (2018.01); *C07K 16/2818* (2013.01); *A61K 45/06* (2013.01); *A61K 2039/5158* (2013.01); *A61K 2039/572* (2013.01)

(58) Field of Classification Search
CPC ..... A61K 31/69; A61K 31/495; A61K 31/555
USPC ........................................................ 514/247
See application file for complete search history.

(56) References Cited

U.S. PATENT DOCUMENTS

| 6,022,884 | A | 2/2000 | Mantlo et al. |
| 6,184,237 | B1 | 2/2001 | Mantlo et al. |
| 6,333,341 | B1 | 12/2001 | Mantlo et al. |
| 6,458,813 | B1 | 10/2002 | Mantlo et al. |
| 7,132,445 | B2 | 11/2006 | Taveras et al. |
| 7,176,310 | B1 | 2/2007 | Baughman et al. |
| 9,707,248 | B2 * | 7/2017 | Zebala .............. A61K 9/0053 |

(Continued)

FOREIGN PATENT DOCUMENTS

| EP | 1123276 B1 | 1/2003 |
| WO | WO 1993/010102 A1 | 5/1993 |

(Continued)

OTHER PUBLICATIONS

Jaffer and Ma, Transl Cancer Res (Sep. 2016), vol. 5(Suppl 4), pp. S616-S628. (Year: 2016).*

(Continued)

*Primary Examiner* — Craig D Ricci
*Assistant Examiner* — Janet L. Coppins
(74) *Attorney, Agent, or Firm* — Baker Hostetler

(57) ABSTRACT

What is described is a method for treating cancer in a patient in need of such treatment through the use of an antagonist to CXCR1 and/or CXCR2 receptors by administering a therapeutically effective amount of an antagonist of CXCR1 and/or CXCR2, or pharmaceutical compositions thereof, either alone as monotherapy, or in combination with at least one other anticancer therapy.

29 Claims, 22 Drawing Sheets

(56) References Cited

U.S. PATENT DOCUMENTS

| | | | |
|---|---|---|---|
| 2004/0116479 A1 | 1/2004 | Mullay et al. | |
| 2010/0210593 A1 | 8/2010 | Maeda et al. | |
| 2012/0046243 A1 | 2/2012 | Maeda et al. | |
| 2014/0206647 A1 | 7/2014 | Maeda et al. | |
| 2014/0256678 A1 | 9/2014 | Maeda et al. | |
| 2015/0038461 A1* | 2/2015 | Zebala | A61K 9/0053 514/64 |
| 2015/0147341 A1* | 5/2015 | Zebala | A61K 9/0053 424/158.1 |
| 2017/0128474 A1 | 5/2017 | Zebala et al. | |
| 2018/0177808 A1 | 6/2018 | Zebala et al. | |
| 2018/0296580 A1 | 10/2018 | Zebala et al. | |

FOREIGN PATENT DOCUMENTS

| | | |
|---|---|---|
| WO | WO 2003/024448 A2 | 3/2003 |
| WO | WO 2006/024823 A1 | 3/2006 |
| WO | WO 2006/028958 A2 | 3/2006 |
| WO | WO 2006/029879 A2 | 3/2006 |
| WO | WO 2006/105021 A2 | 10/2006 |
| WO | WO 2007/005874 A2 | 1/2007 |
| WO | WO 2006/024823 A9 | 3/2007 |
| WO | WO 2007/124424 A2 | 11/2007 |
| WO | WO 2008/061795 A2 | 5/2008 |
| WO | WO 2008/073936 A1 | 6/2008 |
| WO | WO 2008/123469 A1 | 10/2008 |
| WO | WO 2008/132601 A1 | 11/2008 |
| WO | WO 2009/009116 A2 | 1/2009 |
| WO | WO 2009/016088 A1 | 2/2009 |
| WO | WO 2009/044273 A2 | 4/2009 |
| WO | WO 2009/071476 A1 | 6/2009 |
| WO | WO 2009/106539 A1 | 9/2009 |
| WO | WO 2010/007382 A1 | 1/2010 |
| WO | WO 2010/015613 A1 | 2/2010 |
| WO | WO 2010/019570 A2 | 2/2010 |
| WO | WO 2010/031835 A2 | 3/2010 |
| WO | WO 2010/032875 A2 | 3/2010 |
| WO | WO 2010/077634 A1 | 7/2010 |
| WO | WO 2010/091543 A1 | 8/2010 |
| WO | WO 2010/127978 A1 | 11/2010 |
| WO | WO 2010/131145 A1 | 11/2010 |
| WO | WO 2010/131146 A1 | 11/2010 |
| WO | WO 2010/131147 A1 | 11/2010 |
| WO | WO 2011/025838 A1 | 3/2011 |
| WO | WO 2011/028683 A1 | 3/2011 |
| WO | WO 2011/070024 A1 | 6/2011 |
| WO | WO 2011/107553 A1 | 9/2011 |
| WO | WO 2011/109400 A2 | 9/2011 |
| WO | WO 2011/131407 A1 | 10/2011 |
| WO | WO 2011/133888 A1 | 10/2011 |
| WO | WO 2011/140249 A2 | 11/2011 |
| WO | WO 2012/032433 A1 | 3/2012 |
| WO | WO 2012/080456 A1 | 6/2012 |
| WO | WO 2012/080457 A1 | 6/2012 |
| WO | WO 2012/145493 A1 | 10/2012 |
| WO | WO 2013/061002 A1 | 5/2013 |
| WO | WO 2013/061004 A1 | 5/2013 |
| WO | WO 2013/061005 A1 | 5/2013 |
| WO | WO 2013/079174 A1 | 6/2013 |
| WO | WO 2013/087699 A1 | 6/2013 |
| WO | WO 2013/119716 A1 | 8/2013 |
| WO | WO 2013/132044 A1 | 9/2013 |
| WO | WO 2013/169264 A1 | 11/2013 |
| WO | WO 2014/008218 A1 | 1/2014 |
| WO | WO 2014/036357 A1 | 3/2014 |

OTHER PUBLICATIONS

Diaz et al.; "Increased circulating myeloid-derived suppressor cells correlate with clinical cancer stage, metastatic tumor burden, and doxorubicin-cyclophosphamide chemotherapy"; Cancer Immunol Immunother; vol. 58; 2009; p. 49-59.

Schmidt et al.; "Pretreatment Levels of Peripheral Neutrophils and Leukocytes As Independent Predictors of Overall Survival in Patients With American Joint Committee on Cancer Stave IV Melanoma: Results of the EORTC 18951 Biochemotherapy Trial"; Journal of Clinical Oncology; vol. 25 No. 12; Apr. 2007; p. 1562-1569.

Tarhini et al.; "Immune Monitoring of the Circulation and the Tumor Microenvironment in Patients with Regionally Advanced Melanoma Receiving Neoadjuvant Ipilimumab"; PLOS ONE; vol. 9 Issue 2; Feb. 2014; 9 pages.

Gebhardt et al.; "Myeloid Cells and Related Chronic Inflammatory Factors as Novel Predictive Markers in Melanoma Treatment with Ipilimumab"; Clin Cancer Research; vol. 21(24); Dec. 2015; p. 5453-5459.

Weide et al.; "Myeloid-Derived Suppressor Cells Predict Survival of Patients with Advanced Melanoma: Comparison with Regulatory T Cells and NY-ESO-1- or Melan-A-Specific T Cells"; Clin Cancer Research; vol. 20(6); Mar. 2014; p. 1601-1609.

Mandruzzato et al.; "IL4Ra+ Myeloid-Derived Suppressor Cell Expansion in Cancer Patients"; The Journal of Immunology; vol. 182; 2009; p. 6562-6568.

Ferrucci et al.; "Baseline neutrophil-to-lymphocyte ratio is associated with outcome of ipilimumab-treated metastatic melanoma patients"; British Journal of Cancer; vol. 112; 2015; p. 1904-1910.

Guthrie et al.; "The systemic inflammation-based neutrophil-lymphocyte ratio: Experience in patients with cancer"; Critical Reviews in Oncology/Hematology; vol. 88; 2013; p. 218-230.

Valpione et al.; "Personalised medicine: Development and external validation of a prognostic model for metastatic melanoma patients treated with ipilimumab"; European Journal of Cancer; vol. 51; 2015; p. 2086-2094.

Maeda et al.; "Boronic acid-containing CXCR1/2 antagonists: Optimization of metabolic stability, in vivo evaluation, and a proposed receptor binding model"; Bioorganic & Medicinal Chemistry Letters; vol. 25; 2015; p. 2280-2284.

Sharpless et al.; "Both products of the mouse Ink4a/Arf locus suppress melanoma formation in vivo"; Oncogene; vol. 22; 2003; p. 5055-5059.

Herschkowitz et al.; "Comparative oncogenomics identifies breast tumors enriched in functional tumor-initiating cells"; PNAS; vol. 109 No. 8; Feb. 2012; p. 2778-2783.

Di Mitri et al.; "Tumour-infiltrating Gr-1+ myeloid cells antagonize senescence in cancer"; Nature; vol. 515; Nov. 2014; 17 pages.

Acharyya et al.; "A CXCL1 Paracrine Network Links Cancer Chemoresistance and Metastasis"; Cell; vol. 150; Jul. 2012; p. 165-178.

Highfill et al.; "Disruption of CXCR2-Mediated MDSC Tumor Trafficking Enhances Anti-PD1 Efficacy"; Science Translation Medicine; vol. 6 Issue 237; May 2014; 14 pages.

Katoh et al.; "CXCR2-Expressing Myeloid-Derived Suppressor Cells Are Essential to Promote Colitis-Associated Tumorigenesis"; Cancer Cell; vol. 24; Nov. 2013; p. 631-644.

Maroulakou et al.; "Prostate and mammary adenocarcinoma in transgenic mice carrying a rat C3(1) simian virus 40 large tumor antigen fusion gene"; Proc. Nat'l Acad. Sci. USA; vol. 91; Nov. 1994; p. 11236-11240.

Alfaro et al.; "Tumor-produced interleukin-8 attracts human myeloid-derived suppressor cells and elicits extrusion of neutrophil extracellular traps (NETs)"; American Association for Cancer Research; 2016; 37 pages.

Schuler et al.; Bioorganic & Medicinal Chem Letters; 2015; vol. 25; pp. 3793-3797.

Alderton, Gemma K.; "Two hits are better than one"; Nature Reviews; vol. 14; Jul. 2014; one page.

Cao et al.; "The cytokine/chemokine pattern in the bone marrow environment of multiple myeloma patients"; Experimental Hematology; vol. 38; 2010; p. 860-867.

Gorgun et al.; "Tumor-promoting immune-suppressive myeloid-derived suppressor cells in the multiple myeloma microenvironment in humans"; Blood; vol. 121 No. 15; Apr. 2013; p. 2975-2987.

Schinke et al.; "IL8-CXCR2 pathway inhibition as a therapeutic strategy against MDS and AML stem cells"; Blood; vol. 125 No. 20; May 2015; p. 3144-3152.

(56) References Cited

OTHER PUBLICATIONS

Zhang et al.; "CXCL2/MIF-CXCR2 signaling promotes the recruitment of myeloid-derived suppressor cells and is correlated with prognosis in bladder cancer"; Oncogene; 2016; 10 pages.
Lu et al.; "Effective combinatorial immunotherapy for castration-resistant prostate cancer"; Nature; vol. 543 Mar. 2017; p. 728-732; addtional documents total of 19 pages.
Liao et al.; "KRAS-IRF2 Axis Drives Immune Suppression and Immune Therapy Resistance in Colorectal Cancer"; Cancer Cell; vol. 35; Apr. 2019; p. 559-572 and e1-e7.
Ha et al.; "Role of the CXCL8-CXCR1/2 Axis in Cancer and Inflammatory Diseases"; Theranostics; vol. 7 Issue 6; 2017; p. 1543-1588.
Dhanak et al.; "Small-Molecule Targets in Immuno-Oncology"; Cell Chemical Biology; vol. 24; Sep. 2017; p. 1148-1160.
"SX-682 Treatment in Subjects with Metastatic Melanoma Concurrently Treated With Pembrolizumab"; https://clinicaltrials.gov/ct2/show/NCT03161431; accessed Apr. 26, 2019; 7 pages.
Martin-Liberal et al.; "The expanding role of immunotherapy"; Cancer Treatment Reviews; vol. 54; 2017; p. 74-86.
Susek et al. "The Role of CXC Chemokine Receptors 1-4 on Immune Cells in the Tumor Microenvironment"; Frontier in Immunology; vol. 9; Sep. 2018; 9 pages.
International Patent Application No. PCT/US2019/019305; Int'l Written Opinion and Search Report; dated Jun. 6, 2019; 13 pages.

\* cited by examiner

METHOD FOR TREATING CANCER USING CHEMOKINE ANTAGONISTS

GOVERNMENT RIGHTS

This invention was made with government support under Grant Number HL072614 awarded by the National Institutes of Health. The government has certain rights in the invention.

CROSS REFERENCE TO RELATED APPLICATIONS

The entire disclosure of U.S. patent application Ser. No. 15/354,838 filed on Nov. 17, 2016, is incorporated herein by reference.

TECHNICAL FIELD

The disclosure herein relates to a method for treating cancer in a patient in need of such treatment through the use of an antagonist to CXCR1 and/or CXCR2 receptors. More specifically, the method comprises administering to said patient a therapeutically effective amount of a compound of formula I, described herein, or pharmaceutical compositions thereof, either alone as monotherapy, or in combination with at least one other anticancer therapy.

BACKGROUND

Terminally differentiated myeloid cells are essential to normal function of both the innate and adaptive immune systems. These cells protect organisms from pathogens, eliminate dying cells and mediate tissue remodeling. However, cancer pathologically alters myeloid cells into potent immunosuppressive cells known as myeloid-derived suppressor cells (MDSCs) that enable cancer progression and spread. The tumor-mediated alteration of myeloid cells is not confined to the tumor, but is a systemic phenomenon (Gabrilovich, 2012, *Nat Rev Immunol*, 12:253-68). Soluble factors released by the tumor act at distant sites that include bone marrow and spleen, where they alter macrophages and granulocytes to become immunosuppressive and accumulate within the tumor. Peripheral blood from advanced cancer patients have much higher MDSC levels compared to healthy donors (P<0.001), who have near undetectable levels (Alfaro, 2016, *Clin Cancer Res*, 22:3924-36). The MDSC lifespan is short (24-96 hours), and tumors require continuous MDSC resupply to maintain homeostasis of tumor MDSC populations (Condamine, 2014, *J Clin Invest*, 124:2626-39). Thus, an effective strategy to abrogate MDSC activity in the tumor microenvironment may be to prevent MDSC arrival to tumors, which has been shown to deplete tumors of MDSCs.

Chemokines are chemotactic proteins that have the potential to attract macrophages, T-cells, eosinophils, basophils, neutrophils and endothelial cells to sites of inflammation and tumor growth. Chemokines are typically low molecular mass (7-9 kD) proteins that can be divided into four subfamilies: CC (or β-chemokines), CXC, C (or γ-chemokines) and CX3C (or δ-chemokines). The CXC-chemokines (i.e., the ligands for CXCR1 and/or CXCR2) include, but are not limited to, interleukin-8 (IL-8, CXCL8), GROα (CXCL1), GROβ (CXCL2), GROγ (CXCL3), ENA-78 (CXCL5), GCP-2 (CXCL6), and NAP-2 (CXCL7). IP-10. Tumor secreted chemokines CXCL1, CXCL2 and CXCL5 recruit MDSCs to tumors (or a pre-metastatic niche) in numerous mouse tumor models (Condamine, 2015, *Annu Rev Med*, 66: 97-110). These chemokines all bind chemokine receptor CXCR2. Tumor secreted CXCL8 (IL-8) also recruits MDSCs (Mestas, 2004, *J Immunol*, 172:2731-38; Ben-Baruch, 2012, *Cancer Microenviron*, 5:151-64), which signals via both CXCR1 and CXCR2 receptors (Rot, 2004, *Annu Rev Immunol*, 22: 891-928). Thus, there is a clear therapeutic advantage to find a means to target both CXCR1 and CXCR2 to block MDSC recruitment during cancer growth and metastasis.

SUMMARY

The disclosure herein relates to a method for treating cancer in a patient in need of such treatment through the use of an antagonist to CXCR1 and/or CXCR2 receptors. The method comprises administering to said patient a therapeutically effective amount of at least one compound of formula I (further described herein), or pharmaceutical compositions thereof, either alone as monotherapy, or in combination another anticancer therapy.

In one embodiment, the method of treating cancer in a patient in need of such treatment, comprising administering to the patient a pharmaceutical formulation comprising a therapeutically effective amount of a CXCR1 and/or CXCR2 antagonist of formula I,

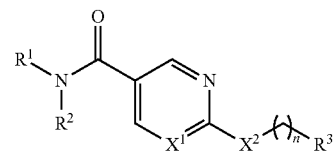

I wherein $R^1$ and $R^2$ are independently selected from the group consisting of hydrogen, 2- or 3- or 4-halophenyl, heteroalkyl, alkyl, aryl, arylalkyl, heteroaryl, heteroarylalkyl, cycloalkyl, cycloalkylalkyl, heterocyclyl, and heterocyclylalkyl;

wherein $R^3$ is selected from —$B(R^4R^5)$, —$R^6$—$B(R^4R^5)$, $R^6$, —C(O)—$R^6$, —O—$R^6$, —$S(O)_y$—$R^6$ (wherein y=0, 1, or 2), —P(O)—$(R^4R^5)$ and —$N(R^7R^8)$;

wherein $R^4$ and $R^5$ are independently hydrogen, hydroxyl, aryloxy, or alkoxy, or wherein $R^4$ and $R^5$ together form a cyclic ester, or an acid anhydride (either mixed or symmetrical);

wherein $R^6$ is selected from alkyl, aryl, arylalkyl, cycloalkyl, heteroaryl, heteroarylalkyl, heterocyclyl and heterocyclylalkyl;

wherein $R^7$ and $R^8$ are independently selected from hydrogen, alkyl, haloalkyl, aryl, cycloalkyl, arylalkyl, heteroalkyl, heterocyclyl and heterocyclylalkyl; $R^7$ and $R^8$ are both oxygen to form a nitro group; or $R^7$ and $R^8$ together with the nitrogen to which they are attached, form a heterocyclyl;

wherein $R^9$ is selected from the group consisting of hydrogen, heteroalkyl, alkyl, aminoalkyl, aryl, arylalkyl, carboxyalkyl, heteroaryl, heteroarylalkyl, cycloalkyl, cycloalkylalkyl, heterocyclyl, and heterocyclylalkyl; or —$B(R^4R^5)$, —$BF_3^-M^+$, —$R^6$—B$(R^4R^5)$, —$R^6$—$BF_3^-M^+$, $R^6$, —C(O)—$R^6$, —O—$R^6$, —$S(O)_y$—$R^6$ (wherein y=0, 1, or 2), —P(O)—$(R^4R^5)$ and —$N(R^7R^8)$; or an ionizing group selected from the group consisting of carboxylates, amines, phosphonates, and phosphates;

wherein $X^1$ is carbon or nitrogen; $X^2$ is —S(O)$_y$— (wherein y=0, 1, or 2), —N($R^9$)—, or oxygen; and n is an integer between 0 and 8; or a pharmaceutically acceptable salt or solvate thereof.

In certain embodiments, the method comprises administering to a patient in need of treatment for cancer a therapeutically effective amount of at least one compound of formula I selected from compounds in FIG. 1 either as monotherapy, or in combination with another anticancer therapy.

In preferred embodiments, the method comprises administering to a patient in need of treatment for cancer a therapeutically effective amount of compound SX-682 either as monotherapy, or in combination with another anticancer therapy.

The disclosure herein includes methods of inhibiting CXCR1 and/or CXCR2-mediated immunosuppression by administering to the subject a CXCR1 and/or CXCR2 receptor antagonist of formula I.

Another aspect of the disclosure herein is a method of inhibiting tumor-mediated recruitment of myeloid derived suppressor cells (MDSCs) by administering to the cancer patient a CXCR1 and/or CXCR2 receptor antagonist of formula I.

The disclosure herein includes methods of inhibiting CXCR1 and/or CXCR2-mediated tumor cell proliferation by administering to the cancer patient a CXCR1 and/or CXCR2 receptor antagonist of formula I.

Examples of the cancers that may be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, blood (including lymphoma, leukemia, and myelodysplastic syndromes) esophagus, breast, muscle, connective tissue, lung (including small-cell lung carcinoma and non-small-cell carcinoma), adrenal gland, thyroid, kidney, lymphoid tissue, bone marrow or bone, glioblastoma, mesothelioma, renal cell carcinoma, gastric carcinoma, sarcoma, choriocarcinoma, cutaneous basocellular carcinoma, and testicular seminoma. In some embodiments of the disclosure herein, the cancer is melanoma, colon cancer, pancreatic cancer, breast cancer, prostate cancer, lung cancer, leukemia, a brain tumor, lymphoma, sarcoma, ovarian cancer, head and neck cancer, cervical cancer, or myelodysplastic syndromes. Cancers that are candidates for treatment with the compounds and compositions of the disclosure herein are discussed further hereafter The disclosure herein further contemplates the method of treating cancer through the use of at least one antagonist of CXCR1 and/or CXCR2 receptors, including those that antagonize by acting on the CXC receptor or its ligand, in combination with one or more additional agents. The one or more additional agents may have some CXCR1 and/or CXCR2 modulating activity and/or they may function through distinct mechanisms of action. In some embodiments, such agents comprise radiation (e.g., localized radiation therapy or total body radiation therapy) and/or other treatment modalities of a non-pharmacological nature, such as cell therapy or vaccination. When combination therapy is utilized, the antagonist of CXCR1 and/or CXCR2 and the one additional agent(s) may be in the form of a single composition or multiple compositions, and the treatment modalities may be administered concurrently, sequentially, or through some other regimen. By way of example, the disclosure herein contemplates a treatment regimen wherein administration of an antagonist to CXCR1 and/or CXCR2 receptors is maintained on a daily basis, with additional anticancer treatments (e.g., anti-PD1 antibody, carboplatin, T-cell therapy, cancer vaccination, radiation) given intermittently during the treatment period. The combination therapy may have an additive or synergistic effect. Other benefits of combination therapy are described hereafter.

In particular embodiments, the disclosure herein contemplates the use of at least one antagonist of CXCR1 and/or CXCR2 receptors in combination with immune checkpoint inhibitors. The blockade of immune checkpoints, which results in the amplification of antigen-specific T cell responses, has been shown to be a promising approach in human cancer therapeutics. Examples of immune checkpoints (enzymes, ligands and receptors), some of which are selectively upregulated in various types of tumor cells, that are candidates for blockade include indolamine 2,3-dioxygenase (IDO), tryptophan 2,3-dioxygenase (TDO), programmed cell death protein 1 (PD1); PD1 ligand (PDL1); B and T lymphocyte attenuator (BTLA); cytotoxic T-lymphocyte associated antigen 4 (CTLA4); T-cell membrane protein 3 (TIM3); lymphocyte activation gene 3 (LAG3); adenosine A2a receptor (A2aR); and killer inhibitory receptors. Immune checkpoint inhibitors, and combination therapy therewith, are discussed in detail elsewhere herein.

In particular embodiments, the disclosure herein contemplates the use of an antagonist of CXCR1 and/or CXCR2 receptors in combination with cancer vaccines. Cancer vaccines are used to treat established cancers not due to viral infections, and include the use of antigen vaccines, tumor cell vaccines, dendritic vaccines, deoxyribonucleic acid vaccines, and viral vector vaccines.

In particular embodiments, the disclosure herein contemplates the use of an antagonist of CXCR1 and/or CXCR2 receptors in combination with T-cell therapy. T-cell therapy involves the isolation, expansion, and re-introduction of a cancer patient's tumor reactive T-cells. T-cell therapy also includes the use of genetically modified T-cells expressing chimeric antigen receptors (CARs).

In other embodiments, the disclosure herein provides methods for treating cancer in a subject, comprising administering to the subject a therapeutically effective amount of at least one antagonist of CXCR1 and/or CXCR2 receptors and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The disclosure herein also contemplates the use of at least one antagonist of CXCR1 and/or CXCR2 in combination with other agents known in the art (e.g., arsenic trioxide) and other chemotherapeutic agents.

In some embodiments drawn to methods of treating cancer, the administration of a therapeutically effective amount of at least one antagonist of CXCR1 and/or CXCR2 receptors in combination with at least one other anticancer therapy (e.g. chemotherapeutic agent, immune checkpoint inhibitor, T-cell therapy, cancer vaccination, radiation) results in a cancer survival rate greater than the cancer survival rate observed by administering either therapy alone. In further embodiments drawn to methods of treating cancer, the administration of a therapeutically effective amount of at least one antagonist of CXCR1 and/or CXCR2 in combination with at least one other anticancer therapy results in a reduction of tumor size or a slowing of tumor growth greater than reduction of the tumor size or tumor growth observed by administration of one agent alone.

In further embodiments, the disclosure herein contemplates methods for treating or preventing cancer in a subject, comprising administering to the subject a therapeutically effective amount of at least one antagonist of CXCR1 and/or CXCR2 receptors and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The disclosure herein also contemplates methods of augmenting the rejection of tumor cells in a subject comprising administering at least one antagonist of CXCR1 and/or CXCR2 receptors in conjunction with at least one chemotherapeutic agent, immunotherapeutic, and/or radiation therapy, wherein the resulting rejection of tumor cells is greater than that obtained by administering either the CXCR1 and/or CXCR2 antagonist, the chemotherapeutic agent, immunotherapy, or the radiation therapy alone.

In further embodiments, the disclosure herein provides methods for treating cancer in a subject, comprising administering to the subject a therapeutically effective amount of at least one antagonist of CXCR1 and/or CXCR2 receptors and at least one immunomodulator other than a CXCR1 and/or CXCR2 antagonist. In particular embodiments, the at least one immunomodulator is selected from the group consisting of CD40L, B7, B7RP1, ant-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-α/-β, M-CSF, IL-3, GM-CSF, IL-13, and anti-IL-10. Other candidate immunomodulator agents are set forth elsewhere herein.

DETAILED DESCRIPTION

Figure 1A:
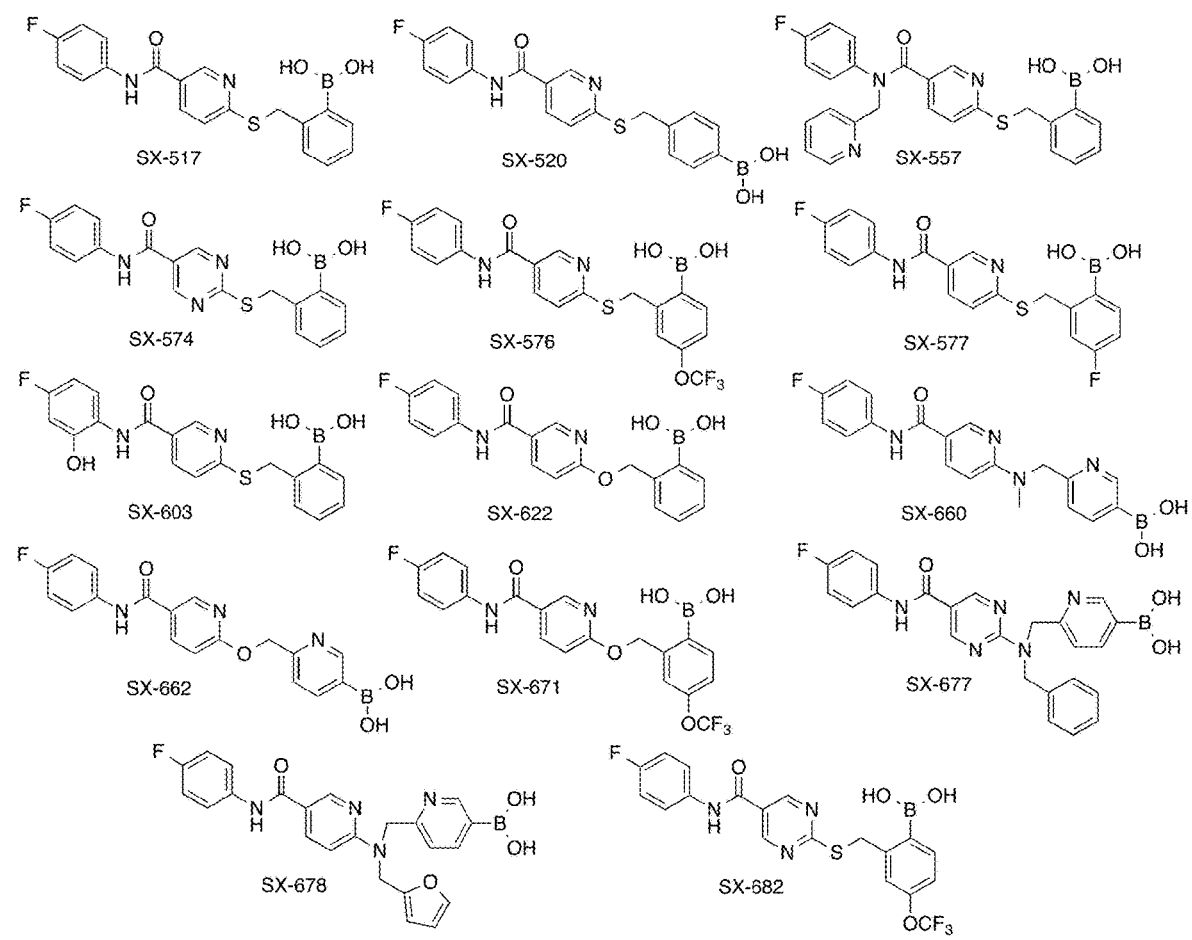
FIG. 1A shows structures of selected antagonists of CXCR1 and/or CXCR2 of formula I that include SX-517, SX-520, SX-557, SX-574, SX-577, SX-603, SX-622, SX-660, SX-662, SX-671, SX-677, SX-678, and SX-682.

Immune dysregulation is intimately associated with tumor evasion of the host immune system, resulting in tumor growth and progression. Traditional treatment approaches comprising chemotherapy and radiotherapy are generally difficult for the patient to tolerate and become less effective as tumors evolve to survive such treatments. By utilizing the patient's own immune system to identify and eliminate tumor cells, immunotherapy has the benefit of reduced toxicity. As mobilization of immunosuppressive MDSCs through CXCR1 and/or CXCR2 receptor activation comprises one mechanism manipulated by tumors to promote growth and metastasis, agents (e.g., small molecule compounds) that antagonize these receptors present a promising avenue for prophylaxis and/or treatment.

Definitions

When any substituent or variable occurs more than one time in any moiety, its definition on each occurrence is independent of its definition at every other occurrence. Also, combinations of substituents and/or variables are permissible only if such combinations result in stable compounds.

Unless indicated otherwise, the following definitions apply throughout the present specification and claims. These definitions apply regardless of whether a term is used by itself or in combination with other terms. For example, the definition of "alkyl" also applies to the "alkyl" portion of the defined term "alkoxy".

The phrase "an effective amount" or a "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of a antagonist of CXCR1 and/or CXCR2 receptors (or, e.g., a metabolite thereof) at a particular time post-administration may be indicative of whether a therapeutically effective amount has been used.

"At least one" means one or more (e.g., 1-3, 1-2, or 1).

"Composition" includes a product comprising the specified ingredients in the specified amounts, as well as any product that results, directly or indirectly, from combination of the specified ingredients in the specified amounts.

"In combination with" as used to describe the administration of at least one antagonist of CXCR1 and/or CXCR2 receptors with other medicaments in the methods of treatment of the disclosure herein, means that the compounds of formula I and the other medicaments are administered sequentially or concurrently in separate dosage forms, or are administered concurrently in the same dosage form.

"Mammal" means a human or other mammal, or means a human being.

"Patient" includes both human and other mammals, preferably human.

"Prodrug" denotes a compound that is a drug precursor which, upon administration to a subject, undergoes chemical conversion by metabolic or chemical processes to yield a compound of or a salt and/or solvate thereof. Prodrugs of the compounds of formula I or formula II or pharmaceutically acceptable salts or solvates thereof are within the scope of the disclosure herein. Prodrugs of the compounds described herein are those compounds that readily undergo chemical changes under physiological conditions to provide the compounds of the disclosure herein. Additionally, a prodrug can be converted to a compound of formula I by chemical or biochemical methods in an ex vivo environment, for example, when placed in a transdermal patch reservoir with a suitable enzyme or chemical reagent.

"Alkyl" is a saturated or unsaturated, straight or branched, hydrocarbon chain. In various embodiments, the alkyl group has 1-18 carbon atoms, i.e., is a $C_1$-$C_{18}$ group, or is a $C_1$-$C_{12}$ group, a $C_1$-$C_6$ group, or a $C_1$-$C_4$ group. A lower alkyl group has 1-6 carbons. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less than 25, 24, 23, 22, 21, 20, 19, 18, 17, 16, 15, 14, 13, 12, 11, 10, 9, 8, or 7 carbons.

"Lower alkyl" means a group having about 1 to about 6 carbon atoms in the chain which chain may be straight or branched. Non-limiting examples of suitable alkyl groups include methyl, ethyl, n-propyl, isopropyl, n-butyl, t-butyl, n-pentyl, and n-hexyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryl compounds comprise a lower alkyl group. The bond to the parent moiety is through the aryl.

"Aminoalkyl" means an $NH_2$-alkyl-group, wherein alkyl is as defined above, bound to the parent moiety through the alkyl group.

"Aryl" (sometimes abbreviated "Ar") is an aromatic carbocyclic hydrocarbon ring system. The ring system may be monocyclic or fused polycyclic (e.g., bicyclic, tricyclic, etc.). In one embodiment, the aryl group is monocyclic, and is preferably a $C_6$ ring system, i.e. a phenyl ring is a preferred aryl ring, where preferred bicyclic aryl rings are $C_8$-$C_{12}$, or $C_9$-$C_{10}$. A naphthyl ring, which has 10 carbon atoms, is a preferred polycyclic aryl ring. Unless otherwise indicated herein, the term "aryl" as used herein is meant to include aryl rings optionally substituted by one or more substituents selected from acyl (—C(O)—R), alkoxy (—O—R), alkyl, aryl, alkylamino (—N(H)—R and —N(R) R), alkylthio (—S—R), amino (—NH$_2$), azido (—N$_3$), boronyl (—B(R)R or —B(OH)$_2$ or —B(OR)$_2$), carboxy (—C (O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) where each R group is an alkyl group having less than about 12 carbons, preferably where the R group is a lower alkyl group. Non-limiting examples of suitable aryl groups include: phenyl, naphthyl, indenyl, tetrahydronaphthyl, indanyl, anthracenyl, and fluorenyl.

"Arylalkyl" refers to an alkyl group as defined substituted by one or more aryl groups as defined below. Phenyl and naphthyl are preferred aryl groups in an arylalkyl group. A preferred alkyl group is methyl, so that a preferred arylalkyl group is benzyl or benzyl having one or more substituents on the phenyl ring. Unless otherwise indicated, the term "arylalkyl" as used herein is meant to include arylalkyl groups wherein the aryl ring therein is optionally substituted by one or more substituents selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) where each R is an alkyl group having less than about 12 carbons, preferably where the R group is a lower alkyl group.

"Aryloxy" means an aryl-O-group in which the aryl group is as previously described. Non-limiting examples of suitable aryloxy groups include phenoxy and naphthoxy. The bond to the parent moiety is through the ether oxygen.

"Carboxyalkyl" means an HOOC-alkyl-group, wherein alkyl is as defined above, bound to the parent moiety through the alkyl group.

"Chemokine" means a protein molecule involved in chemotaxis.

A "chemokine-mediated disease" means a disease of which at least one element or cause is related to the regulation of a CXC chemokine.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. A multicyclic cycloalkyl substituent may include fused, spiro, or bridged ring structures. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalin, norbornyl, adamantyl and the like. Cycloalkyl substituents may be substituted or unsubstituted. In one embodiment, the cycloalkyl is unsubstituted. In another embodiment, the cycloalkyl is substituted with, e.g., 1 substituent (i.e., the cycloalkyl group is mono-substituted), or 1-2 substituents, or 1-3 substituents, or 1-4 substituents, etc. In one embodiment, the substituents that may be present on the cycloalkyl aliphatic ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) In one aspect the R group in the above substituents is an alkyl group having less than about 12 carbons, while in another aspect the R group is a lower alkyl group.

"Cycloalkylalkyl" means a cycloalkyl group bound to the parent moiety through an alkyl group. Non-limiting examples include: cyclopropylmethyl and cyclohexylmethyl.

"Cycloalkylaryl" means a cycloalkyl group bound to the parent moiety through an aryl group. Non-limiting examples include: cyclopropylphenyl and cyclohexylphenyl.

"Effective amount" or "therapeutically effective amount" is meant to describe an amount of compound or a composition of the disclosure herein effective in decreasing the action of a CXC chemokine at a CXC chemokine receptor and thus producing the desired therapeutic effect in a suitable patient.

"Fluoroalkoxy" means an alkoxy group as defined above wherein one or more hydrogen atoms on the alkoxy is or are replaced by a fluoro group.

"Fluoroalkyl" means an alkyl group as defined above wherein one or more hydrogen atoms on the alkyl are replaced by a fluoro group.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" is a saturated or unsaturated, straight or branched, chain containing carbon and at least one heteroatom. The heteroalkyl group may, in various embodiments, have on heteroatom, or 1-2 heteroatoms, or 1-3 heteroatoms, or 1-4 heteroatoms. In one aspect the heteroalkyl chain contains from 1 to 18 (i.e., 1-18) member atoms (carbon and heteroatoms), and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have 1-2 substituents, or 1-3 substituents, or 1-4 substituents, etc. Exemplary heteroalkyl substituents include esters (—C(O)—O—R) and carbonyls (—C(O)—).

"Heterocyclic" (or "heterocycloalkyl" or "heterocyclyl") refers to a non-aromatic saturated monocyclic or multicyclic ring system comprising 3 to 10 ring atoms (e.g., 3 to 7 ring atoms), or 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Examples of heterocyclic or heterocycloalkyl compounds include rings having 5 to 6 ring atoms. The prefix aza, oxa or thia before the heterocyclic or heterocycloalkyl root name means that at least a nitrogen, oxygen or sulfur atom, respectively, is present as a ring atom. The nitrogen or sulfur atom of the heterocyclic or heterocycloalkyl can be optionally oxidized to the corresponding N-oxide, S-oxide or S,S-dioxide. Any nitrogen atoms may be optionally quaternized. Non-limiting examples of monocyclic heterocyclic or heterocycloalkyl rings include: piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophen-yl, and tetrahydrothiopyranyl The heterocyclyl may be unsubstituted or substituted. In one embodiment, the heterocyclyl is unsubstituted. In another embodiment, the heterocyclyl is substituted. The substituted heterocyclyl ring may contain 1 substituent, or 1-2 substituents, or 1-3 substituents, or 1-4 substituents, etc. In one embodiment, the substituents that may be present on the heterocyclyl ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) In one aspect, the R group which is, or is part of the substituent attached to the heterocyclic ring is an alkyl group having less than about 12 carbons, while in another aspect the R group is a lower alkyl group.

"Heterocycloalkylalkyl" means a heterocycloalkyl-alkyl group, wherein said heterocycloalkyl and said alkyl are as defined above, bound to a parent moiety through the alkyl group.

"Heteroaryl" means an aromatic monocyclic or multicyclic ring system comprising 5 to 14 ring atoms, or 5 to 10 ring atoms, in which one or more of the ring atoms is an element other than carbon, for example nitrogen, oxygen or sulfur, alone or in combination. Heteroaryls can contain 5 to 6 ring atoms. The prefix aza, oxa or thio before the heteroaryl root name means that at least a nitrogen, oxygen or sulfur atom respectively, is present as a ring atom. A nitrogen atom of a heteroaryl can be optionally oxidized to the corresponding N-oxide. Any nitrogen atoms may be optionally quaternized. Non-limiting examples of heteroaryls include: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl. The heteroaryl may be unsubstituted or substituted. In one embodiment, the heteroaryl is unsubstituted. In another embodiment, the heteroaryl is substituted. The substituted heteroaryl ring may contain 1 substituent, or 1-2 substituents, or 1-3 substituents, or 1-4 substituents, etc. In one embodiment, the substituents that may be present on the heteroaryl ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) In one aspect, the R group which is, or is part of the substituent attached to the heteroaryl ring is an alkyl group having less than about 12 carbons, while in another aspect the R group is a lower alkyl group.

"Heteroaralkyl" or "heteroarylalkyl" means a heteroaryl-alkyl-group, in which the heteroaryl and alkyl are as previously described. Preferred heteroaralkyl compounds can contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is H$_2$O.

"Solvate" means a physical association of a compound of the disclosure herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

The term "substituted" means substitution with specified groups other than hydrogen, or with one or more groups, moieties or radicals which can be the same or different, with each, for example, being independently selected.

The compounds of formula I form salts that are also within the scope of the disclosure herein. Reference to compounds of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of the compounds of formula I may be formed, for example, by reacting it with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartrates, thiocyanates, toluenesulfonates (also known as tosylates), undecanoates, and the like. Additionally, acids which are generally considered suitable for the formation of pharmaceutically useful salts from basic pharmaceutical compounds.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl, and stearyl chlorides, bromides and iodides), aryalkyl halides (e.g., benzyl and phenethyl bromides), and others.

All such acid and base salts are intended to be pharmaceutically acceptable salts within the scope of the disclosure herein and all acid and base salts are considered equivalent to the free forms of the corresponding compounds for purposes of the disclosure herein.

Compounds of formula I can exist in unsolvated and solvated forms, including hydrated forms. In general, the solvated forms, with pharmaceutically acceptable solvents such as water, ethanol and the like, are equivalent to the unsolvated forms for the purposes of the disclosure herein.

Compounds of formula I and salts, solvates and prodrugs thereof, may exist in their tautomeric form (for example, as an amide or imino ether). All such tautomeric forms are contemplated herein as part of the disclosure herein.

Also within the scope of the disclosure herein are polymorphs of the compounds of the disclosure herein (i.e., polymorphs of the compounds of formula I are within the scope of the disclosure herein).

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of the disclosure herein. Individual stereoisomers of the compounds of the disclosure herein may, for example, be substantially free of other isomers, or may be admixed, for example, as racemates or with all other, or other selected, stereoisomers. The chiral centers of the compounds herein can have the S or R configuration as defined by the IUPAC 1974 Recommendations. The use of the terms "salt", "solvate", "prodrug" and the like, is intended to equally apply to the salt, solvate and prodrug of enantiomers, stereoisomers, rotamers, tautomers, racemates or prodrugs of the disclosed compounds.

The compounds of formula I may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as, for example, tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the disclosure herein may find additional utility, including but not limited to, as diagnostic and/or imaging reagents, or as cytotoxic/radiotoxic therapeutic agents. Additionally, isotopic variants of the compounds of the disclosure herein can have altered pharmacokinetic and pharmacodynamic characteristics which can contribute to enhanced safety, tolerability or efficacy during treatment. All isotopic variations of the compounds of the disclosure herein, whether radioactive or not, are intended to be encompassed within the scope of the disclosure herein.

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of a biological target, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Anticancer therapy" means any therapeutic intervention used to treat cancer in a patient in need of such treatment. Anticancer therapy can include the use of chemotherapeutic agents, immunotherapy, radiation therapy, or surgery.

Classes of compounds that can be used as the chemotherapeutic agent (antineoplastic agent) include: alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide).

Methods for the safe and effective administration of most of these chemotherapeutic agents are known to those skilled in the art.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents that disrupt microtubule formation.

"Immunotherapy" means anticancer treatments that use the patient's immune system to attack cancer cells. Immunotherapy can include: immune checkpoint inhibitors, cancer vaccines, and T-cell therapy. Examples of these immunotherapies are given below.

Immune checkpoint inhibitors include inhibitors (both small molecule and biological) of programmed cell death protein 1 (PD-1), PD-L1, cytotoxic T-lymphocyte-associated antigen 4 (CTLA-4), indoleamine 2,3-dioxygenase (IDO), tryptophan 2,3-dioxygenase (TDO), T-cell Ig and mucin domain 3 (TIM3), lymphocyte activation gene 3 (LAG3), T-cell immunoreceptor with Ig and immunoreceptor tyrosine-based inhibitory motif (ITIM) domains (TIGIT), B- and T-lymphocyte attenuator (BTLA), V-domain Ig suppressor of T-cell activation (VISTA), inducible T-cell COStimulator (ICOS), killer Ig-like receptors (KIRs), and CD39. Examples of biologic immune checkpoint inhibitors include ipilimumab, abatacept, nivolumab, pembrolizumab, tremelimumab, pidilizumab, atezolizumab, durvalumab, and avelumab. Examples of small molecule immune checkpoint inhibitors of IDO and/or TDO include indoximod, GDC-0919, F001287, GDC-0919 (NLG919), F001287, epacadostat (INCB024360), IDO-IN-1, IDO-IN-2, and navoximod (IDO-IN-7).

Cancer vaccines are used to treat established cancers not due to viral infections, and include the use of antigen vaccines, tumor cell vaccines, dendritic vaccines, deoxyribonucleic acid vaccines, and viral vector vaccines.

T-cell therapy involves the isolation, expansion, and re-introduction of a cancer patient's tumor reactive T-cells. T-cell therapy also includes the use of genetically modified T-cells expressing chimeric antigen receptors (CARs) on their surface, wherein CARs are proteins that allow the T cells to recognize an antigen on targeted tumor cells. As used herein, such an antigen on targeted tumors cells is also referred to as a "tumor antigen".

An "antagonist of CXCR1 and/or CXCR2 receptors" is a molecule that opposes the action(s) of an agonist at CXCR1 and/or CXCR2 receptors. The antagonist may oppose the action of an agonist at CXCR1 and/or CXCR2 by acting at the receptor (e.g., an allosteric small-molecule) or acting at the chemokine ligand (e.g., the HuMax-IL8 monoclonal antibody that binds CXCL8). The agonist may be selected from (but not limited to) chemokine ligands CXCL1, CXCL2, CXCL3, CXCL5, and CXCL8. The activity of an agonist may include cellular processes resulting from CXCR1 and/or CXCR2 receptor activation such as intracellular calcium release, cyclic AMP generation, cellular chemotaxis, and b-arrestin recruitment. An antagonist prevents, reduces, inhibits, or neutralizes the activity of an agonist, and an antagonist can also prevent, inhibit, or reduce constitutive activity of a target, e.g., a target receptor, even where there is no identified agonist.

In one embodiment, the method of treating cancer in a patient in need of such treatment, comprising administering to the patient a pharmaceutical composition comprising a therapeutically effective amount a CXCR1 and/or CXCR2 receptor antagonist of formula I,

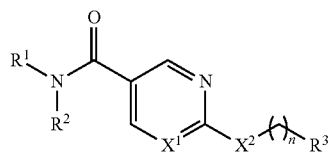

wherein $R^1$ and $R^2$ are independently selected from the group consisting of hydrogen, 2- or 3- or 4-halophenyl, heteroalkyl, alkyl, aryl, arylalkyl, heteroaryl, heteroarylalkyl, cycloalkyl, cycloalkylalkyl, heterocyclyl, and heterocyclylalkyl;

wherein $R^3$ is selected from —B($R^4R^5$), —$R^6$—B($R^4R^5$), $R^6$, —C(O)—$R^6$, —O—$R^6$, —S(O)$_y$—$R^6$ (wherein y=0, 1, or 2), —P(O)—($R^4R^5$) and —N($R^7R^8$);

wherein $R^4$ and $R^5$ are independently hydrogen, hydroxyl, aryloxy, or alkoxy, or wherein $R^4$ and $R^5$ together form a cyclic ester, or an acid anhydride (either mixed or symmetrical);

wherein $R^6$ is selected from alkyl, aryl, arylalkyl, cycloalkyl, heteroaryl, heteroarylalkyl, heterocyclyl and heterocyclylalkyl;

wherein $R^7$ and $R^8$ are independently selected from hydrogen, alkyl, haloalkyl, aryl, cycloalkyl, arylalkyl, heteroalkyl, heterocyclyl and heterocyclylalkyl; $R^7$ and $R^8$ are both oxygen to form a nitro group; or $R^7$ and $R^8$ together with the nitrogen to which they are attached, form a heterocyclyl; and wherein $R^9$ is selected from the group consisting of hydrogen, heteroalkyl, alkyl, aminoalkyl, aryl, arylalkyl, carboxyalkyl, heteroaryl, heteroarylalkyl, cycloalkyl, cycloalkylalkyl, heterocyclyl, and heterocyclylalkyl; or —B($R^4R^5$),—$BF_3^-M^+$, —$R^6$—B ($R^4R^5$), —$R^6$—$BF_3^-M^+$, $R^6$, —C(O)—$R^6$, —O—$R^6$, —S(O)$_y$—$R^6$ (wherein y=0, 1, or 2), —P(O)—($R^4R^5$) and —N($R^7R^8$); or an ionizing group selected from the group consisting of carboxylates, amines, phosphonates, and phosphates;

wherein $X^1$ is carbon or nitrogen; $X^2$ is —S(O)$_y$— (wherein y=0, 1, or 2), —N($R^9$)—, or oxygen; and n is an integer between 0 and 8;

or a pharmaceutically suitable solvate or salt thereof.

Figure 1B:
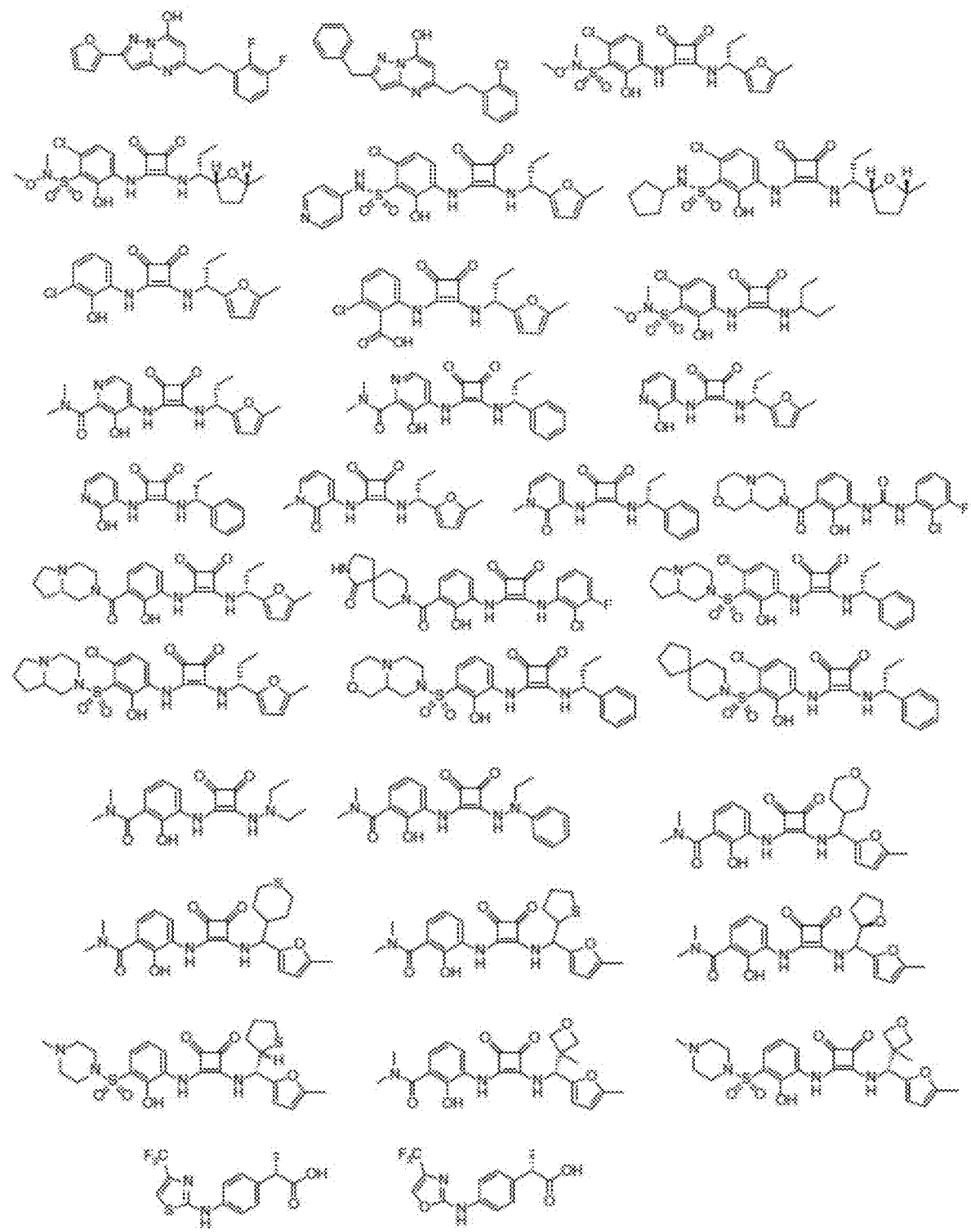
FIG. 1B shows structural formulas of CXCR1 and/or CXCR2 receptor antagonists.
Figure 1C:
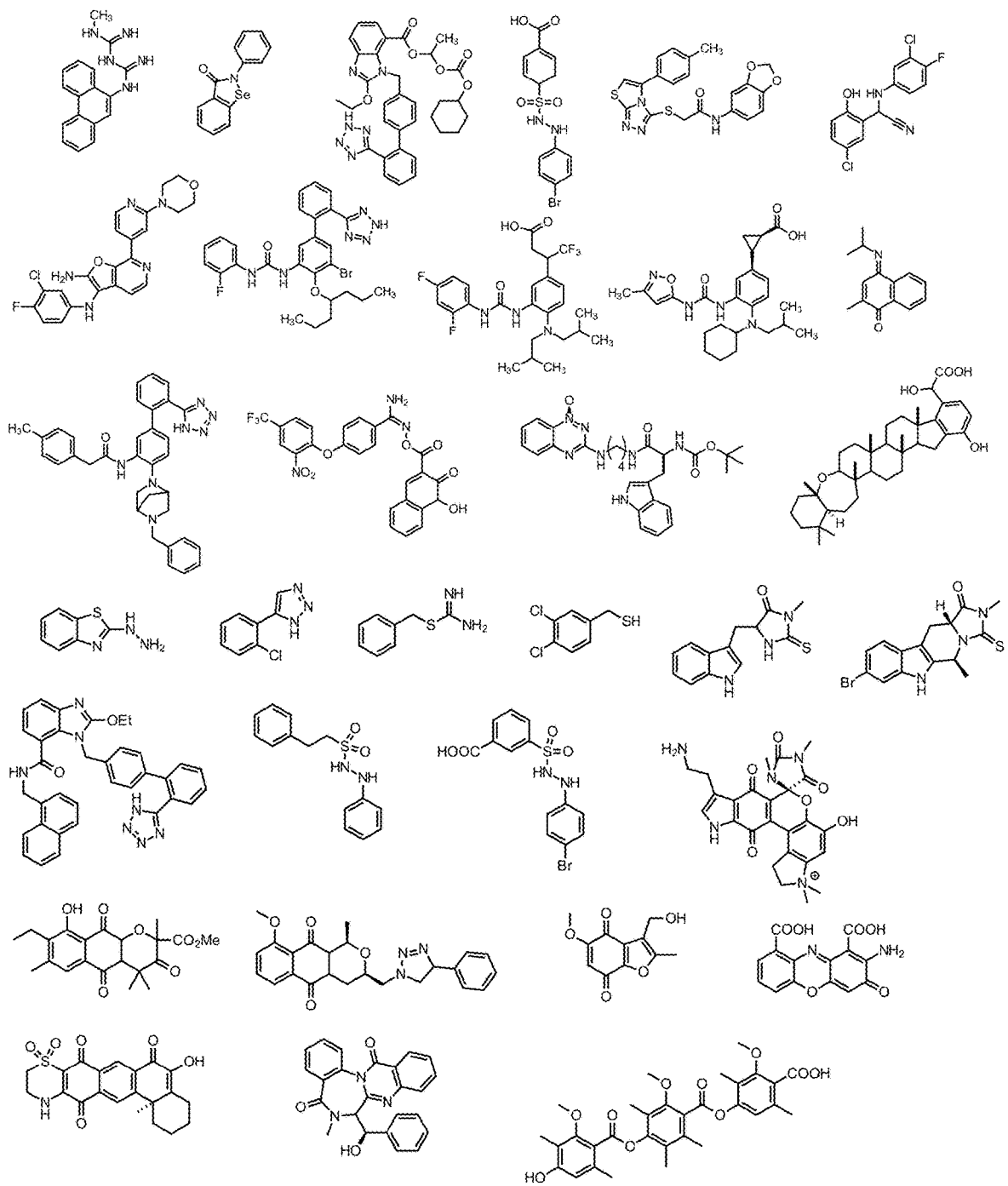
FIG. 1C shows structural formulas of immunotherapeutic compounds consisting of inhibitors of indoleamine 2,3-dioxygenase (IDO) or tryptophan 2,3-dioxygenase (TDO).

In one embodiment, the method of treating cancer in a subject in need of such treatment, wherein the pharmaceutical composition comprises a therapeutically effective amount of a compound selected from the group consisting of formulas SX-517, SX-520, SX-557, SX-574, SX-577, SX-603, SX-622, SX-660, SX-662, SX-671, SX-677, SX-678, and SX-682, shown in FIG. 1.

In another embodiment, the method of treating cancer in a subject in need of such treatment, comprising administering to the patient a therapeutically effective amount of at least one CXCR1 and/or CXCR2 receptor antagonist of formula II:

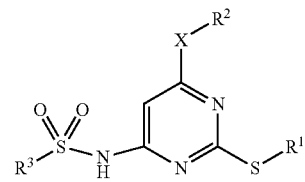

Functional groups are as defined in WO2006024823A9 (herein incorporated by reference). A representative antagonist from this genus is N-[2-[[(2,3-difluorophenyl)methyl]thio]-6-{[(1R,2S)-2,3-dihydroxy-1-methylpropyl]oxy}-4-pyrimidinyl]-1-azetidinesulfonamide (AZD5069)

In another embodiment, the method of treating cancer in a subject in need of such treatment, comprising administering to the patient a therapeutically effective amount of at least one CXCR1 and/or CXCR2 receptor antagonist of formula III:

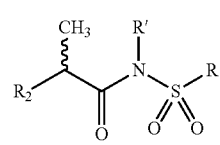

Functional groups are as defined in EP1123276B1 (herein incorporated by reference). A representative antagonist from this genus is (2R)-2-[4-(2-methylpropyl)phenyl]-N-methyl-sulfonylpropanamide (reparixin).

In another embodiment, the method of treating cancer in a subject in need of such treatment, comprising administering to the patient a therapeutically effective amount of at least one CXCR1 and/or CXCR2 receptor antagonist of formula IV:

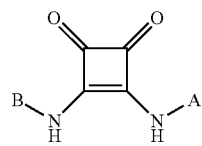

IV

Functional groups are as defined in U.S. Pat. No. 7,132,445B2 (herein incorporated by reference). A representative antagonist from this genus is 2-hydroxy-N,N-dimethyl-3-[[2-[[(1R)-1-(5-methylfuran-2-yl)propyl] amino]-3,4-dioxo-cyclobuten-1-yl]amino]benzamide (SCH527123, navarixin).

In another embodiment, the method of treating cancer in a subject in need of such treatment, comprising administering to the patient a therapeutically effective amount of at least one CXCR1 and/or CXCR2 receptor antagonist of formula V:

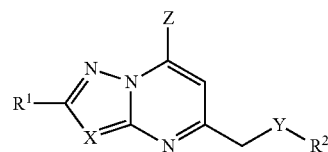

V

Functional groups are as defined in WO2009106539A1 (herein incorporated by reference).

In another embodiment, the method of treating cancer in a subject in need of such treatment, comprising administering to the patient a therapeutically effective amount of at least one CXCR1 and/or CXCR2 receptor antagonist of formula VI:

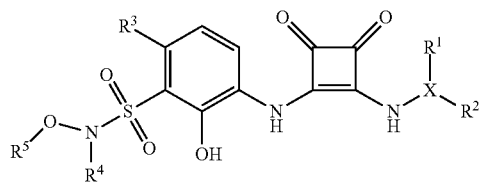

VI

Functional groups are as defined in WO2010015613A1 (herein incorporated by reference).

In another embodiment, the method of treating cancer in a subject in need of such treatment, comprising administering to the patient a therapeutically effective amount of at least one CXCR1 and/or CXCR2 receptor antagonist of formula VII:

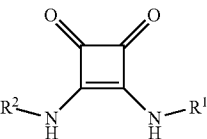

VII

Functional groups are as defined in WO2010131145A1, WO2010131146A1, and WO2010131147A (herein incorporated by reference).

In another embodiment, the method of treating cancer in a subject in need of such treatment, comprising administering to the patient a therapeutically effective amount of at least one CXCR1 and/or CXCR2 receptor antagonist of formula VIII:

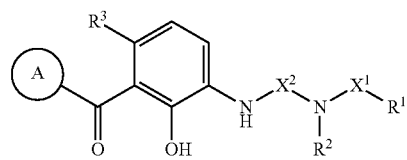

VIII

Functional groups are as defined in WO2012080456A1, the contents of which are herein incorporated by reference.

In another embodiment, the method of treating cancer in a subject in need of such treatment, comprising administering to the patient a therapeutically effective amount of at least one CXCR1 and/or CXCR2 receptor antagonist of formula IX:

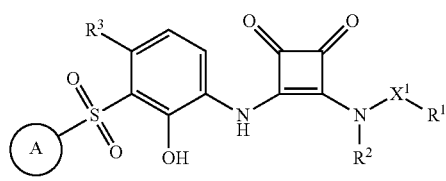

IX

Functional groups are as defined in WO2012080457A1 (herein incorporated by reference).

In another embodiment, the method of treating cancer in a subject in need of such treatment, comprising administering to the patient a therapeutically effective amount of at least one CXCR1 and/or CXCR2 receptor antagonist of formula X:

X

Functional groups are as defined in WO2010091543A1 (herein incorporated by reference).

In another embodiment, the method of treating cancer in a subject in need of such treatment, comprising administering to the patient a therapeutically effective amount of at least one CXCR1 and/or CXCR2 receptor antagonist of formula XI:

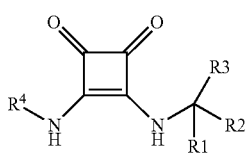

Functional groups are as defined in WO2013061002A1, WO2013061004A1, and WO2013061005A1 (herein incorporated by reference). Representative compounds include 1/2-hydroxy-N,N-dimethyl-3-(2-{[(5-methylfuran-2-yl)-(tetrahydropyran-4-yl)methyl]amino}-3,4-dioxocyclobut-1-enylamino)benzamide, 2/2-hydroxy-N,N-dimethyl-3-(2-{[(5-methylfuran-2-yl)-(tetrahydrothiopyran-4-yl)methyl]amino}-3,4-dioxocyclobut-1-enylamino)benzamide, 3/tert-butyl 4-[[2-(3-dimethylcarbamoyl-2-hydroxyphenylamino)-3,4-dioxocyclobut-1-enylamino]-(5-methylfuran-2-yl)methyl]piperidine-1-carboxylate, 4/benzyl 4-[[2-(3-dimethylcarbamoyl-2-hydroxyphenylamino)-3,4-dioxocyclobut-1-enylamino]-(5-methylfuran-2-yl)methyl]piperidine-1-carboxylate, 5/tert-butyl 3-[[2-(3-dimethylcarbamoyl-2-hydroxyphenylamino)-3,4-dioxocyclobut-1-enylamino]-(5-methylfuran-2-yl)methyl]piperidine-1-carboxylate, and 6/2-hydroxy-N,N-dimethyl-3-(2-{[(5-methylfuran-2-yl)-(4-methyltetrahydropyran-4-yl)methyl]amino}-3,4-dioxocyclobut-1-enylamino)benzamide.

In another embodiment, the method of treating cancer in a subject in need of such treatment, comprising administering to the patient a therapeutically effective amount of at least one CXCR1 and/or CXCR2 receptor antagonist of formula XII:

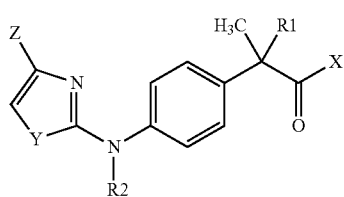

Functional groups are as defined in WO2010031835A2 (herein incorporated by reference). A representative molecule of this genus is (2S)—N-[(1S)-2-amino-1-methyl-2-oxoethyl]-2-(4-{[4-(trifluoromethyl)-1,3-oxazol-2-yl]amino}phenyl)propanamide.

In another embodiment, the method of treating cancer in a subject in need of such treatment, comprising administering to the patient a therapeutically effective amount of at least one CXCR1 and/or CXCR2 receptor antagonist of formula XIII:

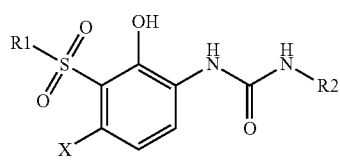

Functional groups are as defined in WO2007124424A2, the contents of which are herein incorporated by reference.

A representative antagonist from this genus is N-(4-chloro-2-hydroxy-3-(3-piperidinylsulfonyl)phenyl)-N'-(3-fluoro-2-methylphenyl)urea (GSK1325756, danirixin).

Another embodiment of the description is a method of treating a cancer patient by administering to the patient a therapeutically effective amount of a CXCR1 and/or CXCR2 receptor antagonist selected from the group consisting of HuMax-IL8 monoclonal antibody, navarixin (SCH-527123), danirixin (GSK-1325756), reparixin, AZD-5069, AZD-8309, elubrixin (SB-656933), ladarixin, SB-225002, SB-265610, SB-332235, SCH-563705 and compounds with the following formulas:

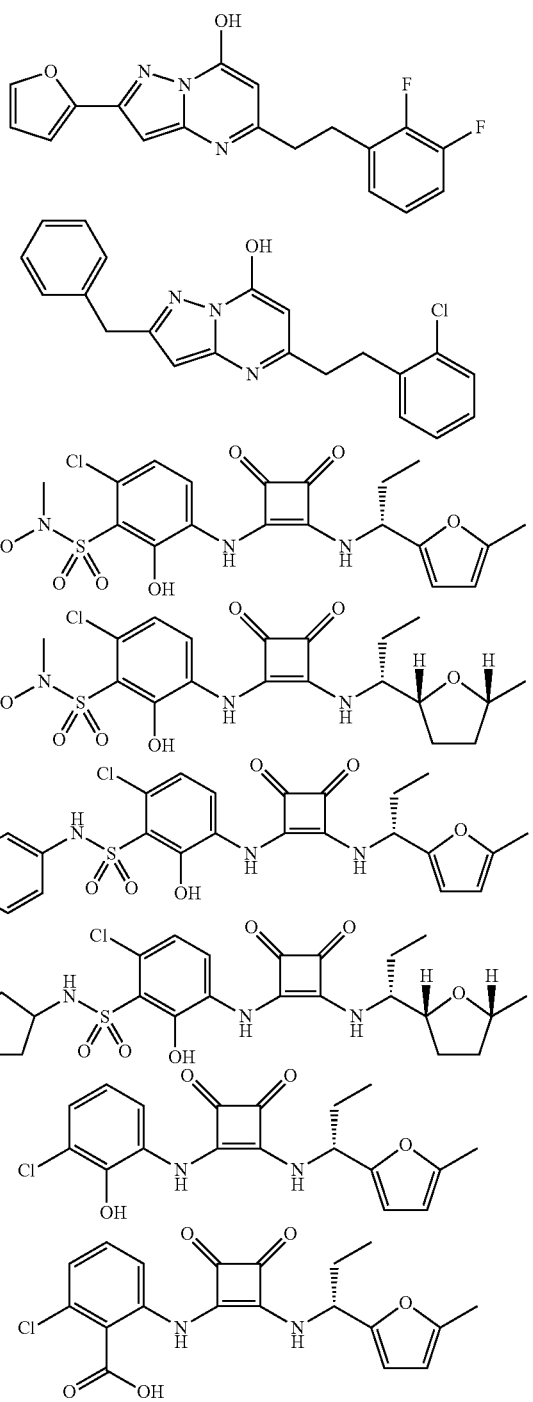

23
-continued
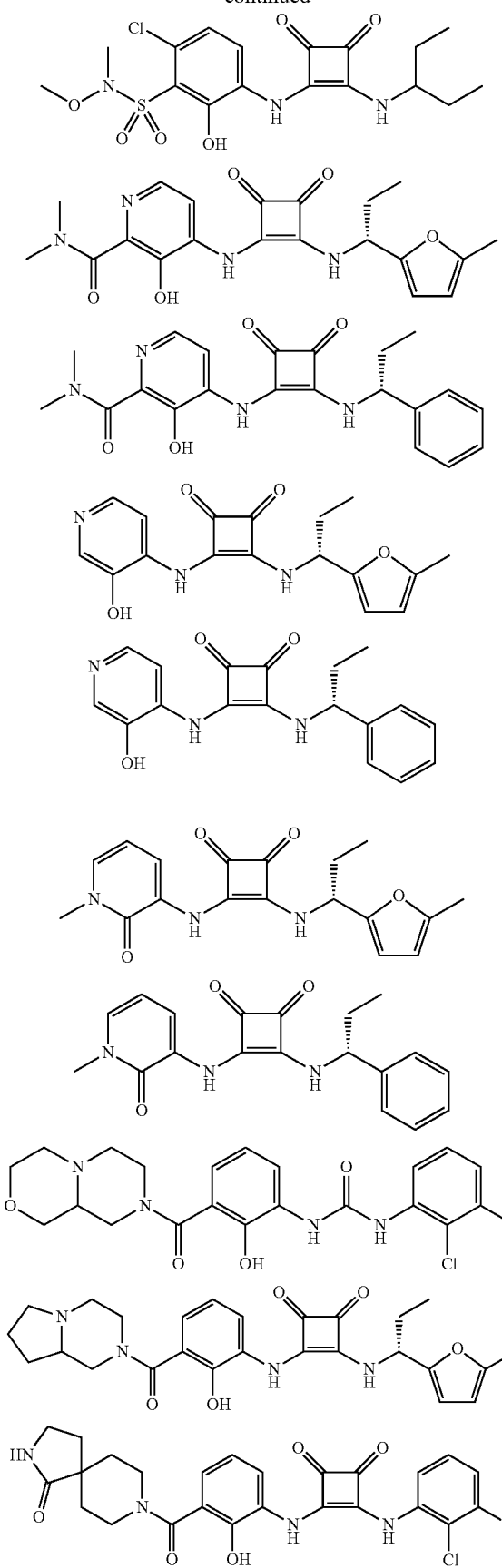
24
-continued
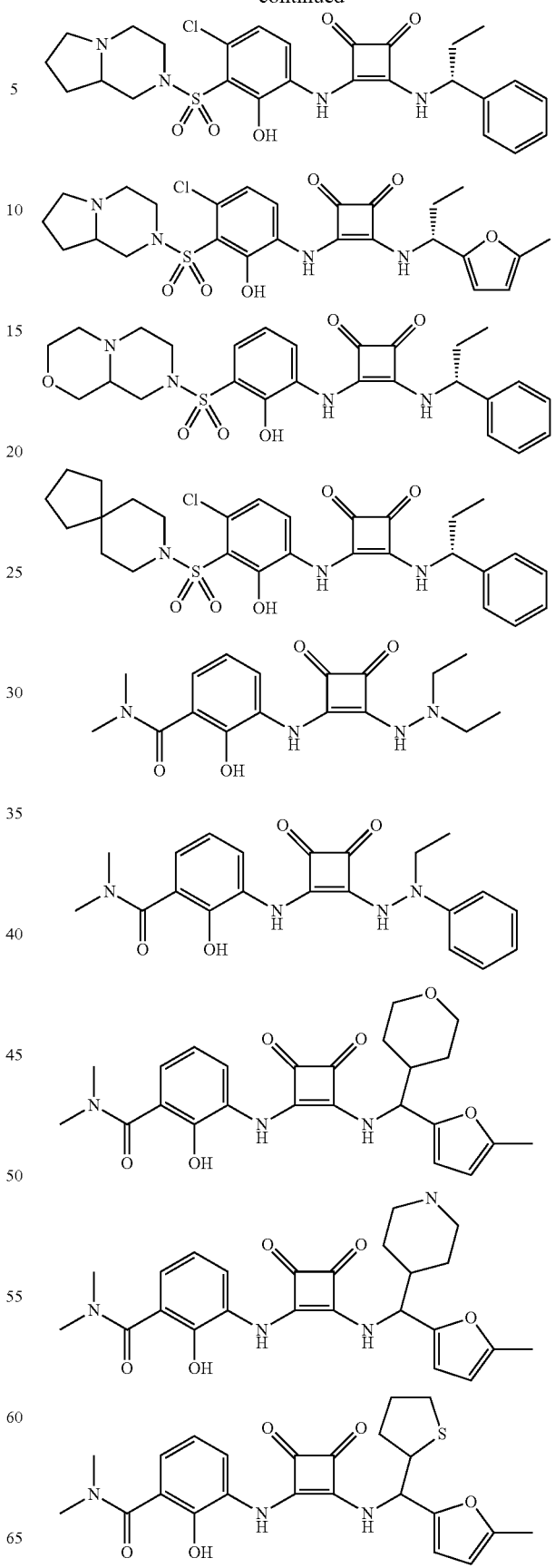

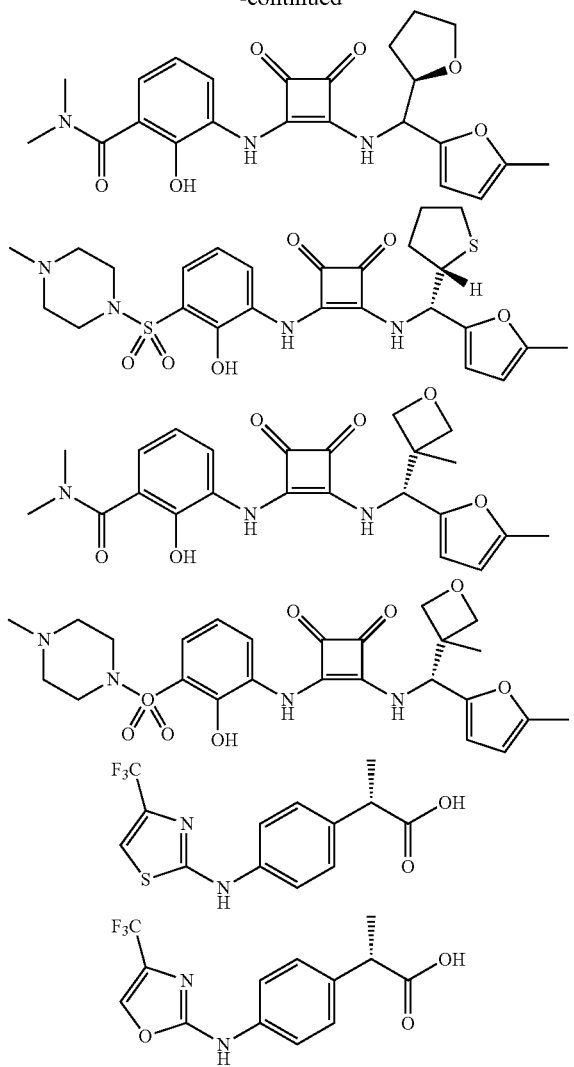

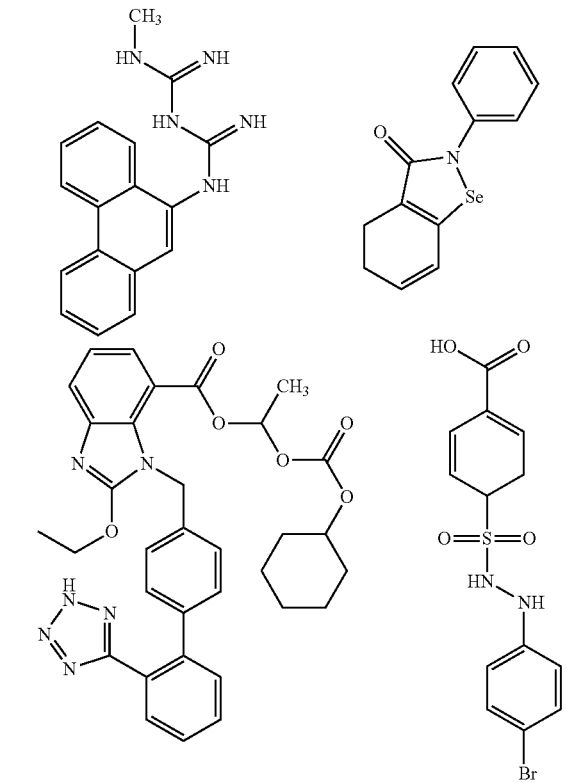

ICOS-L, OX40, OX40L, GITR, GITRL, CD70, CD27, CD40, DR3 and CD2; or an antibody that binds to a ligand of a regulatory receptor on NK cells. The immunotherapy may consist of antibody G7155 or FPA-008. The immunotherapy may consists of an agonistic agents that ligate positive costimulatory receptors, blocking agents that attenuate signaling through inhibitory receptors, antagonists, that increase systemically the frequency of anti-tumor T cells, agents that overcome distinct immune suppressive pathways within the tumor microenvironment), deplete or inhibit Tregs, or reverse/prevent T cell anergy or exhaustion, and agents that trigger innate immune activation and/or inflammation at tumor sites. The immunotherapy consists an antagonistic CTLA-4 antibody selected from ipilimumab or tremelimumab. The immunotherapy may consist of an antagonistic PD-1 or PD-L1 antibody selected from the group consisting of nivolumab, pembrolizumab, lambrolizumab, MEDI-0680, pidilizumab, AMP-224, atezolizomab, MPDL3280A, durvalumab, BMS-936559, and MSB0010718C. The immunotherapy may consist of a LAG-3 antagonist antibody selected from the group consisting of BMS-986016, IMP-731, and IMP-321. The immunotherapy may consist of a CD137 (4-IBB) antibody selected from urelumab and PF-05082566. The immunotherapy may consist of an agonistic GITR antibody selected from the group consisting of BMS-986153, BMS-986156, TRX-518 and MK-4166. The immunotherapy may consist of an agonistic OX40 antibody selected from the group consisting of MEDI-6383 or MEDI-6469.

Another embodiment is a method of treating a cancer patient by administering an immunotherapy consisting of an IDO and/or TDO inhibitor selected from the group consisting of indoximod, GDC-0919, F001287, GDC-0919 (NLG919), F001287, epacadostat (1NCB024360), IDO-IN-1, IDO-IN-2, navoximod (IDO-IN-7), and molecules with the following structures:

The immunotherapy may consists of antibody directed to a ligand to a T cell receptor, wherein the immunotherapy amplifies antigen-specific T cell responses, e.g., a ligand selected from the group consisting of B7-1, B7-2, B7-H1 (PD-L1), B7-DC (PD-L2), B7-H2 (ICOS-L), B7-H3, B7-H4, B7-H5 (VISTA), and B7-H6. The ligand may be selected from CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, lymphotoxin α/TNFβ, TNFR2, TNFα, LTβR, lymphotoxin α1β2, FAS, FASL, RELT, DR6, TROY, and NGFR. The ligand may be selected from IL-6, IL-10, TGF-β, VEGF.

Another embodiment is a method of treating a cancer patient by administering an immunotherapy consisting of an antibody that binds to a checkpoint inhibitor selected from the group consisting of CTLA-4, PD-1, PD-L1, PD-L2, LAG-3, TIM-3, galectin 9, CEACAM-1, BTLA, CD69, galectin-1, TIGIT, CD113, GPR56, VISTA, 2B4, CD48, GARP, PD1H, LAIR1, TIM-1, and TIM-4. The immunotherapy may alternatively consist of an antibody that binds to an agonist of a protein selected from the group consisting of B7-1, B7-2, CD28, 4-1BB (CD137), 4-1BBL, ICOS, -continued
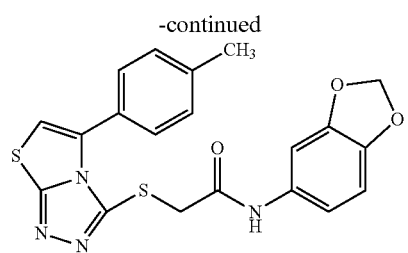
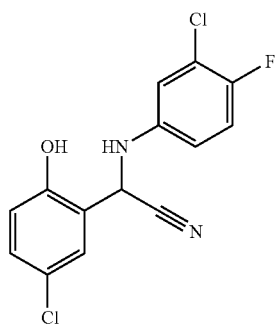
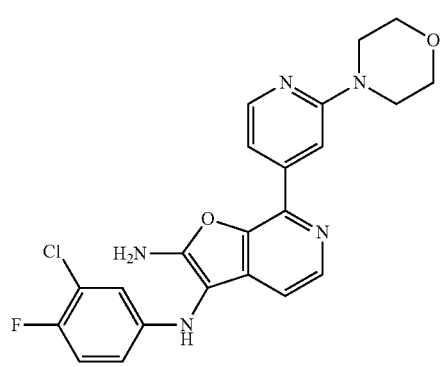
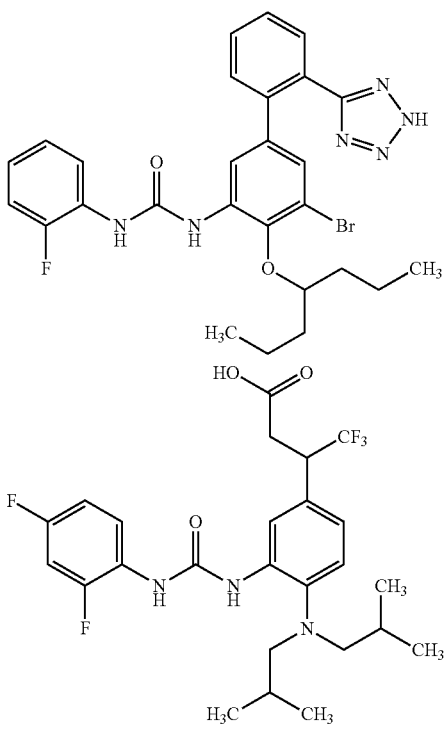
-continued
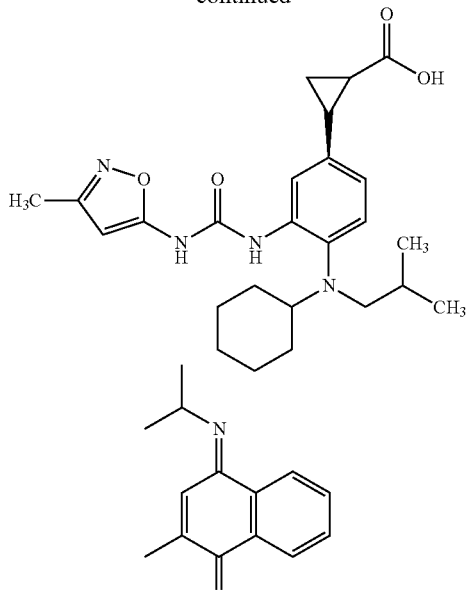
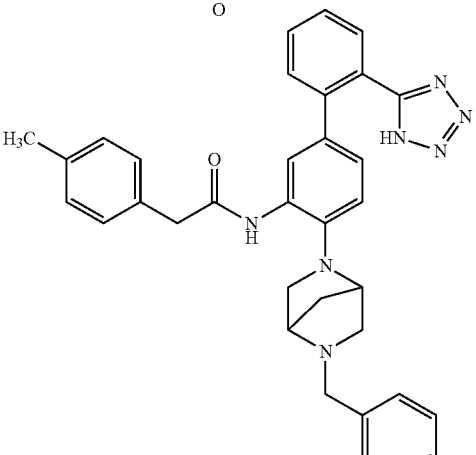
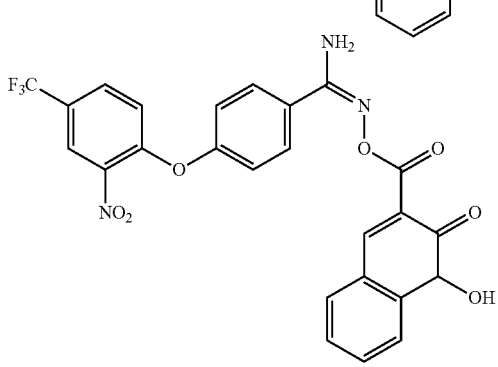
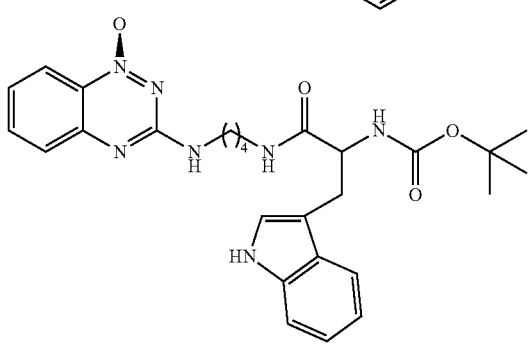

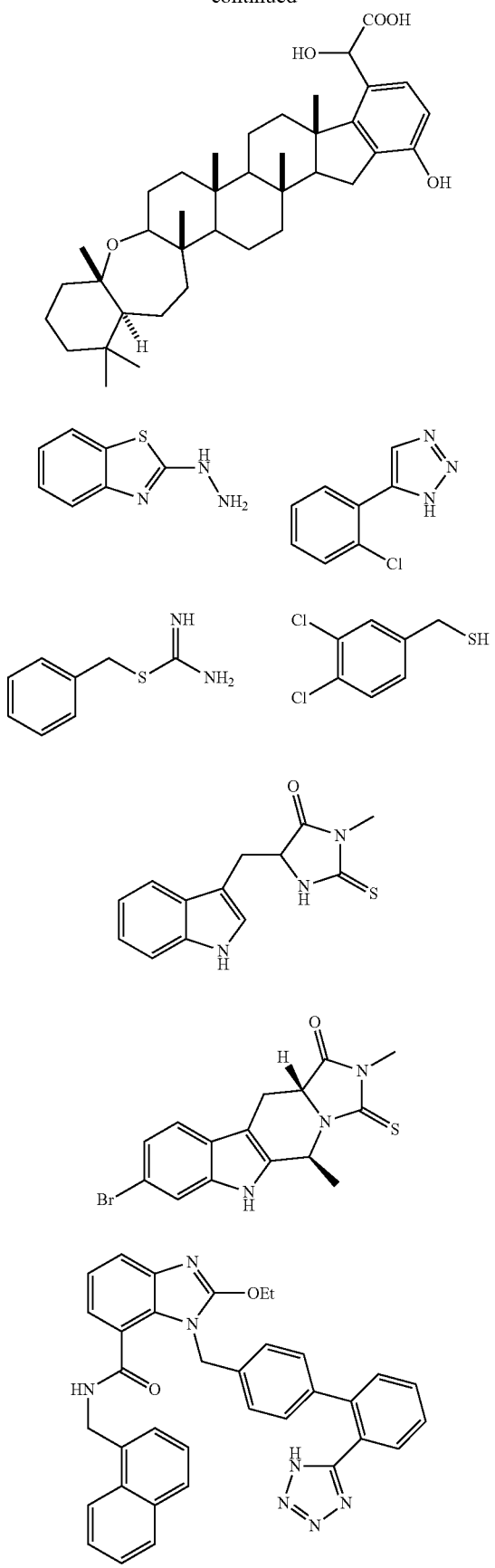
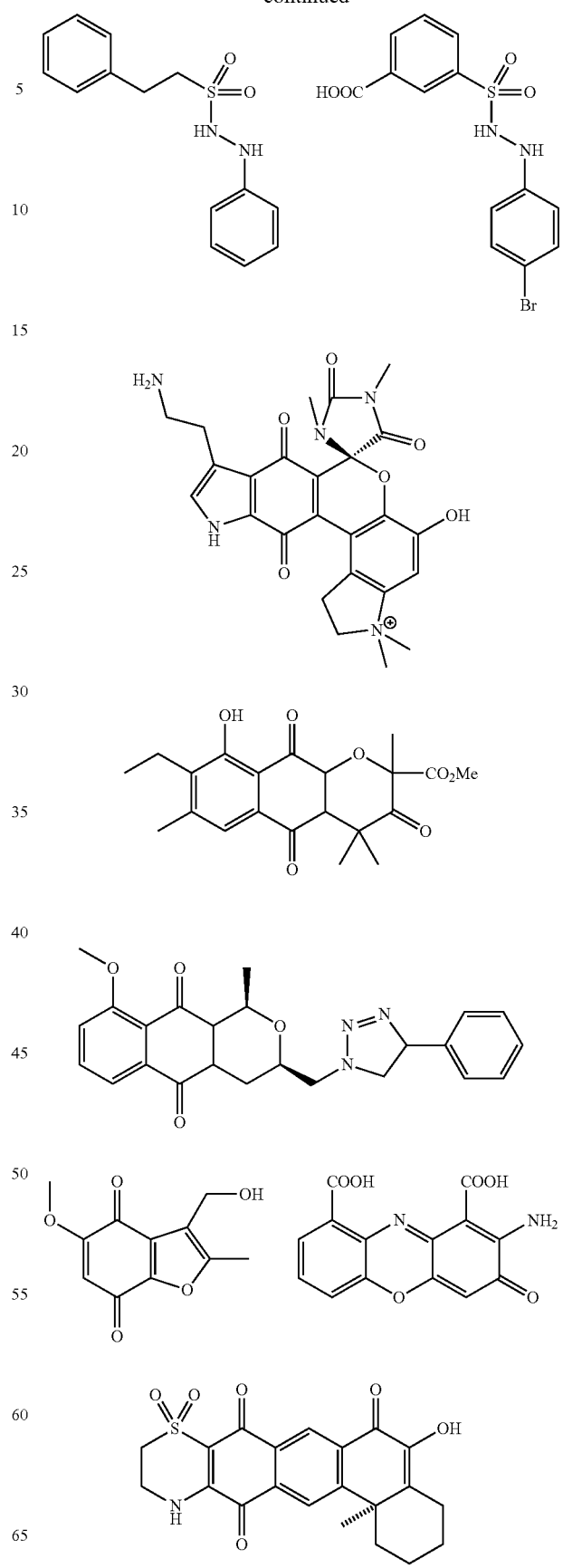

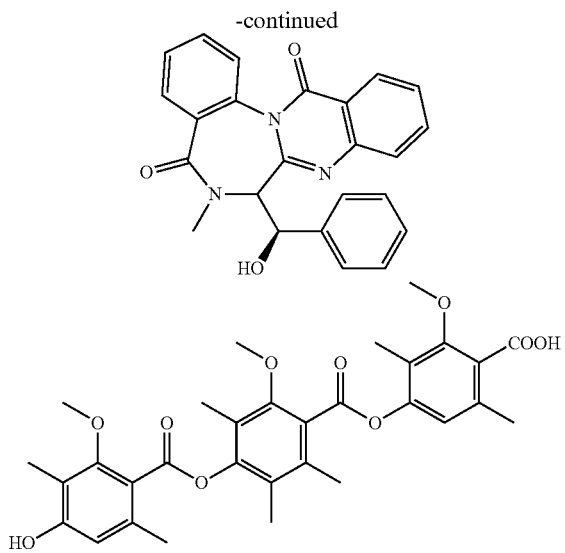

Another embodiment is a method of treating a cancer patient by administering an immunotherapy consisting of an antagonistic OX40 antibody consisting of RG-7888; an agonistic CD40 antibody consisting of lucatumumab or dacetuzumab; an agonistic CD27 antibody consisting of varlilumab; or MGA271.

In another embodiment, the method of treating cancer in a subject in need of such treatment, comprising administering to the patient a therapeutically effective amount of at least one CXCR1 and/or CXCR2 receptor antagonist comprising the CXCL8 ligand blocking antibody HuMax-IL8.

Cancer Indications

In accordance with the disclosure herein, an antagonist of CXCR1 and/or CXCR2 receptors can be used to treat a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), cancers of the lymphoid and hematopoietic system and the immune system (e.g., spleen, thymus, or bone marrow), virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, and metastasis. In particular embodiments, the tumor or cancer is pancreatic cancer, prostate cancer, colon cancer, ovarian cancer, breast cancer, melanoma, lung cancer, glioblastoma, or leukemia.

Combination Therapy

The disclosure herein contemplates the use of at least one antagonist of CXCR1 and/or CXCR2 receptors in combination with one or more anticancer therapy (e.g., chemotherapeutic agents, immune checkpoint inhibitors, T-cell therapy, cancer vaccines) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, at least one antagonist of CXCR1 and/or CXCR2 is administered or applied sequentially, e.g., where one agent is administered prior to one or more other agents. In other embodiments, at least one antagonist of CXCR1 and/or CXCR2 is administered simultaneously, e.g., where two or more agents are administered at or about the same time; the two or more agents may be present in two or more separate formulations or combined into a single formulation (i.e., a co-formulation). By way of example, the disclosure herein contemplates a treatment regimen wherein administration of an antagonist to CXCR1 and/or CXCR2 receptors is maintained on a daily basis, with additional anticancer treatments (e.g., anti-PD1 antibody, carboplatin, cancer vaccine, T-cell therapy, radiation) given intermittently during the treatment period. Regardless of whether the two or more agents are administered sequentially or simultaneously, they are considered to be administered in combination for purposes of the disclosure herein.

The disclosure herein provides methods for treating and/or preventing a proliferative condition, cancer, tumor, or precancerous disease, disorder or condition with at least one antagonist of CXCR1 and/or CXCR2 receptors and at least one additional anticancer therapy (e.g., chemotherapeutic agents, immune checkpoint inhibitors, T-cell therapy, cancer vaccines, immunomodulatory agent) or other prophylactic or therapeutic modalities (e.g., radiation). Suitable immunomodulatory agents that may be used in the disclosure herein include CD40L, B7, and B7RP1; activating monoclonal antibodies (mAbs) to stimulatory receptors, such as, ant-CD40, anti-CD38, anti-ICOS, and 4-IBB ligand; IDO and/or TDO inhibitors; anti-chemokine ligands; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); and immune-stimulatory oligonucleotides.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Chemotherapeutic agents also include signal transduction inhibitors (STI). The term "signal transduction inhibitor" refers to an agent that selectively inhibits one or more steps in a signaling pathway. Signal transduction inhibitors (STIs) of the disclosure herein include: (i) bcr/abl kinase inhibitors (e.g., GLEEVEC®); (ii) epidermal growth factor (EGF) receptor inhibitors, including kinase inhibitors and antibodies; (iii) her-2/neu receptor inhibitors (e.g., HERCEPTIN®); (iv) inhibitors of Akt family kinases or the Akt pathway (e.g., rapamycin); (v) cell cycle kinase inhibitors (e.g., flavopiridol); and (vi) phosphatidyl inositol kinase inhibitors.

Additional treatment modalities that may be used in combination with a antagonist of CXCR1 and/or CXCR2 receptors include a cytokine or cytokine antagonist, such as IL-12, IFN, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., a protein or a nucleic acid encoding the protein) are also provided herein.

Immune Checkpoint Inhibitors

The disclosure herein contemplates the use of at least one antagonist of CXCR1 and/or CXCR2 receptors in combination with additional immune checkpoint inhibitors.

Genetic and epigenetic alterations that are characteristic of all cancers provide a diverse set of antigens that the immune system can use to distinguish tumor cells from their normal counterparts. The response of T cells initiated through antigen recognition by the T-cell receptor (TCR) is regulated by a balance between co-stimulatory and inhibitory signals (immune checkpoints) that determine the ultimate amplitude (e.g., levels of cytokine production or proliferation) and quality (e.g., the type of immune response generated, such as the pattern of cytokine production) of the response. Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms. In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not overexpressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor-ligand immune checkpoints can be modulated using agonist antibodies (for co-stimulatory pathways) or antagonist antibodies (for inhibitory pathways).

The disclosure herein contemplates the use at least one antagonist of CXCR1 and/or CXCR2 receptors in combination with inhibitors of the aforementioned immune-checkpoint receptors and ligands, as well as immune-checkpoint enzymes. Certain modulators of immune checkpoints are currently available, e.g., CTLA4 monoclonal antibody ipilimumab (YERVOY®; Bristol-Myers Squibb); fusion proteins comprising CTLA4 and an antibody (CTLA4-Ig; abatacept (ORENCIA®; Bristol-Myers Squibb)); anti-PD-1 antibodies nivolumab (OPDIVO®, Bristol-Myers Squibb) and pembroluzimab (KEYTRUDA®, Merck); anti-PDL1 antibodies durvalumab (AstraZeneca/Medimmune), tremelimumab, pidilizumab, avelumab, and atezolizumab (MPDL3280A, Roche).

Inhibitors of the immune-checkpoint enzymes IDO and/or TDO include those described by Rohrig et al., and Qian et al., are incorporated here by reference (Rohrig, 2015, *J Med Chem,* 58:9421-37 and Qian, 2016, *RSC Adv,* 6:7575-81).

In one aspect of the disclosure herein, at least one antagonist of CXCR1 and/or CXCR2 receptors is combined with immunotherapy that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, lymphotoxin α/TNFβ, TNFR2, TNFα, LTβR, lymphotoxin α1β2, FAS, FASL, RELT, DR6, TROY, NGFR.

In another aspect, the immunotherapy is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of at least one antagonist of CXCR1 and/or CXCR2 receptors and one or more of (i) an antagonist of a protein that inhibits T cell activation (e.g., immune checkpoint inhibitors) such as CTLA-4, PD-1, PD-L1, PD-L2, LAG-3, TIM-3, galectin 9, CEACAM-1, BTLA, CD69, galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with at least one antagonist of CXCR1 and/or CXCR2 receptors for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF1R antagonists. Examples of CSF1R antagonists (herein incorporated by reference) are provided in: Cannarile, 2017, J Immunother Cancer, 5, 53; WO11/70024; WO11/107553; WO11/131407; WO13/87699; WO13/119716; WO13/132044; WO11/140249; WO13/169264; and WO14/036357. Examples of CSF1R antagonist antibodies include, for example, emactuzumab (RG7155), cabiralizumab (FPA-008), AMG820, IMC-CS4 (LY3022855), MCS110, SNDX-6352, and PD-0360324. Examples of CSF1R small molecule antagonists include, for example, pexidartinib (PLX3397, PLX108-01), PLX7486, ARRY-382, JNJ-40346527, BLZ945, and DCC-3014. Another aspect of macrophage and/or monocyte inhibition may involve blockade of CCR2 receptors. Examples of CCR2 antagonists (herein incorporated by reference) are provided in: Zimmerman, 2014 Curr Top Med Chem, 14, 1539-52; Struthers, 2010, Curr Top Med Chem, 10, 1278-98; and Xia, 2009, Expert Opin Ther Pat, 19, 295-303. Suitable CCR2 antagonists include, for example, CCX140-B, CCX872, CCX915, MLN1202, JNJ-17166864, JNJ-27141491, MK-0812, PF-04136309, PF-04634817, BMS-741672, 1NCB8696, INCB3284, INCB3344, NIBR-1282, NIBR-177, GSK-1344386B, CCR2-RA-R, RS504393, and cenicriviroc (TAK-652, TBR-652). The references listed are incorporated by reference in their entirety.

In another aspect, at least one antagonist of CXCR1 and/or CXCR2 receptors can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immunotherapy is a CTLA-4 antagonist, such as an antagonistic CTLA-4 antibody. Suitable CTLA-4 antibodies include, for example, YERVOY® (ipilimumab) or tremelimumab.

In another aspect, the immunotherapy is a PD-1 antagonist, such as an antagonistic PD-1 antibody. Suitable PD-1 antibodies include, for example, OPDIVO® (nivolumab), KEYTRUDA® (pembrolizumab/lambrolizumab), or MEDI-0680 (AMP-514; WO2012/145493). The immunotherapy may also include pidilizumab (CT-011). Another approach to target the PD-1 receptor is the recombinant protein composed of the extracellular domain of PD-L2 (B7-DC) fused to the Fc portion of IgG1, called AMP-224.

In another aspect, the immunotherapy is a PD-L1 antagonist, such as an antagonistic PD-L1 antibody. Suitable PD-L1 antibodies include, for example, TECENTRIQ™ (atezolizomab), MPDL3280A (RG7446; WO2010/077634), durvalumab (MEDI4736), BMS-936559 (WO2007/005874), and MSB0010718C (WO2013/79174).

In another aspect, the immunotherapy is a LAG-3 antagonist, such as an antagonistic LAG-3 antibody. Suitable LAG3 antibodies include, for example, BMS-986016 (WO10/19570, WO14/08218), or IMP-731 or IMP-321 (WO008/132601, WO009/44273).

In another aspect, the immunotherapy is a CD137 (4-IBB) agonist, such as an agonistic CD137 antibody. Suitable CD137 antibodies include, for example, urelumab and PF-05082566 (WO12/32433).

In another aspect, the immunotherapy is a GITR agonist, such as an agonistic GITR antibody. Suitable GITR antibodies include, for example, BMS-986153, BMS-986156, TRX-518 (WO006/105021, WO009/009116) and MK-4166 (WO11/028683).

In another aspect, the immunotherapy is an OX40 agonist, such as an agonistic OX40 antibody. Suitable OX40 antibodies include, for example, MEDI-6383 or MEDI-6469.

In another aspect, the immunotherapy is an OX40L antagonist, such as an antagonistic OX40 antibody. Suitable OX40L antagonists include, for example, RG-7888 (WO06/029879).

In another aspect, the immunotherapy is a CD40 agonist, such as an agonistic CD40 antibody. In yet another embodiment, the immunotherapy is a CD40 antagonist, such as an antagonistic CD40 antibody. Suitable CD40 antibodies include, e.g., lucatumumab or dacetuzumab.

In another aspect, the immunotherapy is a CD27 agonist, such as an agonistic CD27 antibody. Suitable CD27 antibodies include, e.g., varlilumab.

In another aspect, the immunotherapy is MGA271 (to B7H3) (WO11/109400).

The disclosure herein encompasses pharmaceutically acceptable salts, acids or derivatives of any of the above.

Pharmaceutical Compositions

Compounds of formula I may be in the form of compositions suitable for administration to a subject. In general, such compositions are "pharmaceutical compositions" comprising at least one compound of formula I and one or more pharmaceutically acceptable or physiologically acceptable diluents, carriers or excipients. In certain embodiments, compounds of formula I are present in a therapeutically acceptable amount. The pharmaceutical compositions may be used in the methods of the disclosure herein; thus, for example, the pharmaceutical compositions can be administered ex vivo or in vivo to a subject in order to practice the therapeutic and prophylactic methods and uses described herein.

The pharmaceutical compositions of the disclosure herein can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the disclosure herein.

The pharmaceutical compositions containing the active ingredient (e.g., compound of formula I) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc.

The pharmaceutical compositions containing the active ingredient (e.g., compound of formula I) may be prepared by spray dry co-dispersion with a suitable polymer, such as hypromellose phthalate (HPMCP), hypromellose acetate succinate (HPMCAS), polyvinyl acetate phthalate (PVAP), ENCAPSIA®, EUDRAGIT® L100-55, OPADRY®, and DEXOLVE®.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example, peanut oil, liquid paraffin, or olive oil. Liquid form preparations may also include dissolution in lipid-based, self-emulsifying drug delivery systems (SEDDS) such as LABRASOL® or GELUCIRE® for oral administration.

Aqueous suspensions contain the active materials in admixture with excipients suitable for the manufacture thereof. Such excipients can be suspending agents, for example, sodium carboxymethylcellulose, methylcellulose, hydroxy-propylmethylcellulose, sodium alginate, polyvinylpyrrolidone, gum tragacanth and gum acacia; dispersing or wetting agents, for example, a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the disclosure herein may include techniques to improve the solubility of the active ingredient to increase oral bioavailability. These techniques include, but are not limited to: physical modification of the active ingredient through particle size reduction through either comminution and spray drying, or micronization through milling techniques; solid dispersion techniques such as hot melt fusion, solvent evaporation method, and hot melt extrusion; preparation of a nanosuspension of the active ingredient through either the precipitation technique, media milling, high-pressure homogenization in water, high pressure homogenization in nonaqueous media, or combinations of techniques thereof; preparation of micronized drug particles via supercritical fluid processes; preparation of nanostructured amorphous drug particles through spray freezing onto cryogenic fluids, spray freezing into cryogenic liquids, spray freezing into vapor over liquid, and ultra-rapid freezing; preparation of an inclusion complex with cyclodextrins via kneading, lyophilization, or microwave irradiation techniques; and micellular solubilization of the active ingredient using surfactants. These methods are described in greater detail in Savjani, 2012, *ISRN Pharm,* 2012:195727 (herein incorporated by reference).

The pharmaceutical compositions of the disclosure herein may also be in the form of oil-in-water emulsions. The oily phase may be a vegetable oil, for example, olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions of the disclosure herein may also be in the form useful for direct introduction to the lungs via aerosol delivery. An aerosol formulation of the disclosure herein also comprises a propellant. Suitable propellants include conventional chlorofluorocarbon (CFC) propellants such as mixtures of propellants 11, 12, and 114. Non-CFC propellants, particularly 1,1,1,2-tetrafluoroethane (Propellant 134a), 1,1,1,2,3,3,3-heptafluoropropane (Propellant 227), or mixtures thereof, are preferred. The propellant is preferably present in an amount sufficient to propel a plurality of doses of drug from an aerosol canister. Further components, such as conventional lubricants or surfactants, cosolvents (e.g., ethanol), and the like, can also be present in an aerosol formulation of the disclosure herein in suitable amounts readily determined by those skilled in the art.

The pharmaceutical compositions of the disclosure herein may also be in the form useful for direct introduction to the lungs via dry powder inhalation delivery. A dry powder formulation of the disclosure herein would comprise the active ingredient (e.g., antagonist of CXCR1 and/or CXCR2 receptors) formulated with a carrier compatible with pulmonary delivery. Selecting an excipient as a carrier is an important factor in the composition of an inhalation formulation. Examples of the excipient employable for the disclosure herein include monosaccharides such as glucose, arabinose; disaccharides such as lactose, maltose, sucrose; polysaccharides such as starch, dextrin or dextran; polyalcohols such as sorbitol, mannitol, and xylitol; and hydrates thereof.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The pharmaceutical compositions typically comprise a therapeutically effective amount of at least one antagonist of CXCR1 and/or CXCR2 receptors and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a TRIS buffer, N-(2-hydroxyethyl)piperazine-N'-(2-ethanesulfonic acid) (HEPES), 2-(N-morpholino)ethanesulfonic acid (MES), 2-(N-morpholino)ethanesulfonic acid sodium salt (MES), 3-(N-morpholino)propanesulfonic acid (MOPS), and N-tris[hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (e.g., EPIPEN®)), whereas a multi-use container (e.g., a multi-use vial) is provided in other embodiments. Any drug delivery apparatus may be used to deliver compounds of formula I, including implants (e.g., implantable pumps) and catheter systems, slow injection pumps and devices, all of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, CREMOPHOR® EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of an injectable formulation. Prolonged absorption of particular injectable formulations can be achieved by including an agent that delays absorption (e.g., aluminum monostearate or gelatin).

The disclosure herein contemplates the administration of compounds of formula I in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

Routes of Administration

The disclosure herein contemplates the administration of compounds of formula I, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), sublingual and inhalation. Depot injections, which are generally administered subcutaneously or intramuscularly, may also be utilized to release the compounds of formula I or formula II disclosed herein over a defined period of time.

Dosing

Compounds of formula I may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

For administration of an oral agent, the compositions can be provided in the form of tablets, capsules and the like containing from 1.0 to 1000 milligrams (mg) of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient.

In certain embodiments, the dosage of the desired antagonist of CXCR1 and/or CXCR2 is contained in a "unit dosage form". The phrase "unit dosage form" refers to physically discrete units, each unit containing a predetermined amount of at least one antagonist of CXCR1 and/or CXCR2, either alone or in combination with one or more additional agents, sufficient to produce the desired effect. It will be appreciated that the parameters of a unit dosage form will depend on the particular agent and the effect to be achieved.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the disclosure herein and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

The amount and frequency of administration of the compounds of formula I and the chemotherapeutic agents, immunotherapy, and/or radiation therapy will be regulated according to the judgment of the attending clinician (physician) considering such factors as age, condition and size of the patient as well as severity of the disease being treated. A dosage regimen of the antagonist of CXCR1 and/or CXCR2 can be oral administration of from 10 mg to 2000 mg/day, or 10 to 1000 mg/day, or 50 to 600 mg/day, in two to four (or two) divided doses, to block tumor growth. Intermittent therapy (e.g., one week out of three weeks or three out of four weeks) may also be used.

The chemotherapeutic agent, immunotherapy, and/or radiation therapy can be administered according to therapeutic protocols well known in the art. It will be apparent to those skilled in the art that the administration of the chemotherapeutic agent, immunotherapy and/or radiation therapy can be varied depending on the disease being treated and the known effects of the chemotherapeutic agent, immunotherapy, and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., chemotherapy, immunotherapy, or radiation) on the patient, and in view of the observed responses of the disease to the administered therapeutic agents.

If the antagonist of CXCR1 and/or CXCR2, and the chemotherapeutic agent, immunotherapy, and/or radiation is not administered simultaneously or essentially simultaneously, then the initial order of administration of the antagonist of CXCR1 and/or CXCR2, and the chemotherapeutic agent and/or radiation, may not be important. Thus, the antagonist of CXCR1 and/or CXCR2 may be administered first, followed by the administration of the chemotherapeutic agent and/or radiation; or the chemotherapeutic agent and/or radiation may be administered first, followed by the administration of the antagonist of CXCR1 and/or CXCR2. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

For example, the chemotherapeutic agent, immunotherapy, and/or radiation may be administered first, especially if it is a cytotoxic agent, and then the treatment continued with the administration of the antagonist of CXCR1 and/or CXCR2 followed, where determined advantageous, by the administration of the chemotherapeutic agent, immunotherapy, and/or radiation, and so on until the treatment protocol is complete.

By way of example, the disclosure herein contemplates a treatment regimen wherein administration of an antagonist to CXCR1 and/or CXCR2 receptors is maintained on a daily basis, with additional anticancer treatments (e.g., anti-PD1 antibody, carboplatin, T-cell therapy, cancer vaccination, radiation) given intermittently during the treatment period.

The particular choice of a compound from formula I, and chemotherapeutic agent, immunotherapy, and/or radiation will depend upon the diagnosis of the attending physicians and their judgment of the condition of the patient and the appropriate treatment protocol.

Also, in general, the antagonist of CXCR1 and/or CXCR2 and the chemotherapeutic agent and/or immunotherapy do not have to be administered in the same pharmaceutical composition, and may, because of different physical and chemical characteristics, have to be administered by different routes. For example, the antagonist of CXCR1 and/or CXCR2 may be administered orally to generate and maintain good blood levels thereof, while the chemotherapeutic agent and/or immunotherapy may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Thus, in accordance with experience and knowledge, the practicing physician can modify each protocol for the administration of a component (therapeutic agent; i.e., the compound from formula I, chemotherapeutic agent, immunotherapy or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

EXAMPLES

Aspects of the present teachings may be further understood in light of the following examples, which should not be construed as limiting the scope of the present teachings in any way.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Formulation Example 1: Spray Dry Dispersion (SDD) of SX-682 onto Hypromellose Phthalate (HPMCP)

An alternative method to increase oral bioavailability of drug products is through spray dry dispersion in a polymer carrier matrix, which utilizes the spray drying of the active pharmaceutical ingredient (API) and polymer in an organic solvent. Upon drying, the API is amorphously dispersed in the polymer matrix. The polymer matrix is water soluble, and allows for the slow release of API upon exposure to aqueous environments. Spray dry dispersion was performed at Emerson Resources (Norristown, Pa.). SX-682 (250 g) was first dissolved in acetone/water (97:3, 10 liters). HPMCP, 750 g, was then added. The in-process control is to check the clarity of the feed solution and report the result. The material is then spray dried using a GEA Mobile Minor spray dryer using nitrogen as the drying gas. The inlet temperature is set at 90° C., and the outlet temperature is 55-60° C. The nozzle size used was 1 mm. The SX-682 spray solution concentration is 10%, and the atomization nitrogen was set at 1.8 bar, 50%. The formulated powder is collected from both the cyclone and the cartridge filter and post-dried. The powder is bag-blended and double bagged with dessicant pouches for storage. The spray-dried dispersion was suspended in aqueous 0.5% methylcellulose (400 cps) prior to oral dosing in preclinical models.

Pharmacology Example 1: Inhibition of MDSC Migration

A large body of evidence indicates that chronic inflammation as occurs in inflammatory bowel disease is one of several key risk factors for cancer initiation, progression, and metastasis. In an azoxymethane/dextran sulfate sodium (AOM/DSS) model of colitis-associated cancer, Katoh, 2013, *Cancer Cell*, 24:631-44, presented genetic evidence (Cxcr2$^{-/-}$) that loss of CXCR2 dramatically suppressed chronic colonic inflammation and colitis-associated tumorigenesis by inhibiting MDSC recruitment into colonic mucosa and tumors. CXCR2 ligands CXCL1, CXCL2 and CXCL5 were all elevated in inflamed colonic mucosa and tumors and induced MDSC chemotaxis. Adoptive transfer of wild-type MDSCs into Cxcr2$^{-/-}$ mice restored AOM/DSS-induced tumor progression. Deletion of Cxcr2 did not affect infiltration of dendritic cells, T cells, NK or NKT cells. Deletion of Cxcr2 significantly decreased the migratory ability of MDSCs in vitro and in vivo. MDSCs accelerated tumor growth by inhibiting CD8+ T cell cytotoxic activity. Their results showed that CXCR2 was required for homing of MDSCs into colonic mucosa and colitis-associated tumors, revealing a role of CXCR2 in the recruitment of MDSCs from the circulatory system to local tissues and tumors. The results from adoptive transfer of MDSCs provide direct evidence that MDSCs contribute to colonic tumor formation and growth by inhibiting CD8+ T cell cytotoxicity against tumor cells. The authors conclude, "our findings provide a rationale for the development of therapeutic approaches to subvert . . . tumor-induced immunosuppression by using CXCR2 antagonists . . . ."

Figure 2:
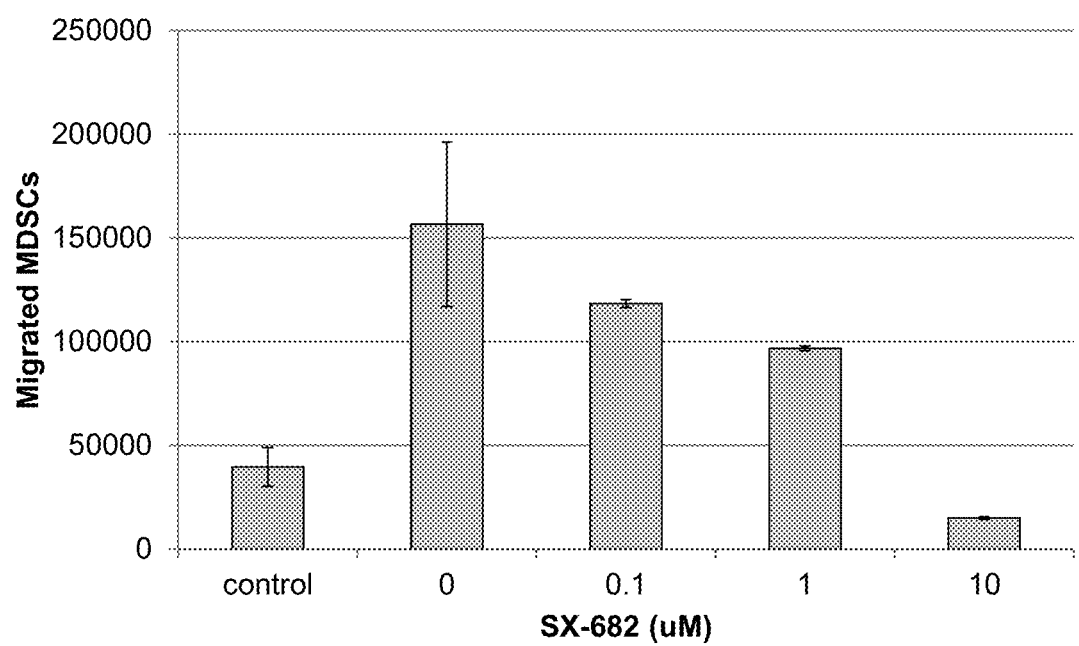
FIG. 2 shows the results of inhibition of myeloid derived suppressor cells (MDSCs) migration by SX-682 in a dose-dependent fashion. The graph shows SX-682 concentration, micromolar (μmolar), vs. the number of migrating MDSCs as measured by flow cytometry. As a control, an aqueous solution with carrier solvent DMSO was used (0 μmolar).
Figure 3A:
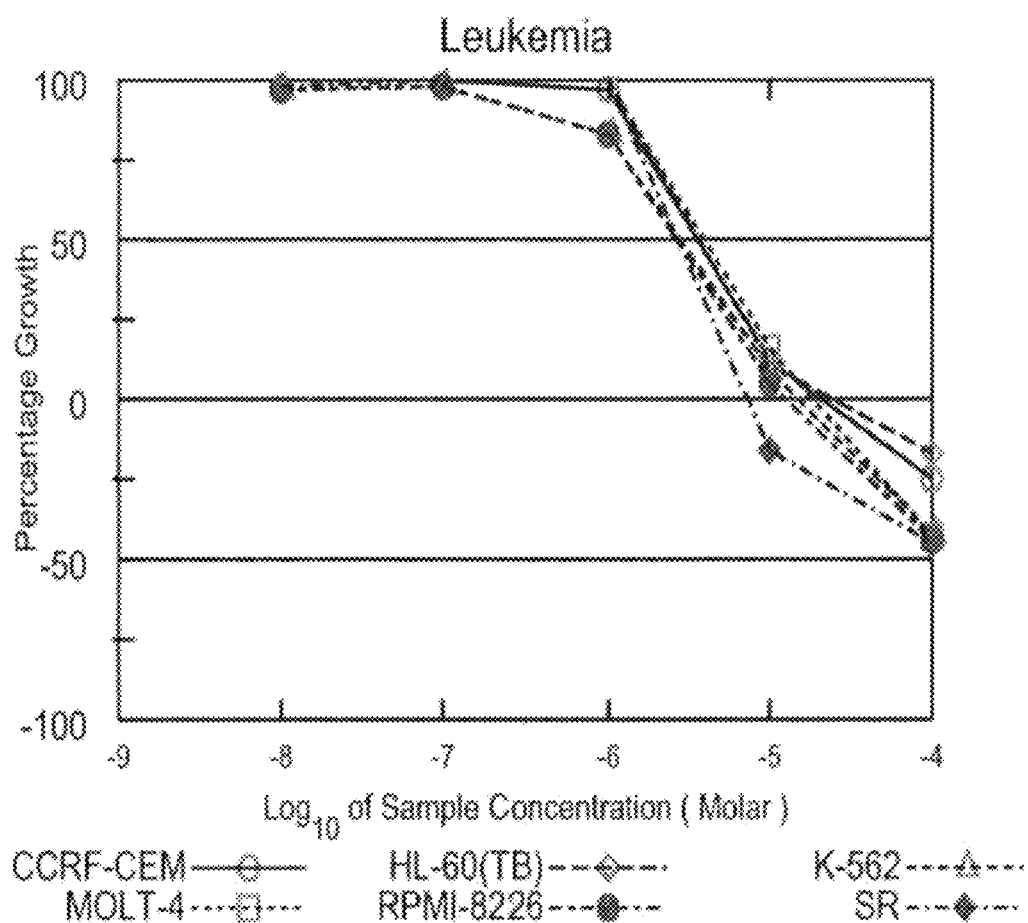
FIG. 3A shows the results of direct inhibition of tumor cell proliferation of leukemia cell lines by SX-682 in a dose-dependent fashion. The leukemia cell lines included CCRF-CEM, MOLT-4, HL-60, RPMI-8226, K-562 and SR. These were independently culture in grown medium at five concentrations of SX-682 between $10^{-8}$ M to $10^{-4}$ molar. Percentage growth inhibition was measured by dye adsorption.
Figure 3B:
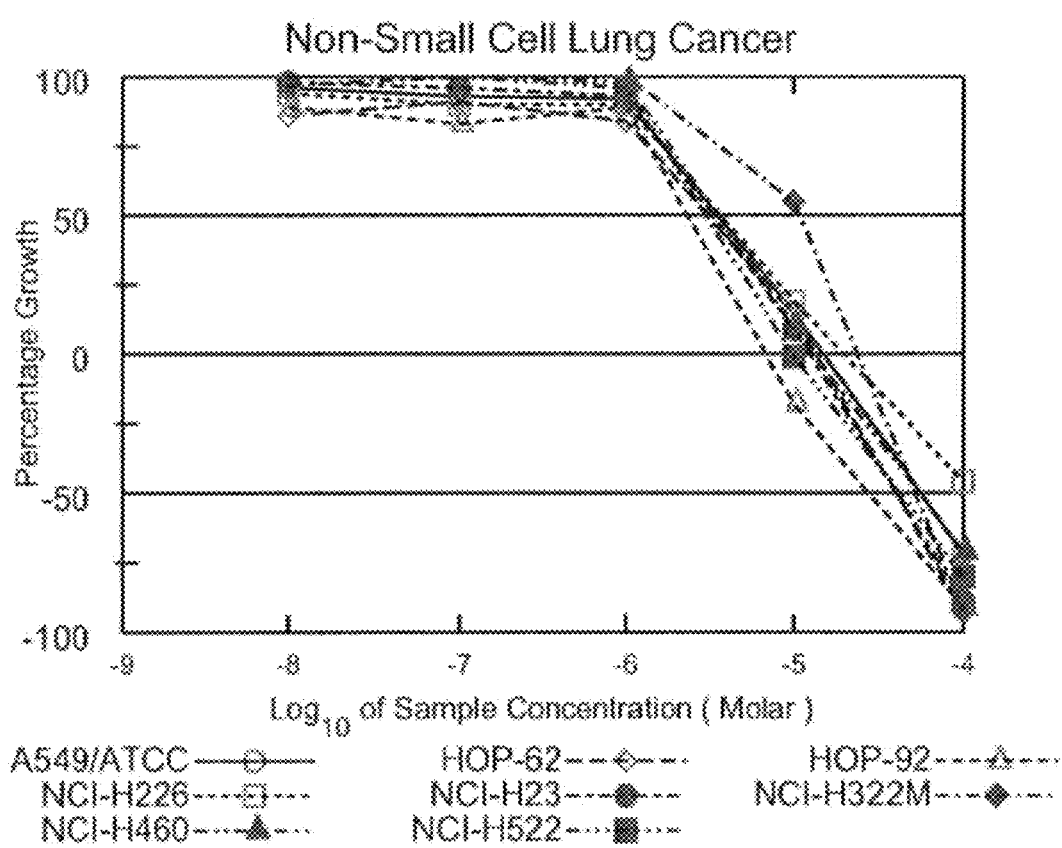
FIG. 3B shows the results of direct inhibition of tumor cell proliferation of non-small cell lung cancer cell lines by SX-682 in a dose-dependent fashion as measured in FIG. 3A. The non-small cell lung cancer cell lines included A549, H226, H460, H23, H522, H322M, HOP-62, and HOP-92.
Figure 3C:
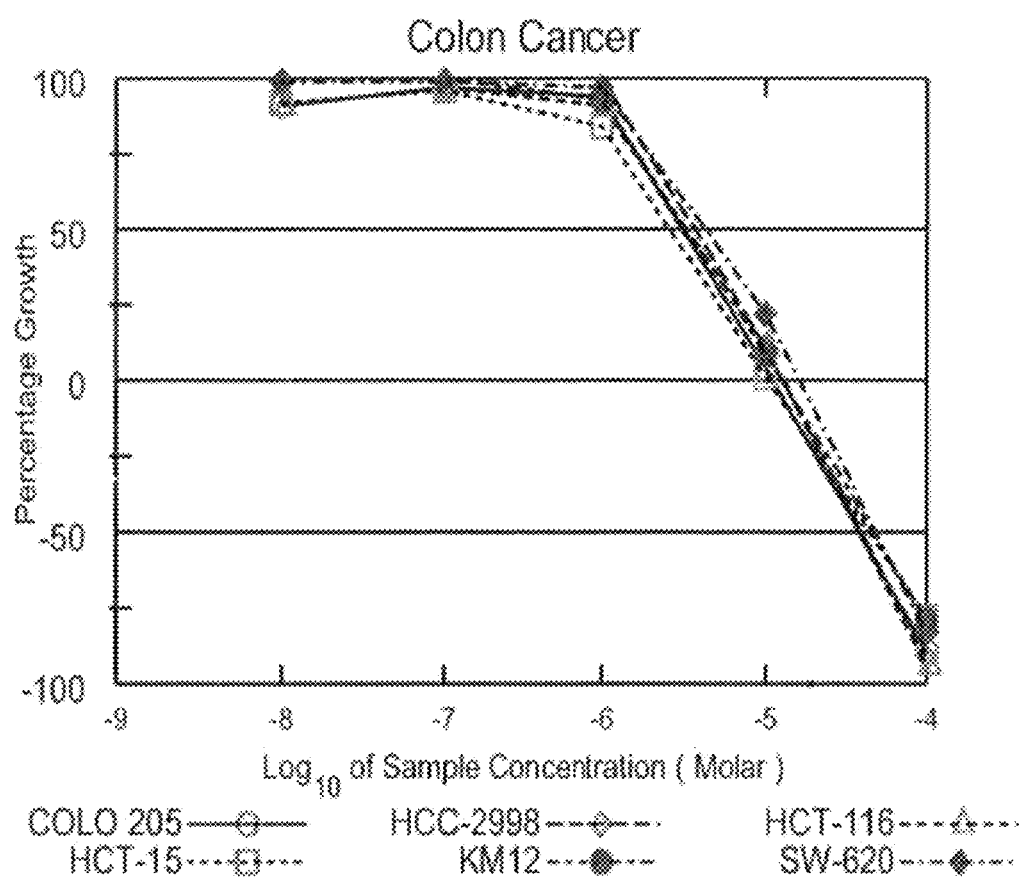
FIG. 3C shows the results of direct inhibition of tumor cell proliferation of colon cancer cell lines by SX-682 in a dose-dependent fashion as measured in FIG. 3A. The colon cancer cell lines included COLO 205, HCT-15, HCC-2998, KM12, HCT-116, and SW-620.
Figure 3D:
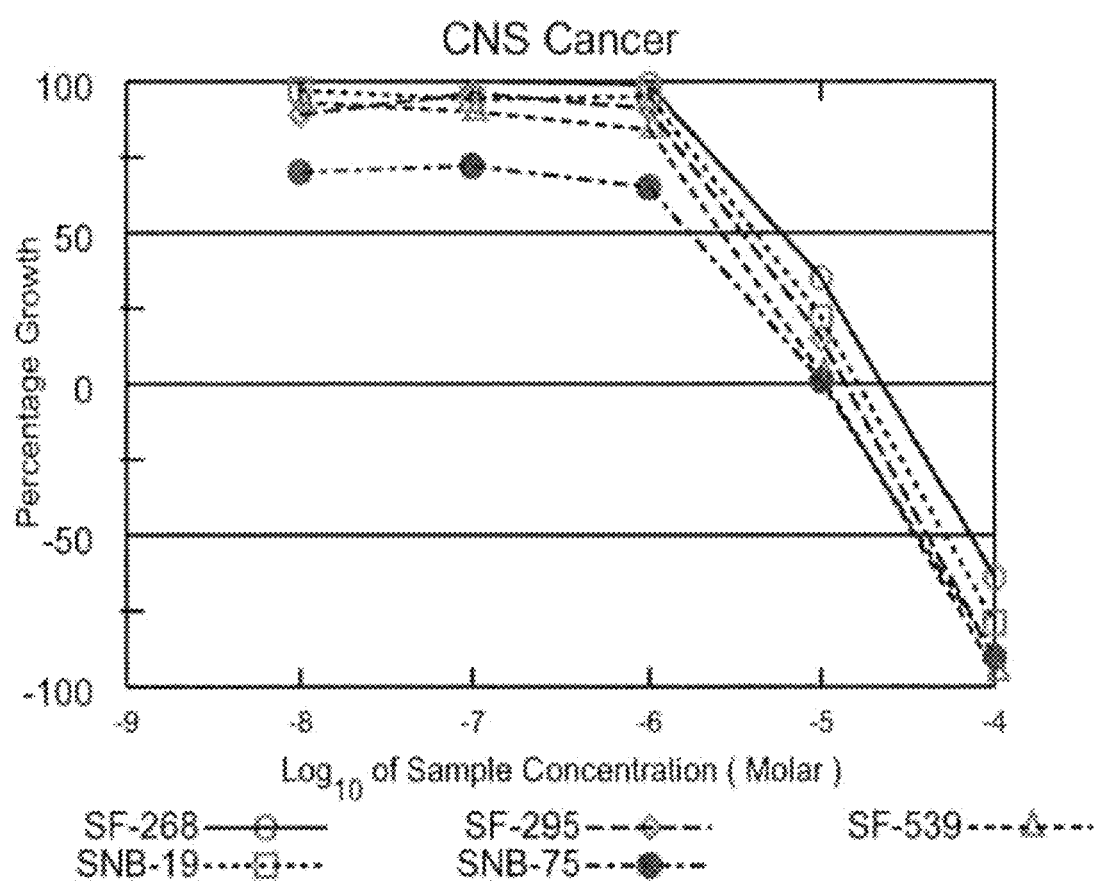
FIG. 3D shows the results of direct inhibition of tumor cell proliferation of CNS cancer cell lines by SX-682 in a dose-dependent fashion as measured in FIG. 3A. The CNS cancer cell lines included SF-268, SNB-19, SF-295, SNB-75, and SF-539.
Figure 3E:
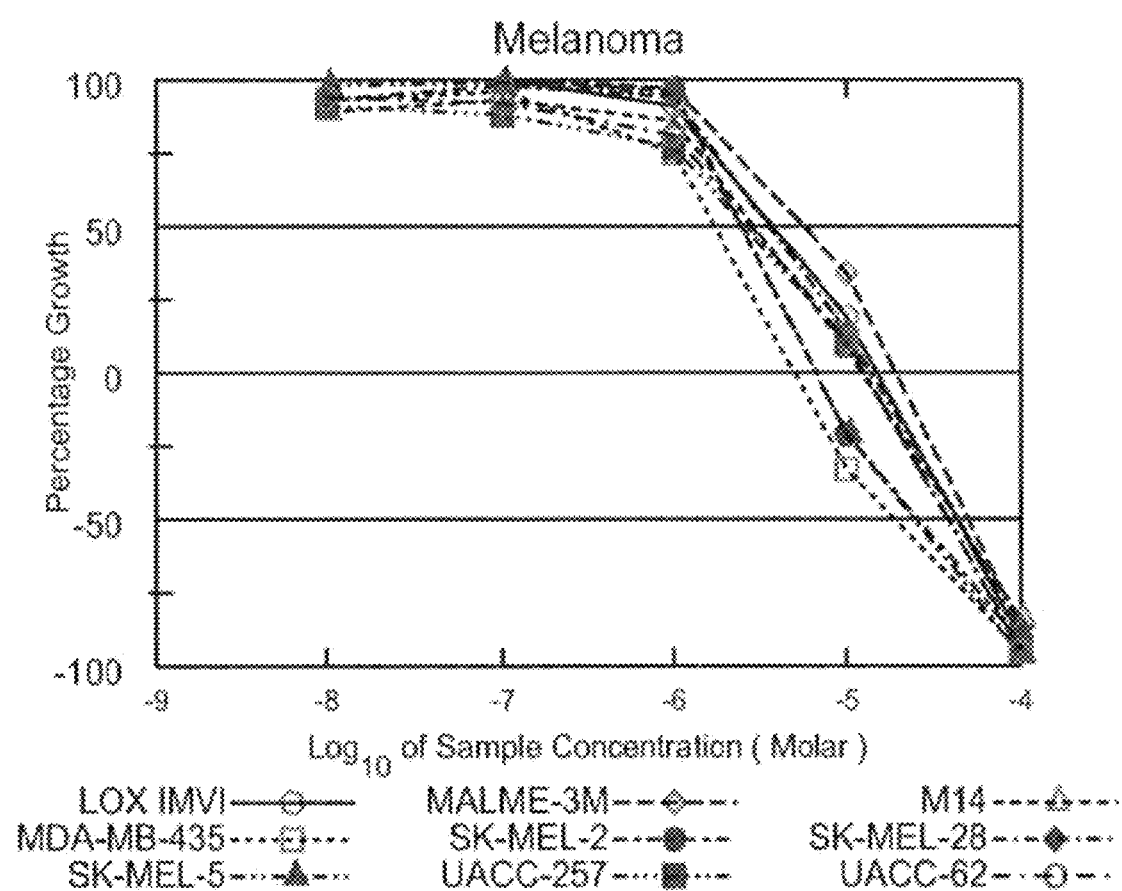
FIG. 3E shows the results of direct inhibition of tumor cell proliferation (melanoma cell lines by SX-682 in a dose-dependent fashion. The melanoma cell lines included LOX IMVI, MDA-MB-435, SK-MEL-5, MALME-3M, SK-MEL-2, UACC-257, M14, SK-MEL-28, and UACC-62.
Figure 3F:
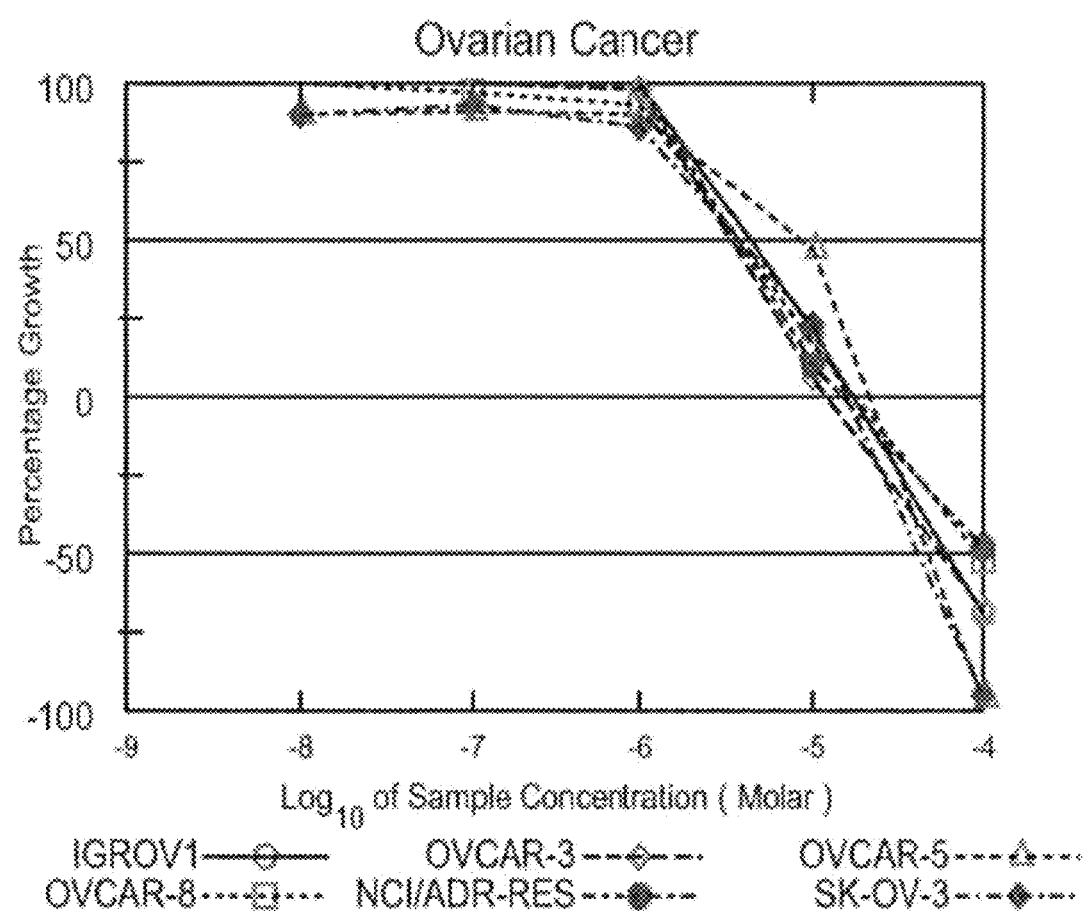
FIG. 3F shows the results of direct inhibition of tumor cell proliferation of ovarian cancer cell lines by SX-682 in a dose-dependent fashion. The ovarian cancer cell lines included IBROV1, OVCAR-8, OVCAR-3, NCI/ADR-RES, OVCAR-5, and SK-OV-3.
Figure 3G:
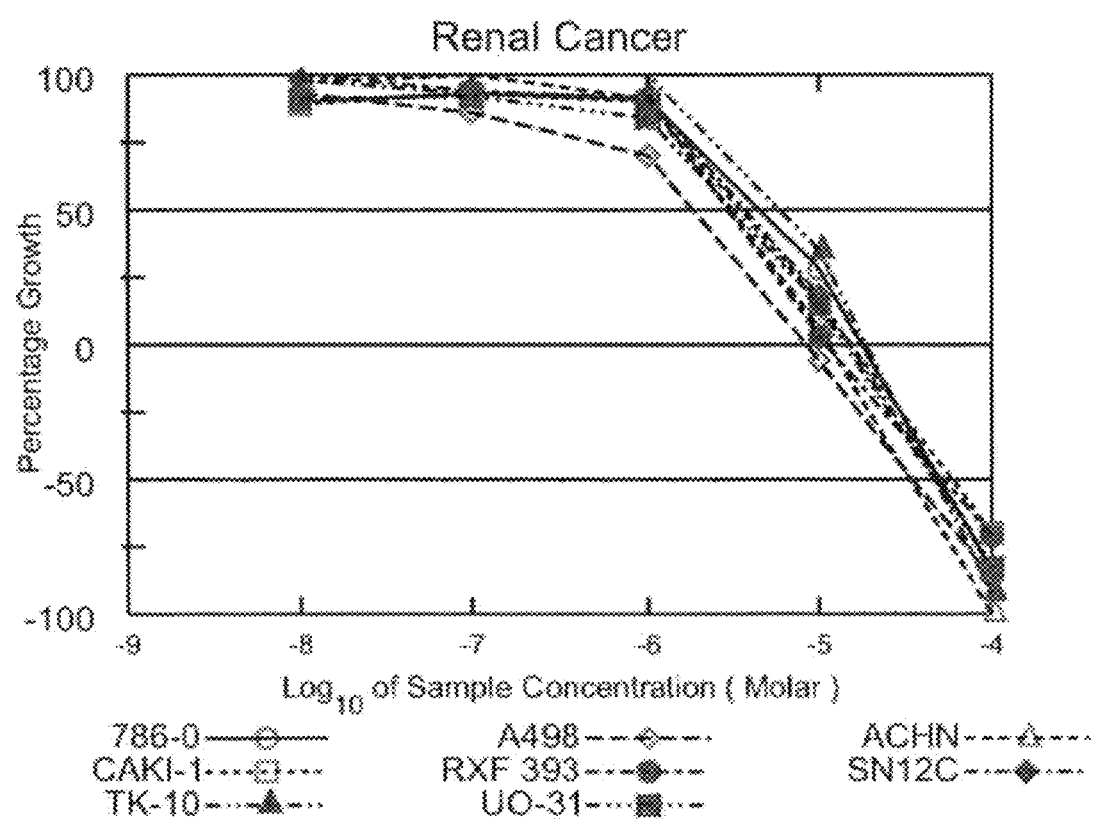
FIG. 3G shows the results of direct inhibition of tumor cell proliferation of renal cancer cell lines by SX-682 in a dose-dependent fashion. The renal cancer cell lines included 786-0, CAK-1, TK-10, RXF 393, UO-31, ACHN, and SN12C.
Figure 3H:
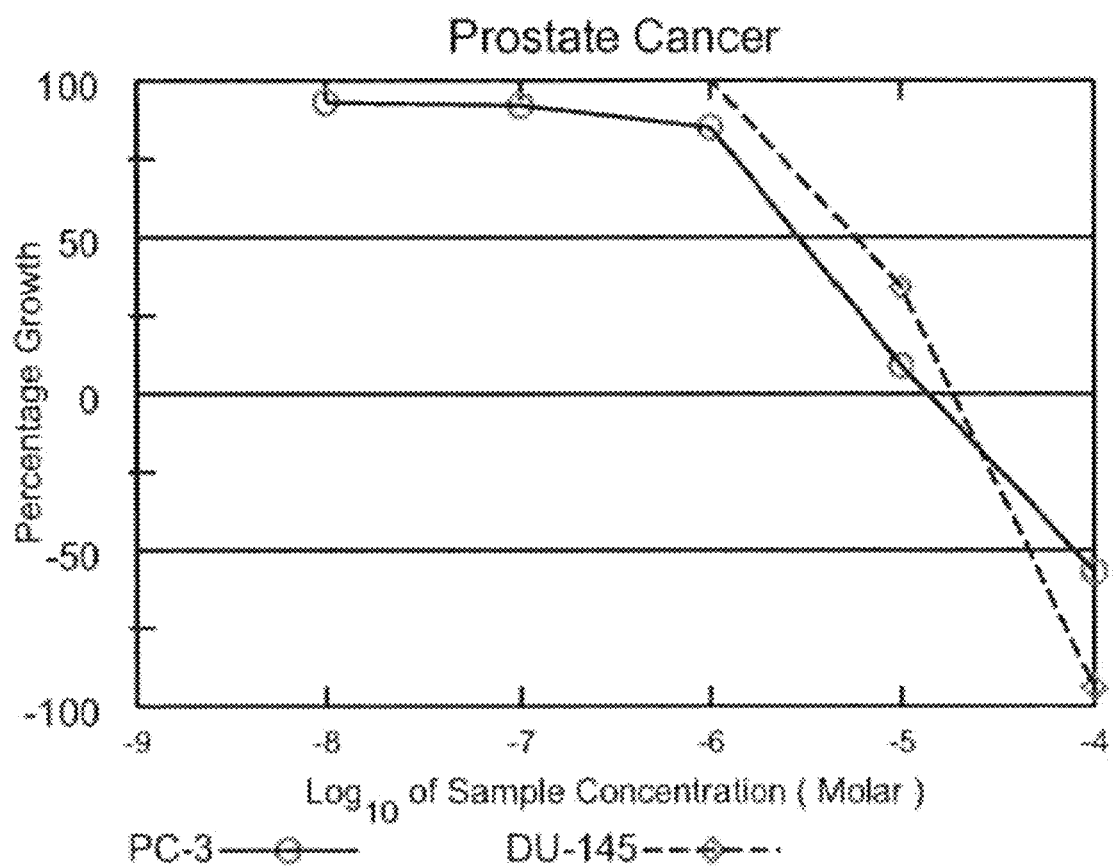
FIG. 3H shows the results of direct inhibition of tumor cell proliferation of prostate cancer cell lines by SX-682 in a dose-dependent fashion. The prostate cancer cell lines included PC-3 and DU-145.
Figure 3I:
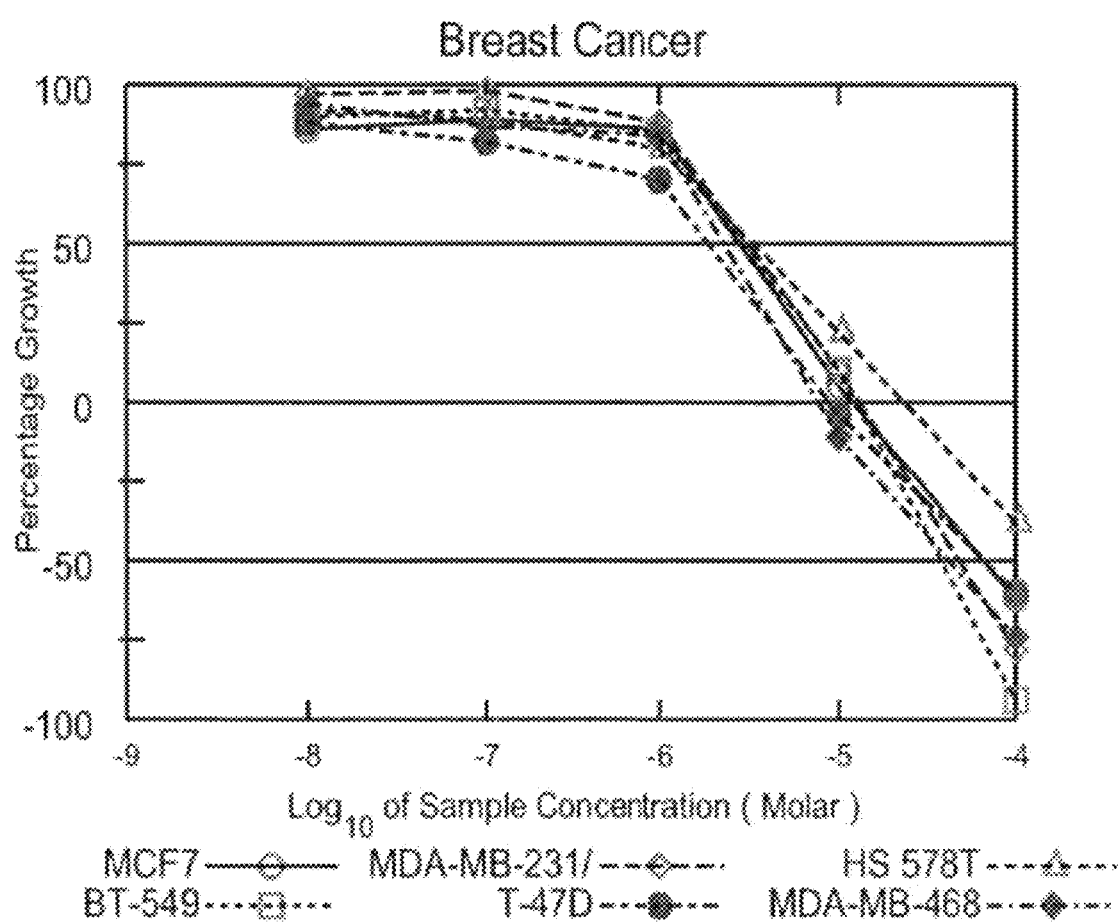
FIG. 3I shows the results of direct inhibition of tumor cell proliferation of breast cancer cell lines by SX-682 in a dose-dependent fashion. The breast cancer cell lines included MCF7, BT-549, MDA-MB-231, T-47D, HS 578T, and MDA-MB-468.

Antagonist SX-682 was used to validate the concept of using a small molecule antagonist of CXCR1 and CXCR2 receptors to block MDSC migration. Using the of method of Katoh, 2013, *Cancer Cell*, 24:631-44 (herein incorporated by reference), to induce and isolate MDSCs, male BALBc mice were given a single intraperitoneal injection of azoxymethane (AOM, 10 mg/kg). Seven days later, these mice were given 4 cycles of water and water containing 1.25% dextran sulfate sodium (DSS). One cycle consisted of providing mice with regular drinking water for 7 days, followed by 1.25% aqueous DSS for 7 days, followed by regular drinking water for 7 days. MDSCs were isolated from femurs and blood of AOM/DSS-treated BALBc mice using the Myeloid-Derived Suppressor Cell Isolation Kit (Miltenyi Biotec) after lysis of red blood cells (RBC) according to the manufacturer's instructions. GROα (CXCL1) was placed in the bottom chamber of a 24-well plate at a concentration of 100 ng/ml. MDSCs isolated from blood of AOM/DSS-treated BALBc mice were seeded at a density of $1\times10^6$/well in the upper chamber (3 m, BD Falcon). After incubation for 12 hours, migrated cells were quantified by flow cytometry using CountBright Absolute Counting Beads (Molecular Probes). To evaluate the effect of SX-682 on GROα-mediated MDSC migration, aqueous DMSO solutions of SX-682 were added to the MDSC-seeded wells prior to migration. The test concentrations of SX-682 were 0.1, 1 and 10 μM, and the DMSO concentration was ≤1%. The results showed that SX-682 was able to effectively inhibit GROα-mediated MDSC migration in a dose-dependent manner (FIG. 2).

Pharmacology Example 2: Inhibition of Tumor Cell Proliferation by SX-682 in a Dose-Dependent Manner The chemokine CXCL8 and its receptors CXCR1 and CXCR2 have been identified as important mediators of cellular proliferation for a number of tumor cell types. To validate the relationship between CXCR1 and CXCR2 receptor antagonism and inhibition of tumor cell proliferation, SX-682 was evaluated against the 60 human tumor cell line panel at five concentration levels (0.01, 0.1, 1, 10, 100 μM) as performed by the Developmental Therapeutics Program at the National Cancer Institute (Shoemaker, 2006, *Nat Rev Cancer*, 6:813-23).

The human tumor cell lines of the cancer screening panel were grown in RPMI 1640 medium containing 5% fetal bovine serum and 2 mM L-glutamine. Cells were inoculated into 96 well microtiter plates in 100 μL at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 h prior to addition of SX-682.

After 24 h, two plates of each cell line are fixed in situ with TCA, to represent a measurement of the cell population for each cell line at the time of drug addition (Tz). SX-682 was solubilized in dimethyl sulfoxide at 400-fold the desired final maximum test concentration and stored frozen prior to use. At the time of SX-682 addition, an aliquot of frozen concentrate was thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions were added to the appropriate microtiter wells already containing 100 μl of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM TRIS, and the absorbance was read on an automated plate reader at a wavelength of 515 nm. For suspension cells, the methodology is the same except that the assay was terminated by fixing settled cells at the bottom of the wells by gently adding 50 μl of 80% TCA (final concentration, 16% TCA). Using the seven absorbance measurements (time zero, (Tz), control growth, (C), and test growth in the presence of drug at the five concentration levels (Ti)), the percentage growth was calculated at each of the drug concentrations levels. Percentage growth inhibition was calculated as:

$(Ti-Tz)/(C-Tz)\times100$ for concentrations for which $Ti>/=Tz$ $(Ti-Tz)/Tz\times100$ for concentrations for which $Ti<Tz$.

Three dose response parameters were calculated for each experimental agent. Growth inhibition of 50% (GI50) is calculated from $[(Ti-Tz)/(C-Tz)]\times100=50$, which was the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from $(Ti-Tz)/Tz\times100=-50$. Values are calculated for each of these three parameters if the level of activity is reached; however, if the effect is not reached or is exceeded, the value for that parameter is expressed as greater or less than the maximum or minimum concentration tested.

The results (FIG. 3A-FIG. 3I) validated the ability of SX-682 to directly affect the proliferation of human tumor cells in the absence of other cells (e.g., MDSCs) through CXCR1/2 antagonism.

Figure 4:
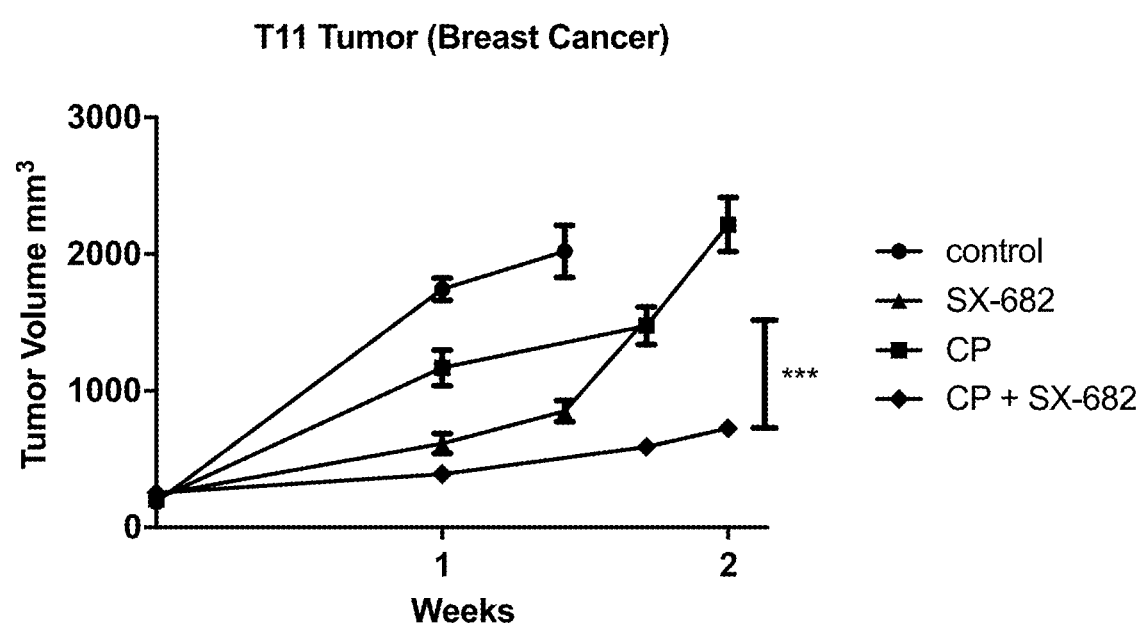
FIG. 4 shows that SX-682 alone or in combination with carboplatin (CP) was an effective therapy for breast cancer in a validated mouse model. The volume (mm$^3$) of tumors in T11 genetically engineered mice was measured during 1-2 week treatment by daily oral administration of SX-682 (10 mg/day/mouse) with or without administration by weekly IP injection of CP (50 mg/kg). The mean, SE, and statistical significance of P<0.0001 (***) for cohorts of seven mice are shown.

Pharmacology Example 3A: Efficacy of CXCR1/2 Antagonism as Single Therapy and in Combination with Carboplatin in the T11 Mouse Model of Breast Cancer The T11 model is a validated mouse model of breast cancer, which derives from the serial orthotopic transplantation of a murine breast tumor derived from a p53-null mouse into a syngeneic p53 competent recipient, and features sporadic, somatic K-Ras mutation (Herschkowitz, 2012, *Proc Natl Acad Sci*, 109:2778-83, herein incorporated by reference). Tumors from the T11 model display an RNA expression pattern characteristic of the human claudin-low disease, and are extremely aggressive, with the majority of untreated animals surviving less than 21 days from the time of enrollment in the therapy studies. Treatment regimens were started following tumor manifestation. SX-682 was given orally via medicated feed, at an approximate dose of 10 mg/day/mouse. In brief, the medicated feed was prepared by Research Diets (New Brunswick, N.J.) by incorporating 15.2 grams of SX-682 spray dried dispersion (as prepared in Formulation Example 1) into 1042 grams of standard rodent diet with 10% kcals from fat. The medicated feed was formed into pellets. Carboplatin (CP) was administered once weekly via intraperitoneal injection at a dose of 50 mg/kg. The results (FIG. 4) showed the addition of SX-682 to carboplatin significantly reduced tumor growth (N=7 each cohort). The combination of SX-682 and CP resulted in a synergistic inhibition of tumor growth and progression in treatment animals, which is a surprising and unexpected result. Mean±SE. *** P<0.0001 (linear regression).

Figure 5:
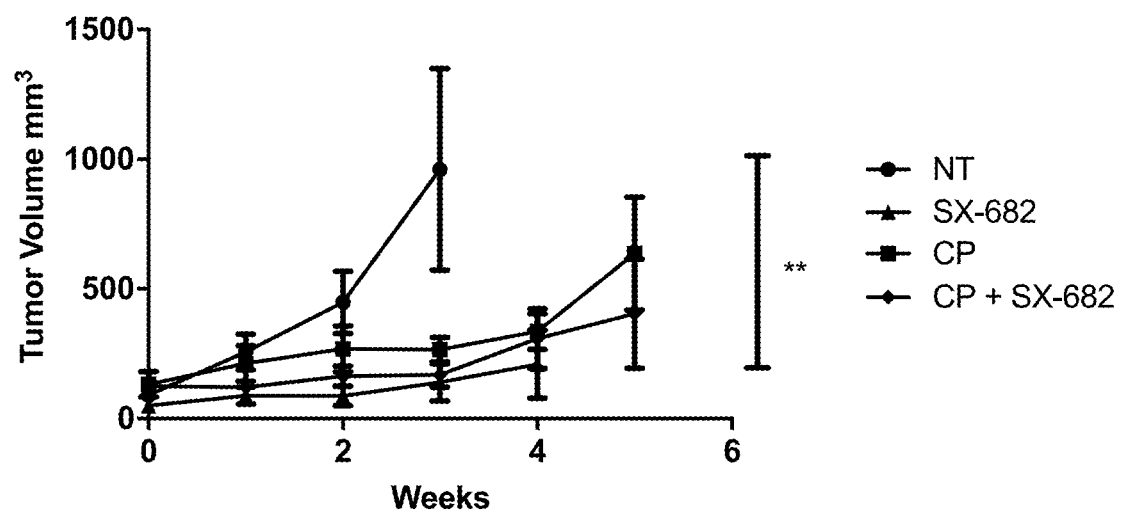
FIG. 5 shows that SX-682 alone or synergistically in combination with CP was an effective treatment for breast cancer in a validated animal model. The volume ($mm^3$) of tumors in C3Tag genetically engineered mice was measured during 4-6 week treatment dosing as in FIG. 4. The mean, SE, and statistical significance of P<0.0001 for cohorts of 10-12 mice are shown.
Figure 6:
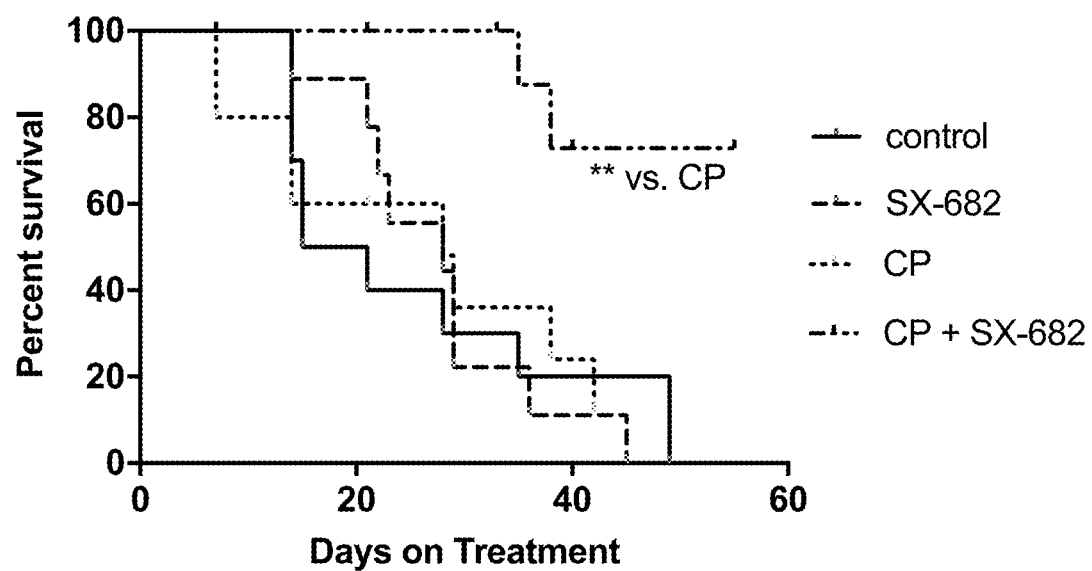
FIG. 6 shows that SX-682 synergized CP to improve survival in a treatment for breast cancer. The treatments were administered in the C3Tag genetically engineered mouse model of breast cancer as described in FIG. 5. The treatment extended for up to 60 days. The results show that the combination therapy (SX-682+CP) significantly improved survival over CP or SX-682 alone (P=0.008).

Pharmacology Example 3B: Efficacy of CXCR1/2 Antagonism as Single Therapy and in Combination with Carboplatin in the C3Tag Mouse Model of Breast Cancer The C31-T-antigen (C3Tag) mouse model is a validated model of human triple-negative basal cell breast cancer as shown by gene expression analysis (Maroulakou, 1994, *Proc Natl Acad Sci*, 91:11236-40, herein incorporated by reference). The expressed large T-antigen binds and inactivates the RB and p53 tumor suppressor genes, explaining why this model faithfully recapitulates human basal breast cancer, which also harbors RB and p53 inactivation. This model also has frequent K-Ras amplification and infrequent Ras mutations. Treatment regimens were started following tumor manifestation. SX-682 was given orally via medicated feed, at an approximate dose of 10 mg/day/mouse. Carboplatin (CP) was administered once weekly via intraperitoneal injection at a dose of 50 mg/kg. The results (FIGS. 5 and 6) showed SX-682 treatment alone and in combination with carboplatin significantly reduced tumor growth as compared to untreated controls (N=10-12 per cohort). Mean±SE. ** P<0.001 (linear regression). Median survival for vehicle, carboplatin and SX-682 cohorts was 18, 28 and 28 days. Combining SX-682 with CP significantly increased survival compared to carboplatin alone (P=0.008), giving a median survival well beyond 60 days. The combination of SX-682 and CP resulted in a synergistic extension of survival in treatment animals, which is a surprising and unexpected result.

Figure 7:
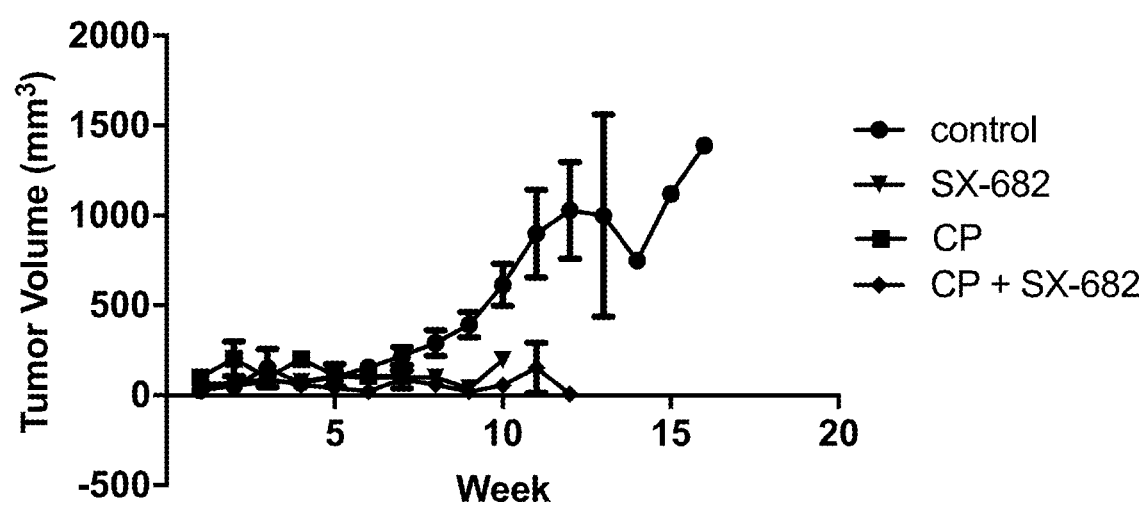
FIG. 7 shows that SX-682 alone or in combination with CP was an effective treatment for melanoma in a validated animal model. The volume ($mm^3$) of tumors in TRIA genetically engineered mice was measured during 15-20 week treatment dosing SX-682 and CP as in FIG. 4. The mean, SE, and statistical significance of P<0.0001 for cohorts of 10-12 mice are shown.
Figure 8:
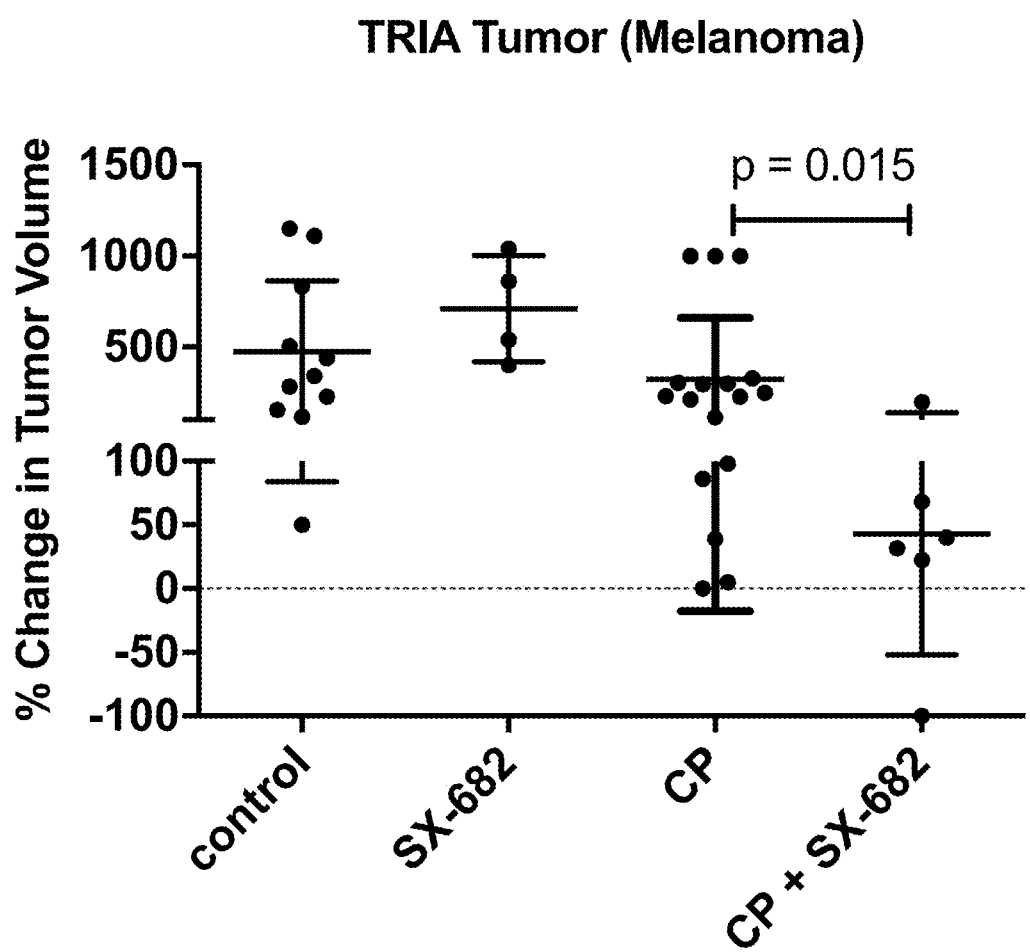
FIG. 8 shows that SX-682 synergized with CP to cause remission of melanomas in the validated mouse model as described in FIG. 7. 21-days of combination treatment caused a significant percentage change in tumor volume in TRIA genetically engineered mice compared to CP treatment alone.

Pharmacology Example 3C: Efficacy of CXCR1/2 Antagonism as Single Therapy and in Combination with Carboplatin in the TRIA Mouse Model of Melanoma The Tyrosine-Hras/Ink/Arf null (TRIA) is a validated mouse model of melanoma features an immuno-competent autochthonous tumor; Ras events are in >70% of all melanomas, and ~50% lose the INK4a/ARF locus which, with B-RAF mutations, is the most common lesion of this cancer (Sharpless, 2016, *Cancer Cell* 29:832-45). Treatment regimens were started following tumor manifestation. SX-682 was given orally via medicated feed, at an approximate dose of 10 mg/day/mouse. Carboplatin (CP) was administered once weekly via intraperitoneal injection at a dose of 50 mg/kg. The results of this experiment can be seen in FIGS. 7 and 8. SX-682 treatment alone significantly slowed tumor growth comparable to CP alone. SX-682 combination therapy did better than monotherapy and achieved complete remission (zero tumor volume) in 5 of 11 animals. The combination of SX-682 and CP resulted in a synergistic inhibition of tumor growth and progression in treatment animals, which is a surprising and unexpected result.

Pharmacology Example 3D: Efficacy of CXCR1/2 Antagonism as Single Therapy and in Combination with Temozolomide in a Mouse Model of Glioblastoma Multiforme Mouse glioma cell line GL261 is frequently used in experimental models of glioblastoma to evaluate various experimental modalities. Szatmari, 2006, *Cancer Sci* 97:546-55 (herein incorporated by reference). To test the hypothesis that dual CXCR1/2 antagonism may potentiate anti-tumor effects of chemotherapy in a mouse model of glioblastoma, tumor-bearing C57BL/6 mice are dosed with CXCR1/2 antagonist alone and in combination with temozolomide (TMZ). Mouse syngeneic tumor GL261 cells are grown with Dulbecco modified Eagle medium supplemented with 10% fetal bovine serum as well as streptomycin (100 mg/mL) and penicillin (100 U/mL) at 37° C. in a humidified atmosphere of 95% air/5% $CO_2$. Mouse glioma GL261 cells are cultured, harvested, and injected into the lower right flank of each C57BL/6 mouse. For the subcutaneous model, $10^6$ GL261 cells are injected into the lower right flank of each C57BL/6 mouse. TMZ is dosed via intraperitoneal injection according to body weight (20 mg/kg). CXCR1/2 antagonist is dosed via oral administration daily. At the beginning of treatment, mice are either randomized by tumor volume or by body weight. The number of animals per group range from between 10-12 animals per group as determined based on Good Statistical Practice analysis. Both tumor and body weight measurements are collected twice weekly and tumor volume is calculated using the equation $(L \times W^2)/2$, where L and W refer to the length and width dimensions, respectively. Error bars are calculated as standard error of the mean. The general health of mice is monitored daily and all experiments are conducted in accordance to AAALAC and institution-based IACUC guidelines for humane treatment and care of laboratory animals. Kaplan-Meier statistical analysis is performed using the Log-rank test using GraphPad Prism.

Figure 9:
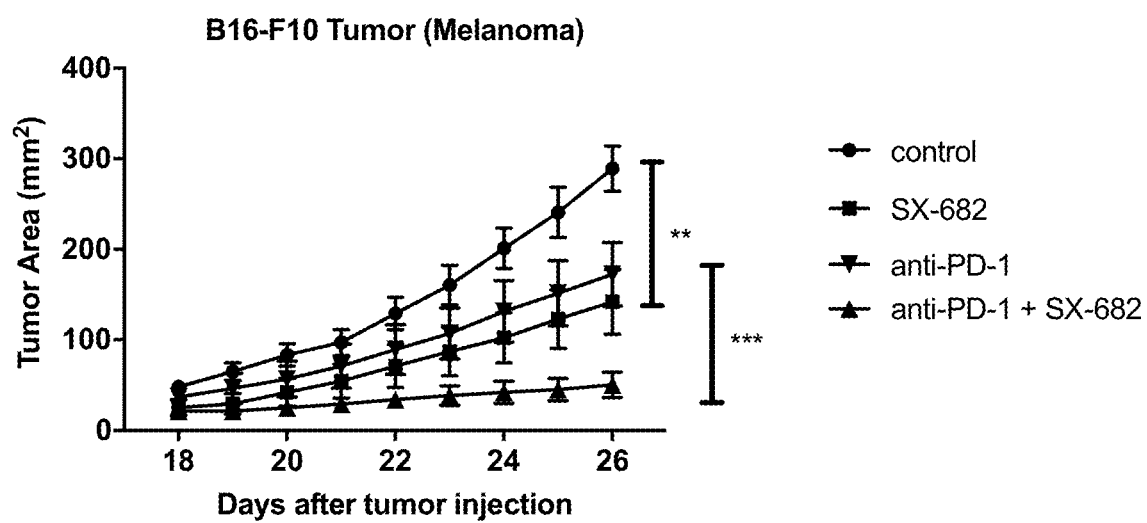
FIG. 9 shows that SX-682 alone or in combination with anti-PD-1 antibody was effective in treating melanomas in a mouse model. The tumor area ($mm^2$) in B16-F10 syngeneic mice was measured during 26 days of treatment with SX-682 orally administered twice daily (50 mg/kg) with and without 100 µg anti-PD-1 administered twice weekly by IP injection. SX-682 monotherapy significantly slowed tumor growth vs. control (P=0.0002, ) and synergized with anti-PD1 therapy vs. monotherapy with either SX-786 or anti-PD-1 (P<0.0005, *). Data and error bars are the mean±SE of 4 or 5 mice per cohort.

Pharmacology Example 4A: Efficacy of CXCR1/2 Antagonism as Single Therapy and in Combination with Anti-PD1 Antibody in the B16-F10 Syngeneic Mouse Model of Melanoma The B16-F10 mouse model is a validated model of melanoma, Overwijk, 2001, *Curr Protoc Immunol*, Chapter 20: Units 20-21 (herein incorporated by reference). It was used to evaluate the effect of SX-682 alone and in combination with anti-PD1 antibody. B16-F10 mouse melanoma cells were cultured, then mice were injected with $0.5 \times 10^6$ B16-F10 cells on day 0, and treatment was initiated on day 18. Mice were treated with vehicle (control), SX-682 alone (50 mg/kg twice daily, oral), anti-PD-1 alone (100 μg twice weekly, ip), or SX-682 in combination with anti-PD-1 (N=4-5 per cohort). SX-682 was used as a spray dried dispersion (Formulation Example 1), and was administered to mice via oral gavage as a suspension in 0.5% aq methylcellulose. The results (FIG. 9) showed SX-682 monotherapy significantly slowed tumor growth (P=0.0002, linear regression) and potently synergized with anti-PD1 therapy with the combination significantly better than either therapy alone (P<0.0005 for both comparisons). Data and error bars are the mean±SE. The combination of SX-682 and immune checkpoint inhibition resulted in a synergistic inhibition of tumor growth and progression in treatment animals, which is a surprising and unexpected result.

Figure 10:
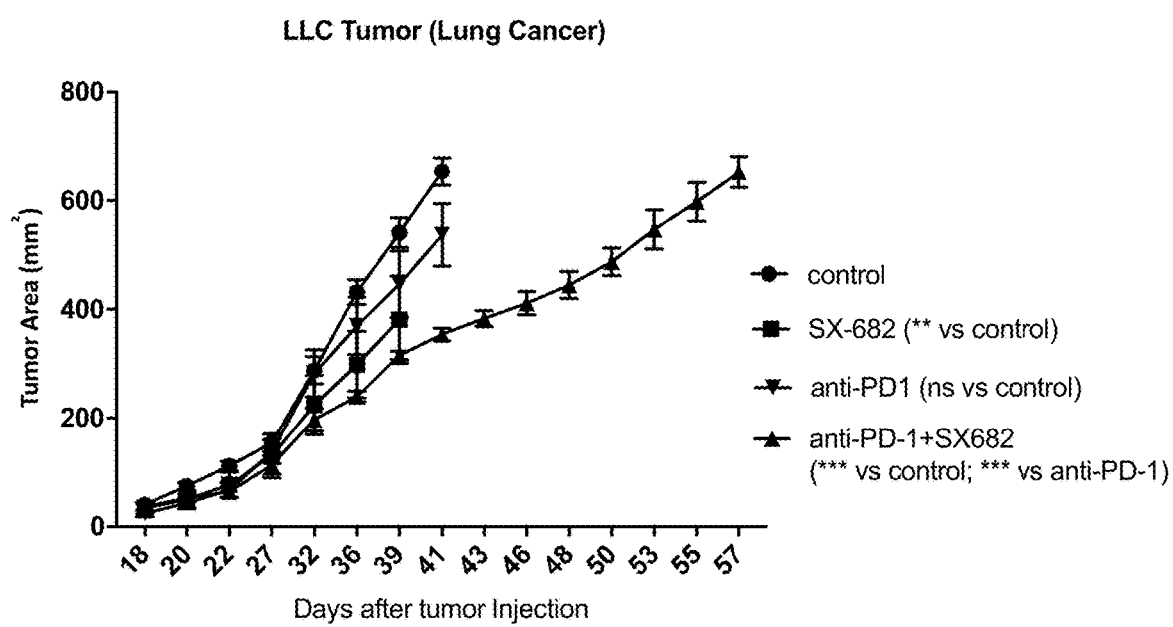
FIG. 10 shows that SX-682 alone or in combination with anti-PD-1 antibody inhibited lung cancer in a validated animal model using the dosing amounts as in FIG. 9. Tumor area ($mm^2$) was measured in LLC syngeneic mice. SX-682 monotherapy significantly slowed tumor growth vs. control (P=0.0002, ) and synergized with anti-PD1 therapy vs. monotherapy with either SX-682 or anti-PD-1 (P<0.002, *). Data and error bars are the mean±SE in cohorts of 5 mice.
Figure 11:
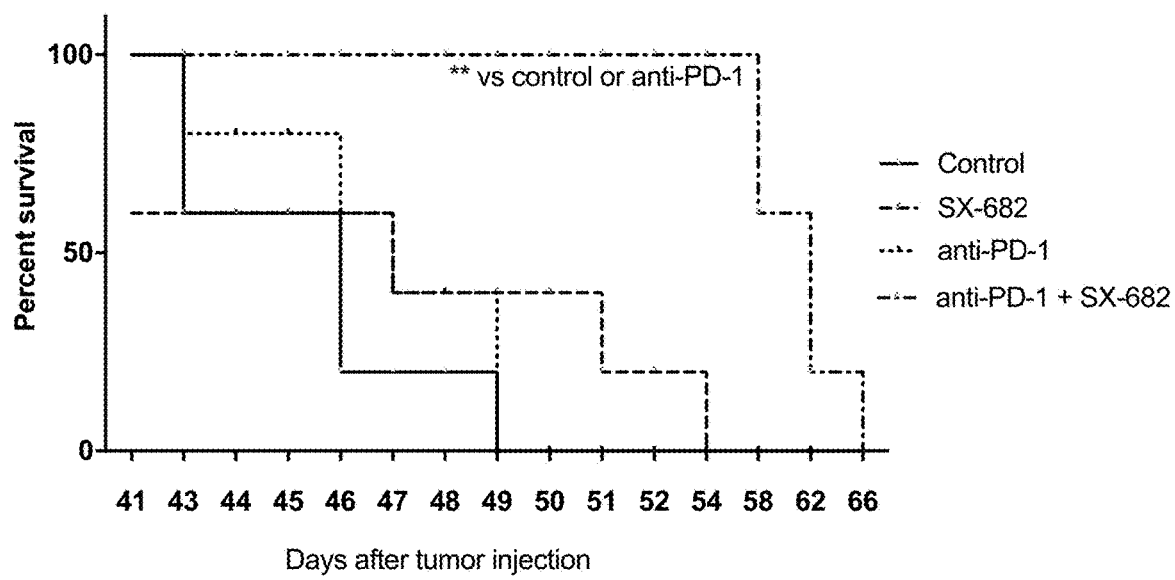
FIG. 11 shows that SX-682 synergized with anti-PD-1 antibody to increase survival in the LLC syngeneic mice as described in FIG. 10. Drug administration and survival determinations continued up to 66 days after tumor injection. The combination of SX-682 and anti-PD-1 therapy significantly enhanced survival compared to vehicle or anti-PD-1 therapy alone (P=0.002).

Pharmacology Example 4B: Efficacy of CXCR1/2 Antagonism as Single Therapy and in Combination with Anti-PD1 Antibody in the LLC Syngeneic Mouse Model of Lung Cancer The Lewis lung carcinoma (LLC) mouse model (Kellar, 2015, *Biomed Res Int,* 2015:621324, herein incorporated by reference) was used to evaluate the effect of SX-682 alone and in combination with anti-PD-1 antibody. LLC mouse melanoma cells were cultured, then mice were injected with $0.5 \times 10^6$ LLC cells on day 0, and on day 18 treatment was initiated. Mice were treated with vehicle (control), SX-682 alone (50 mg/kg twice daily, oral), anti-PD-1 alone (100 µg twice weekly, ip), or SX-682 in combination with anti-PD-1 (N=5 per cohort). SX-682 was used as a spray dried dispersion (Formulation Example 1), and was administered to mice via oral gavage as a suspension in 0.5% aq. methylcellulose. The results of this experiment can be seen in FIG. 10 and FIG. 11. SX-682 monotherapy significantly slowed tumor growth (P=0.0076, linear regression), and potently synergized with anti-PD1 therapy with the combination significantly better than either therapy alone (P<0.0001 for both comparisons). The combination of SX-682 and anti-PD-1 therapy significantly enhanced survival compared to vehicle or anti-PD-1 therapy alone (P=0.002). The combination of SX-682 and immune checkpoint inhibition resulted in a synergistic effect on both tumor growth and survival in treatment animals, which is a surprising and unexpected result.

Figure 12:
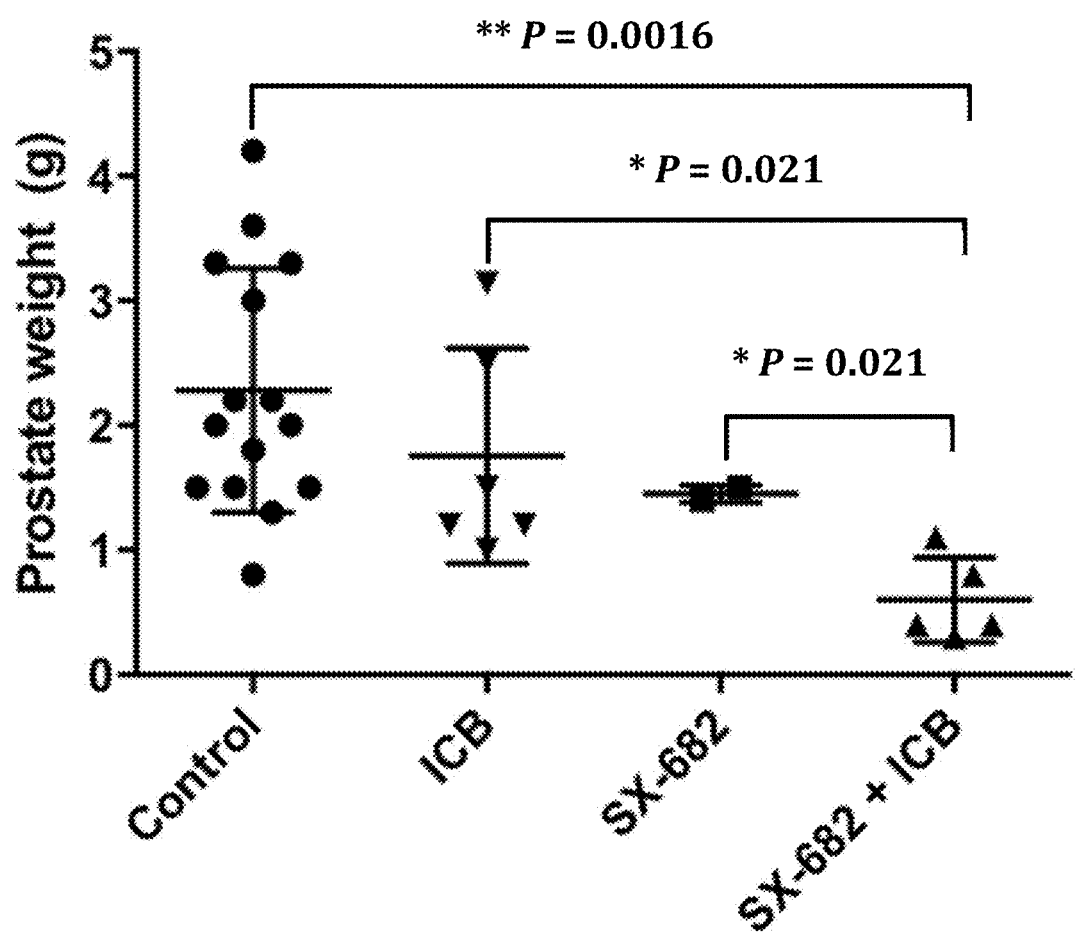
FIG. 12 shows that SX-682 alone and in combination with immune checkpoint blockade (anti-PD1 and anti-CTLA4) inhibited prostate cancer in a validated animal model. $Pten^{pc-/-}p53^{pc-/-}Smad4^{pc-/-}$ mice were administered 50 mg/kg SX-682 by oral gavage b.i.d. and 200 µg each of anti-PD1 and anti-CTLA4 antibodies (ICB), 3×/week. Prostate weight (g) was measured after 4-6 weeks. SX-682 plus ICB was significantly better than control (P=0.0016, **), and ICB or SX682 alone (P=0.021, *) (unpaired t-test). Mean+SE are shown.

Pharmacology Example 4C: Efficacy of CXCR1/2 Antagonism as Single Therapy and in Combination with Anti-PD1 and Anti-CTLA4 Antibody in a Mouse Model of Castration Resistance Prostate Cancer The genetically engineered $Pten^{pc-/-}p53^{pc-/-}Smad4^{pc-/-}$ mouse is a prostate-specific PB promoter-driven (PB-Cre4) conditional triple knockout model (i.e., prostate-specific deletion of all three tumor suppressors, Pten, p53 and Smad4 occurs in the 'prostate cancer' or 'pc'). It exhibits an aggressive tumor phenotype, and like the human disease, develops spontaneous bone metastases (Ding, 2012, *Cell,* 148:896-907) $Pten^{pc-/-}p53^{pc-/-}Smad4^{pc-/-}$ mice at 3-4 months of age with established tumors ($\geq 150$ mm$^3$, as measured by MRI) were treated with either vehicle (control), SX-682 (50 mg/kg b.i.d.), ICB (200 µg each of anti-PD1 and anti-CTLA4 antibodies, 3×/week), or the SX-682 and ICB combination (SX-682+ICB). SX-682 was used as a spray dried dispersion (Formulation Example 1), and was administered to mice via oral gavage as a suspension in 0.5% aq. methylcellulose. Treatment was continued for 4-6 weeks and prostate weights measured to determine tumor burden. The results (FIG. 12) showed SX-682 plus ICB was significantly better than control or either treatment alone (unpaired t-test). Mean±SE. The combination of SX-682 and immune checkpoint inhibition resulted in a synergistic inhibition of tumor growth and progression in treatment animals, which is a surprising and unexpected result.

Pharmacology Example 5A: Cell-kill Efficacy of CXCR1/2 Antagonism as Single Therapy and in Combination with T-Cell Therapy In Vitro To validate the use of a small molecule CXCR1/2 antagonist to halt the EMT process in tumor cells thereby decreasing immunoresistance, human tumor cells will be exposed in vitro to various doses of SX-682 in the presence of immune effector cells. These studies will be conducted with and without addition of exogenous recombinant IL-8. Tumor cells will be subsequently evaluated for proliferation/survival, expression of epithelial/mesenchymal markers and stemness markers, expression of immune-relevant molecules, and cytotoxic response to various immune effector cells (human antigen-specific T cell lines generated from the blood of cancer patients or healthy donors by using peptide epitopes from the following antigens: CEA, MUC1, brachyury, or natural killer cells isolated from blood of normal donors and left untreated or activated via IL-2)

Pharmacology Example 5B: Efficacy of CXCR1/2 Antagonism as Single Therapy and in Combination with T-Cell Therapy in a Mouse Model of Pancreatic Cancer Although born with histologically normal pancreata, K-ras$^{LSL.G12D/+}$; p53$^{R172H/+}$; PdxCre (KPC) mice developed pancreatic intraepithelial neoplasia (PanIN) lesions on an accelerated schedule, and died of pancreatic ductal adenocarcinoma (PDAC) with a median survival of 5.5 months. Metastases were observed ~80% of the animals, at the same sites seen in human PDAC patients (liver, lung, and peritoneum). Tumors arising in this model were found to have many of the immunohistochemical markers associated with human disease, and bore evidence of widespread genomic alterations, a feature that was previously lacking in most genetically engineered mouse models. The KPC mouse model of PDAC is widely used to evaluate treatment modalities in a preclinical setting (Westphalen, 2012, *Cancer J,* 18:502-10, incorporated herein by reference). To test the hypothesis that dual CXCR1/2 antagonism may potentiate anti-tumor effects of T-cell therapy in a mouse model of PDAC, tumor-bearing KPC mice are dosed with SX-682 alone and in combination with T-cell therapy. T-cells are either selected for or engineered towards high affinity binding to a specific protein of interest located on the tumor cell. In the case of PDAC, these proteins of interest may include (but are not limited to) mesothelin, Wilms' tumor antigen, Mucin 1, or Annexin A2. KPC mice will undergo serial high-resolution ultrasound imaging (Vevo 2100) at 8 weeks of age to monitor autochthonous tumor development. Mice are enrolled based on defined pancreatic mass 3-6 mm. At the start of treatment, select cohorts will receive CXCR1/2 antagonist via oral administration daily. For animals undergoing T-cell therapy, they will receive cyclophosphamide once at enrollment (180 mg/kg) followed 6 hours later by intravenous infusion of $1 \times 10^7$ twice-stimulated engineered T cells followed by $1 \times 10^7$ peptide-pulsed irradiated splenocytes. Recipient mice will also receive IL-2 ($2 \times 10^4$ IU, i.p.) every other day for 8 days (in timepoint studies) or for 5 days (in survival studies) to promote donor T cell survival and expansion. For serial T cell infusions, mice will receive the same treatment protocol, excluding the cyclophosphamide after the first dose, every 2 weeks. Power analyses will guide enrollment numbers to power the study for a large effect (>50% increase in median overall survival). Both tumor and body weight measurements are collected twice weekly and tumor volume is measured via serial high resolution ultrasound imaging. Error bars are calculated as standard error of the mean. The general health of mice is monitored daily and all experiments are conducted in accordance to AAALAC and institution-based IACUC guidelines for humane treatment and care of laboratory animals. Kaplan-Meier statistical analysis is performed using the Log-rank test using GraphPad Prism.

Pharmacology Example 6: Efficacy of CXCR1/2 Antagonism as Single Therapy and in Combination with Cancer Vaccine in a Mouse Model of Cancer All animal studies re carried out in accordance with the guidelines of the Association for Assessment and Accreditation of Laboratory Animal Care. Experimental studies were carried out under approval of the NIH Intramural Animal Care and Use Committee. Murine colon carcinoma MC38 cells are stably transfected with chorioembryonic antigen (CEA), and subcutaneously implanted into female C57BL/6 mice on day 0. Beginning on day 7, animals are dosed daily with SX-682 via medicated feed. Beginning on day 14, test animals are vaccinated weekly with either Hank's Balanced Salt Solution or 50 mg of a gp70 peptide (p15e) emulsified in Montanide ISA-51-VG (Seppic) at a 1:1 ratio. Evaluation of the effect of SX-682 on various immune cell subsets in non-tumor bearing mice will be evaluated. Spleens will be collected and analyzed for antigen-specific immune responses and various immune cell subsets. Anti-tumor effect of combinations of SX-682 with cancer vaccines will be evaluated. Evaluations will include effect on tumor volume, tumor microenvironment, including tumor phenotype, etc., will be evaluated. Vaccine-specific immune responses will also be measured.

We claim:

1. A method of treating cancer in a patient in need of such treatment, comprising administering to the patient a pharmaceutical composition,
   wherein the pharmaceutical composition comprises a therapeutically effective amount of a compound selected from the following formulas:

SX-517

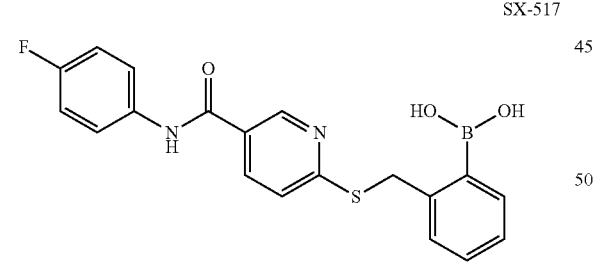

SX-520

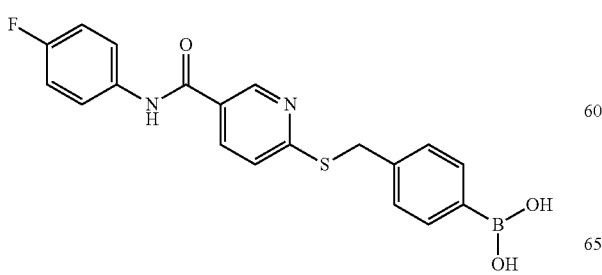

-continued

SX-557

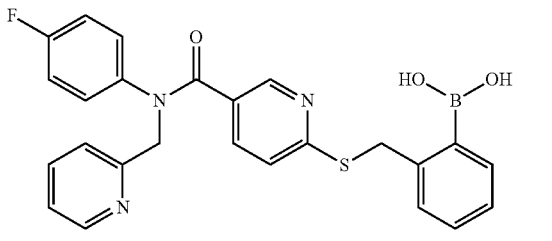

SX-574

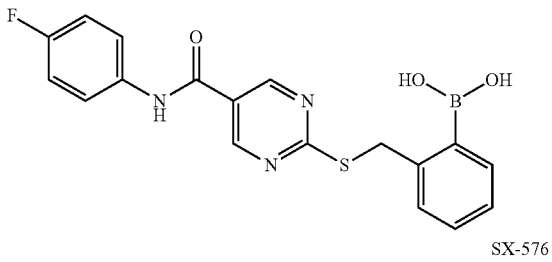

SX-576

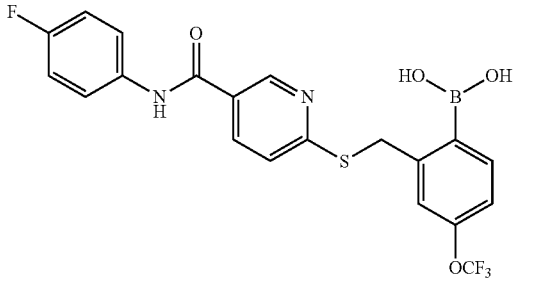

SX-577

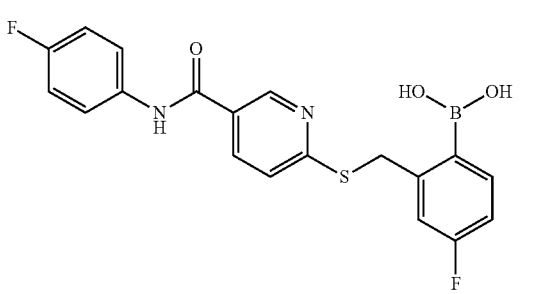

SX-603

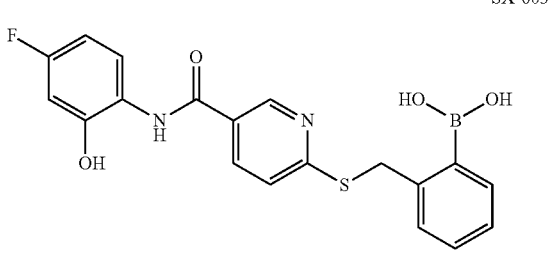

SX-622

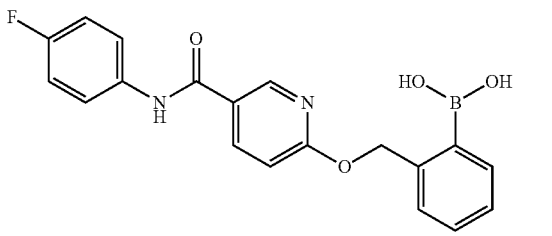

SX-660
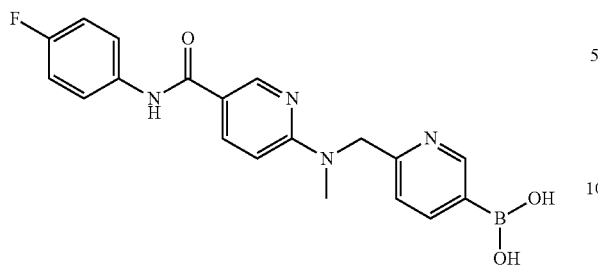

SX-662
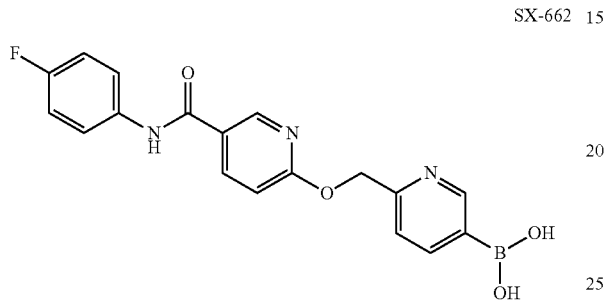

SX-671
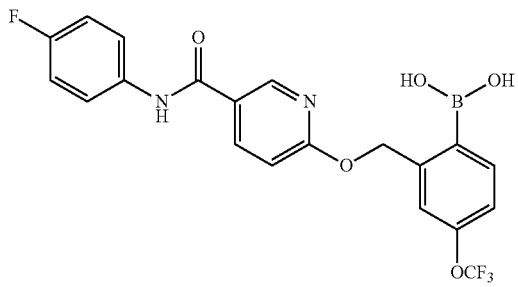

SX-677
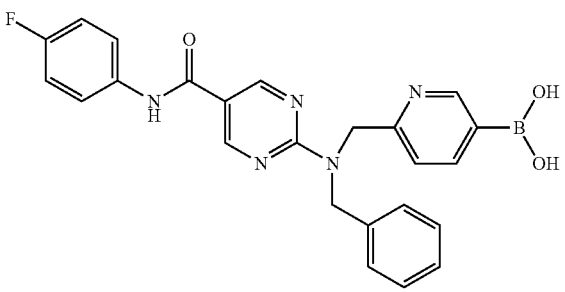

SX-678
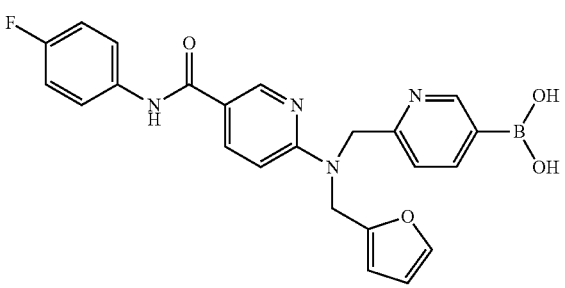

SX-682
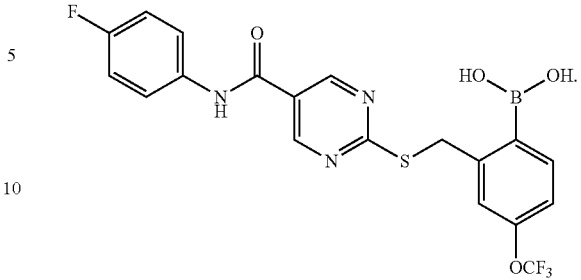

or a pharmaceutically suitable solvate or salt thereof;
wherein the cancer being treated is selected from the group consisting of breast cancer, colorectal cancer, glioblastoma, lung cancer, melanoma, pancreatic cancer, prostate cancer, renal cell carcinoma, thyroid tumors, gastric cancer, ovarian cancer, lymphomas, hematologic malignancies, myelodysplastic syndrome, acute myelogenous leukemia, myeloma, sarcoma and bladder cancer.

2. The method of claim 1, wherein the pharmaceutical composition comprises a therapeutically effective amount of the compound of formula SX-682.

3. The method of claim 1, further comprising administering carboplatin, wherein the cancer being treated is selected from breast cancer and melanoma.

4. The method of claim 1, further comprising administering an antibody selected from the group consisting of ipilimumab, abatacept, nivolumab, pembrolizumab, tremelimumab, pidilizumab, atezolizumab, durvalumab, avelumab, nivolumab, pembrolizumab, lambrolizumab, MEDI-0680, pidilizumab, AMP-224, atezolizumab, durvalumab, BMS-936559, MSB0010718C, BMS-986016, IMP-731, IMP-321, urelumab, PF-05082566, RG-7888, lucatumumab, dacetuzumab, varlilumab, enoblituzumab, G7155, and FPA-008, wherein the cancer being treated is selected from breast cancer and melanoma.

5. The method of claim 1, further comprising administering an antibody selected from the group consisting of ipilimumab, abatacept, nivolumab, pembrolizumab, tremelimumab, pidilizumab, atezolizumab, durvalumab, and avelumab, wherein the cancer being treated is selected from melanoma and lung cancer.

6. The method of claim 1, wherein the cancer is selected from colorectal cancer, melanoma, and cancers of the prostate, pancreas, breast, lung, glioblastoma, and mesothelioma.

7. The method of claim 1, wherein the cancer is breast cancer.

8. The method of claim 7, wherein the pharmaceutical composition is administered orally.

9. The method of claim 7, further comprising administering a platinum chemotherapy.

10. The method of claim 1, further comprising administering an antibody directed to a ligand selected from the group consisting of B7-1, B7-2, B7-H1 (PD-L1), B7-DC (PD-L2), B7-H2 (ICOS-L), B7-H3, B7-H4, B7-H5 (VISTA), B7-H6CD40, CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβPR, LIGHT, DcR3, HVEM, VEGI/TL1A, TRAMP/

DR3, EDAR, EDA1, XEDAR, EDA2, TNFR1, lymphotoxin α/TNFβ, TNFR2, TNFα, LTβR, lymphotoxin α1β2, FAS, FASL, RELT, DR6, TROY, NGFR, IL-6, IL-10, TGF-β, VEGF, CTLA-4, PD-1, PD-L1, PD-L2, LAG-3, TIM-3, galectin 9, CEACAM-1, BTLA, CD69, galectin-1, TIGIT, CD113, GPR56, VISTA, 2B4, CD48, GARP, PD1H, LAIR1, TIM-1, and TIM-4, wherein the cancer being treated is selected from melanoma and lung cancer.

11. The method of claim 10, wherein the antibody binds to a ligand selected from the group consisting of B7-1, B7-2, B7-H1 (PD-L1), B7-DC (PD-L2), B7-H2 (ICOS-L), B7-H3, B7-H4, B7-H5 (VISTA), and B7-H6.

12. The method of claim 10, wherein the antibody binds to a ligand selected from CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, lymphotoxin αTNFβ, TNFR2, TNFα, LT/βR, lymphotoxin α1β2, FAS, FASL, RELT, DR6, TROY, and NGFR.

13. The method of claim 10, wherein the antibody binds to a ligand selected from IL-6, IL-10, TGF-β, and VEGF.

14. The method of claim 1, further comprising administering an antibody that binds to a checkpoint inhibitor selected from the group consisting of CTLA-4, PD-1, PD-L1, PD-L2, LAG-3, TIM-3, galectin 9, CEACAM-1, BTLA, CD69, galectin-1, TIGIT, CD113, GPR56, VISTA, 2B4, CD48, GARP, PD1H, LAIR1, TIM-1, and TIM-4, wherein the cancer being treated is selected from melanoma and lung cancer.

15. The method of claim 1, further comprising administering an antibody that binds to an agonist of a protein selected from the group consisting of B7-1, B7-2, CD28, 4-1BB (CD137), 4-1BBL, ICOS, ICOS-L, OX40, OX40L, GITR, GITRL, CD70, CD27, CD40, DR3 and CD2, wherein the cancer being treated is selected from melanoma and lung cancer.

16. The method of claim 4, wherein the antibody is G7155 or FPA-008.

17. The method of claim 4, wherein the antibody is ipilimumab or tremelimumab.

18. The method of claim 4, wherein the antibody is selected from the group consisting of nivolumab, pembrolizumab, lambrolizumab, MEDI-0680, pidilizumab, AMP-224, atezolizomab, durvalumab, BMS-936559, and MSB0010718C.

19. The method of claim 4, wherein the antibody is selected from the group consisting of BMS-986016, IMP-731, and IMP-321.

20. The method of claim 4, wherein the antibody is urelumab or utomilumab.

21. The method of claim 4, wherein the antibody is selected from the group consisting of BMS-986153, BMS-986156, TRX-518 and MK-4166.

22. The method of claim 4, wherein the antibody is MEDI-6383 or MEDI-6469.

23. The method of claim 1, further comprising administering an IDO and/or TDO inhibitor-selected from the group consisting of indoximod, GDC-0919, F001287, GDC-0919 (NLG919), F001287, epacadostat (INCB024360), IDO-IN-1, IDO-IN-2, navoximod (IDO-IN-7), and molecules with the following structures:

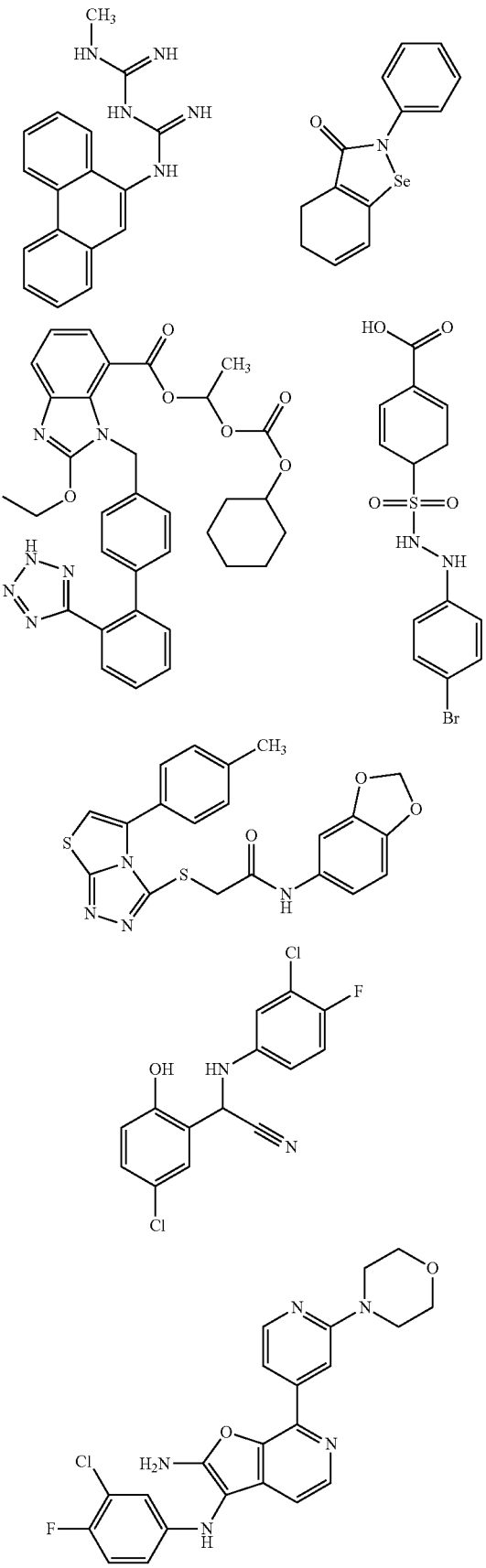

57
-continued
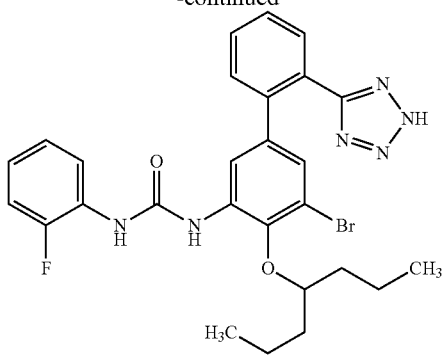
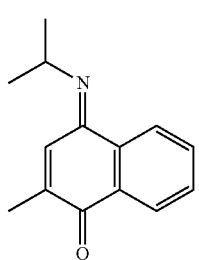
58
-continued
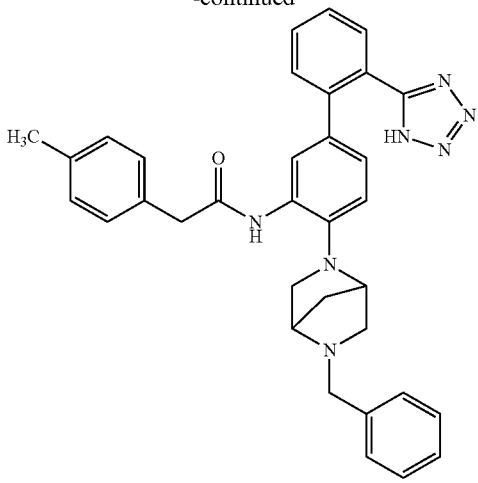
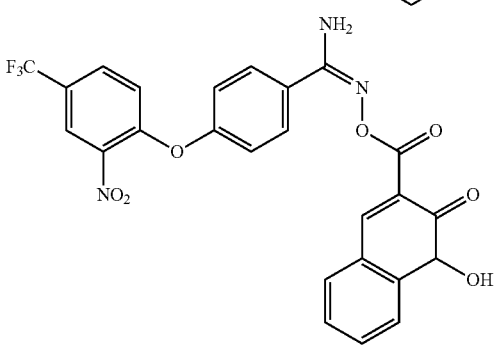
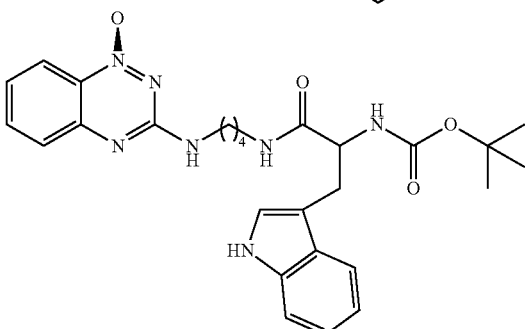
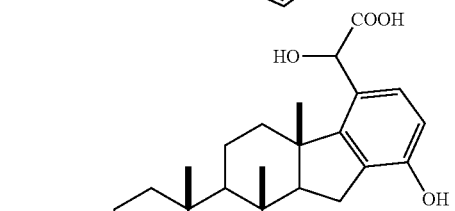
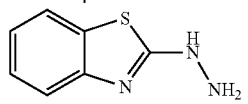   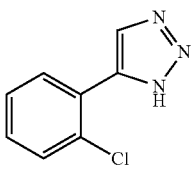

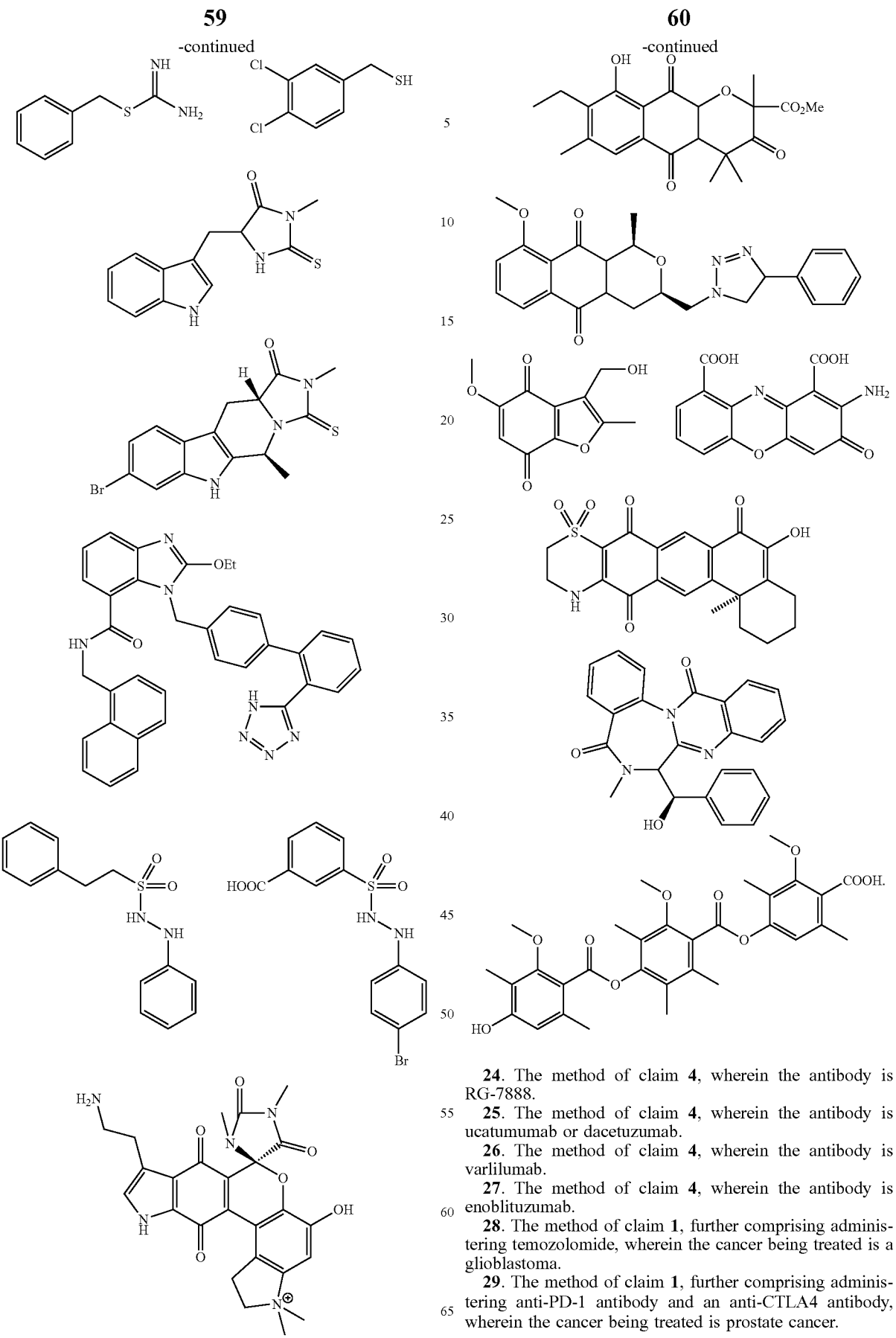

24. The method of claim 4, wherein the antibody is RG-7888.
25. The method of claim 4, wherein the antibody is ucatumumab or dacetuzumab.
26. The method of claim 4, wherein the antibody is varlilumab.
27. The method of claim 4, wherein the antibody is enoblituzumab.
28. The method of claim 1, further comprising administering temozolomide, wherein the cancer being treated is a glioblastoma.
29. The method of claim 1, further comprising administering anti-PD-1 antibody and an anti-CTLA4 antibody, wherein the cancer being treated is prostate cancer.

* * * * *